United States Patent
Korennykh et al.

(10) Patent No.: US 11,667,949 B2
(45) Date of Patent: Jun. 6, 2023

(54) REPORTER CONSTRUCT AND BIOSENSOR FOR INTERFERON SECOND MESSENGER 2-5A

(71) Applicant: The Trustees of Princeton University, Princeton, NJ (US)

(72) Inventors: Alexei Korennykh, Princeton, NJ (US); Alisha Chitrakar, Princeton, NJ (US); Jesse Donovan, Princeton, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 409 days.

(21) Appl. No.: 16/277,632

(22) Filed: Feb. 15, 2019

(65) Prior Publication Data

US 2019/0249223 A1 Aug. 15, 2019

Related U.S. Application Data

(60) Provisional application No. 62/631,188, filed on Feb. 15, 2018.

(51) Int. Cl.
| | | |
|---|---|---|
| C12Q 1/44 | (2006.01) | |
| C12N 9/22 | (2006.01) | |
| C12N 9/02 | (2006.01) | |
| C12Q 1/66 | (2006.01) | |

(52) U.S. Cl.
CPC ............ *C12Q 1/44* (2013.01); *C12N 9/0069* (2013.01); *C12N 9/22* (2013.01); *C12Q 1/66* (2013.01); *C12Y 113/12007* (2013.01); *C07K 2319/61* (2013.01); *G01N 2500/02* (2013.01); *G01N 2800/52* (2013.01)

(58) Field of Classification Search
None
See application file for complete search history.

(56) References Cited

U.S. PATENT DOCUMENTS

| | | |
|---|---|---|
| RE30,985 E | 6/1982 | Cartaya |
| 4,560,655 A | 12/1985 | Baker |
| 4,657,866 A | 4/1987 | Kumar |
| 4,767,704 A | 8/1988 | Cleveland et al. |
| 4,927,762 A | 5/1990 | Darfler |
| 5,122,469 A | 6/1992 | Mather et al. |
| 2015/0099271 A1 | 4/2015 | Waldo et al. |

FOREIGN PATENT DOCUMENTS

| | | |
|---|---|---|
| WO | WO-87/00195 A1 | 1/1987 |
| WO | WO-93/09239 A1 | 5/1993 |
| WO | WO-93/19191 A1 | 9/1993 |
| WO | WO-94/12649 A2 | 6/1994 |
| WO | WO-94/28938 A1 | 12/1994 |
| WO | WO-95/00655 A1 | 1/1995 |
| WO | WO-95/11984 A2 | 5/1995 |
| WO | WO-2005/074436 A2 | 8/2005 |

OTHER PUBLICATIONS

Muller et al., Random peptide libraries displayed on adenoassociated virus to select for targeted gene therapy vectors. Nature Biotechnology 21 (9) : 1040 (Year: 2003).*
UniProtKB—A0A059PIR9 (A0A059PIR9_AEQVI) YFP (Year: 2014).*
UniProtKB—Q9U6Y8 (RFP_DISSP)—GFP (Year: 1995).*
UniProtKB—Q9U6Y8 (RFP_DISSP)—RFP (Year: 2000).*
Al-Ahmadi et al., RNase L downmodulation of the RNA-binding protein, HuR, and cellular growth. Oncogene 28(15):1782-91 (2009).
Ali et al., Adeno-associated virus gene transfer to mouse retina, Hum. Gene Ther., 9(1):81-6 (Jan. 1998).
Ali et al., Gene transfer into the mouse retina mediated by an adeno-associated viral vector, Hum. Mol. Genet., 5:591-4 (1996).
Altschul et al., Gapped BLAST and PSI-BLAST: a new generation of protein database search programs, Nucleic Acids Res. 25:3389-402 (1997).
Banerjee et al., Cell-type-specific effects of RNase L on viral induction of beta interferon, MBio, 5(2):e00856-14 (Feb. 2014).
Banerjee et al., RNase L is a negative regulator of cell migration, Oncotarget, 6(42):44360-72 (Dec. 2015).
Barnes et al., Methods for growth of cultured cells in serum-free medium, Anal. Biochem., 102(2):255-70 (Mar. 1980).
Bennett et al., Real-time, noninvasive in vivo assessment of adeno-associated virus-mediated retinal transduction, Invest. Opthalmol. Vis. Sci., 38:2857-63 (1997).
Besse et al., Ultrastructural localization of interferon-inducible double-stranded RNA-activated enzymes in human cells, Exp. Cell Res., 239(2):379-92 (Mar. 1998).
Birdwell et al., Activation of RNase L by Murine Coronavirus in Myeloid Cells Is Dependent on Basal Oas Gene Expression and Independent of Virus-Induced Interferon, J. Virol., 90(6):3160-72 (Jan. 2016).
Bitter et al., Expression and secretion vectors for yeast, Methods in Enzymology, 153:516-44(1987).
Borras et al., Adenoviral reporter gene transfer to the human trabecular meshwork does not alter aqueous humor outflow. Relevance for potential gene therapy of glaucoma, Gene Ther., 6(4):515-24 (Apr. 1999).
Braun et al., Immunogenic duplex nucleic acids are nuclease resistant, J. Immunol., 141(6):2084-9 (Sep. 1988).
Carpten et al. Germline mutations in the ribonuclease L gene in families showing linkage with HPC1. Nat. Genet. 30(2):181-4 (Feb. 2002).
Chakrabarti et al., New insights into the role of RNase L in innate immunity. J. Interferon Cytokine Res. 31 (1):49-57 (Jan. 2011).
Chaturvedi et al., Stabilization of triple-stranded oligonucleotide complexes: use of probes containing alternating phosphodiester and stereo-uniform cationic phosphoramidate linkages, Nucleic Acids Res., 24(12):2318-23 (Jun. 1996).

(Continued)

*Primary Examiner* — Ethan C Whisenant
(74) *Attorney, Agent, or Firm* — Marshall, Gerstein & Borun LLP

(57) ABSTRACT

The present disclosure relates, in general, to a fusion protein construct comprising RNase L and a split reporter system, and methods of using the reporter for detecting 2'-5' linked oligoadenylates (2-5A) and double stranded RNA in vivo.

20 Claims, 13 Drawing Sheets

Specification includes a Sequence Listing.

(56) References Cited

OTHER PUBLICATIONS

Chiappinelli et al. Inhibiting DNA Methylation Causes an Interferon Response in Cancer via dsRNA Including Endogenous Retroviruses. Cell. 162(5):974-86 (Aug. 2015).
Chitrakar et al., Realtime 2-5A kinetics suggests interferons B and ? evade global arrest of translation by RNase L, posted online at: <https://www.biorxiv.org/content/10.1101/476341v1> (Nov. 26, 2018).
Clemens et al., Inhibition of cell-free protein synthesis by pppA2'p5'A2'p5'A: a novel oligonucleotide synthesized by interferon-treated L cell extracts, Cell, 13(3):565-72 (Mar. 1978).
Cooper et al., Ribonuclease L and metal-ion-independent endoribonuclease cleavage sites in host and viral RNAs, Nucleic Acids Res., 42(8):5202-16 (Apr. 2014).
Donovan et al., Rapid RNase L-driven arrest of protein synthesis in the dsRNA response without degradation of translation machinery, RNA, 23(11):1660-71 (Nov. 2017).
Fabre et al., RNase L controls terminal adipocyte differentiation, lipids storage and insulin sensitivity via CHOP10 mRNA regulation, Cell Death Differ., 19(9):1470-81 (Sep. 2012).
Feng et al., Progressive sequence alignment as a prerequisite to correct phylogenetic trees, J. Mol. Evol., 25:351-60 (1987).
Flannery et al., Efficient photoreceptor-targeted gene expression in vivo by recombinant adeno-associated virus, Proc. Natl. Acad. Sci. USA, 94(13):6916-21 (Jun. 1997).
Flotte et al., Stable in vivo expression of the cystic fibrosis transmembrane conductance regulator with an adeno-associated virus vector, Proc Natl Acad Sci USA, 90:10613-7 (1993).
George et al., Editing of cellular self RNAs by adenosine deaminase ADAR1 suppresses innate immune stress responses. J. Biol. Chem. 291(12):6158-68 (Mar. 2016).
Goubau et al., Cytosolic sensing of viruses. Immunity, 38(5):855-69 (May 2013).
Graham et al., Characteristics of a human cell line transformed by DNA from human adenovirus type 5, J. Gen. Virol., 36(1):59-74 (Jul. 1977).
Ham et al., Media and growth requirements, Methods Enzymol., 58:44-93 (1979).
Han et al., Innate immune messenger 2-5A tethers human RNase L into active high-order complexes, Cell Rep., 2(4):902-13 (Oct. 2012).
Han et al., Structure of human RNase L reveals the basis for regulated RNA decay in the IFN response, Science, 343(6176):1244-8 (Mar. 2014).
Higgins et al., Fast and sensitive multiple sequence alignments on a microcomputer, Comput. Appl. Biosci., 5(2):151-3 (1989).
Hovanessian et al., The human 2'-5'oligoadenylate synthetase family: unique interferon-inducible enzymes catalyzing 2'-5' instead of 3'-5' phosphodiester bond formation, Biochimie, 89(6-7):779-88 (Jun.-Jul. 2007).
Hsieh et al., The translational landscape of mTOR signalling steers cancer initiation and metastasis, Nature, 485(7396):55-61 (Feb. 2012).
Huang et al., Inhibition of type I and type III interferons by a secreted glycoprotein from Yaba-like disease virus, Proc. Natl. Acad. Sci. USA, 104(23):9822-7 (Jun. 2007).
Jomary et al., Rescue of photoreceptor function by AAV-mediated gene transfer in a mouse model of inherited retinal degeneration, Gene Ther., 4:683-90 (1997).
Kjaer et al., Mitochondrial localization of the OAS1 p46 isoform associated with a common single nucleotide polymorphism, BMC Cell Biol., 15:33 (Sep. 2014).
Kotenko et al., IFN-lambdas mediate antiviral protection through a distinct class II cytokine receptor complex, Nat. Immunol. 4(1):69-77 (Jan. 2003).
Kristiansen et al., The oligoadenylate synthetase family: an ancient protein family with multiple antiviral activities. J. Interferon Cytokine Res. 31(1), 41-7 (Jan. 2011).
Lane et al., The energetics of genome complexity, Nature, 467(7318):929-34 (Oct. 2010).
Latimer et al., Specificity of monoclonal antibodies produced against phosphorothioate and ribo modified DNAs, Mol. Immunol., 32(14-15):1057-64 (Oct. 1995).
Li et al. An essential role for the antiviral endoribonuclease, RNase-L, in antibacterial immunity. Proc. Natl. Acad. Sci. USA, 105(52):20816-21 (Dec. 2008).
Li et al., In vivo transfer of a reporter gene to the retina mediated by an adenoviral vector, Invest. Ophthalmol. Vis. Sci., 35(5):2543-9 (Apr. 1994).
Li et al., Phenotype correction in retinal pigment epithelium in murine mucopolysaccharidosis VII by adenovirus-mediated gene transfer, Proc. Natl. Acad. Sci. USA, 92(17):7700-4 (Aug. 1995).
Licht, DNA Methylation Inhibitors in Cancer Therapy: The Immunity Dimension. Cell, 162(5):938-9 (Aug. 2015).
Liddicoat et al., RNA editing by ADAR1 prevents MDA5 sensing of endogenous dsRNA as nonself, Science, 349(6252):1115-20 (Sep. 2015).
Lu et al., The structural basis of 5' triphosphate double-stranded RNA recognition by RIG-I C-terminal domain. Structure, 18(8):1032-43 (Aug. 2011).
Lukacs et al., Size-dependent DNA mobility in cytoplasm and nucleus, J. Biol. Chern., 275:1625-9 (Jan. 2000).
Malathi et al., Small self-RNA generated by RNase L amplifies antiviral innate immunity, Nature, 448(7155):816-9 (Aug. 2007).
Mather et al., Culture of testicular cells in hormone-supplemented serum-free medium, Ann. N. Y Acad. Sci., 383:44-68 (1982).
Mather et al., Establishment and characterization of two distinct mouse testicular epithelial cell lines, Biol. Reprod., 23:243-52 (1980).
Mendelson et al., Expression and rescue of a nonselected marker from an integrated AAV vector, Virology, 166(1):154-65 (Sep. 1988).
Miyoshi et al., Stable and efficient gene transfer into the retina using an HIV-based lentiviral vector, Proc Natl Acad Sci USA, 94:10319-23 (1997).
Mullan et al., The 2,5 oligoadenylate synthetase/RNaseL pathway is a novel effector of BRCA1-and interferon-gamma-mediated apoptosis. Oncogene, 24(35): 5492-501 (2005).
NCBI Reference Sequence: NM_021133.3, *Homo sapiens* ribonuclease L (RNASEL), mRNA (Nov. 17, 2018).
NCBI Reference Sequence: NP_066956.1, 2-5A-dependent ribonuclease [*Homo sapiens*] (Feb. 28, 2019).
Needleman et al., A general method applicable to the search for similarities in the amino acid sequence of two proteins, J. Mol. Biol., 48(3):443-53 (1970).
Paulmurugan et al., Combinatorial library screening for developing an improved split-firefly luciferase fragment-assisted complementation system for studying protein-protein interactions, 79(6):2346-53 (Mar. 2007).
Pearson et al., Improved tools for biological sequence comparison, Proc. Natl. Acad. Sci. USA, 85:2444-8 (1988).
Peyrottes et al., Oligodeoxynucleoside phosphoramidates (P-NH2): synthesis and thermal stability of duplexes with DNA and RNA targets, Nucleic Acids Res., 24(10):1841-8 (May 1996).
Rath et al. Human RNase L tunes gene expression by selectively destabilizing the microRNA-regulated transcriptome. Proc. Natl. Acad. Sci. USA. 112(52):15916-21 (Dec. 2015).
Rice et al., Mutations in ADAR1 cause Aicardi-Goutières syndrome associated with a type I interferon signature, Nat. Genet., 44(11):1243-8 (Nov. 2012).
Roulois et al., DNA-Demethylating Agents Target Colorectal Cancer Cells by Inducing Viral Mimicry by Endogenous Transcripts. Cell. 162(5):961-73 (Aug. 2015).
Sadler et al., Interferon-inducible antiviral effectors, Nat. Rev. Immunol., 8(7):559-68 (Jul. 2008).
Sakamoto et al., A vitrectomy improves the transfection efficiency of adenoviral vector-mediated gene transfer to Müller cells, Gene Ther., 5(8):1088-97 (Aug. 1998).
Samuel et al. PKR and RNase L contribute to protection against lethal West Nile Virus infection by controlling early viral spread in the periphery and replication in neurons. J. Virol. 80(14):7009-19 (Jul. 2006).

(56) References Cited

OTHER PUBLICATIONS

Samulski et al., Helper-free stocks of recombinant adeno-associated viruses: normal integration does not require viral gene expression, J. Vir., 63:3822-8 (1989).

Schultz et al., Oligo-2'-fluoro-2'-deoxynucleotide N3'-->P5' phosphoramidates: synthesis and properties, Nucleic Acids Res., 24(15):2966-73 (Aug. 1996).

Silverman, Viral encounters with 2',5'-oligoadenylate synthetase and RNase L during the interferon antiviral response. J. Virol. 81(23): 12720-9 (2007).

Smith et al., Comparison of biosequences, Advances in Applied Mathematics, 2(4):482-9 (1981).

Stark et al., 2-5A synthetase: assay, distribution and variation with growth or hormone status, Nature, 278(5703):471-3 (Mar. 1979).

Takahashi et al., Rescue from photoreceptor degeneration in the rd mouse by human immunodeficiency virus vector-mediated gene transfer, J. Virol., 73:7812-6 (1999).

Thakur et al., A convenient and sensitive fluorescence resonance energy transfer assay for RNase L and 2',5' oligoadenylates, Methods Mol. Med., 116:103-13 (2005).

Thompson et al., Clustal W: improving the sensitivity of progressive multiple sequence alignment through sequence weighting, position-specific gap penalties and weight matrix choice, Nucleic Acids Res., 22: 4673-80 (1994).

Urlaub et al., Isolation of Chinese hamster cell mutants deficient in dihydrofolate reductase activity, Proc. Natl. Acad. Sci. USA, 88(7):4216-20 (Jul. 1980).

Washenberger et al. Hepatitis C virus RNA: dinucleotide frequencies and cleavage by RNase L. Virus Res. 130(1-2):85-95 (Dec. 2007).

West et al., Induction and maintenance of 2',5'-oligoadenylate synthetase in interferon-treated chicken embryo cells, Mol. Cell Biol., 2(11):1436-43 (Nov. 1982).

White et al., Human nuclear Dicer restricts the deleterious accumulation of endogenous double-stranded RNA, Nat. Struct. Mol. Biol., 21(6):552-9 (Jun. 2014).

Williams et al., Synthesis and breakdown of pppA2'p5'A2'p5'A and transient inhibiton of protein synthesis in extracts from interferon-treated and control cells, Eur J. Biochem., 92(2):455-62 (Dec. 1978).

Wreschner et al., Interferon action--sequence specificity of the ppp(A2'p)nA-dependent ribonuclease, Nature, 289(5796):414-7 (Jan. 1981).

Wreschner et al., Ribosomal RNA cleavage, nuclease activation and 2-5A(ppp(A2'p)nA) in interferon-treated cells, Nucleic Acids Res., 9(7):1571-81 (Apr. 1981).

Wu et al., Structural basis for dsRNA recognition, filament formation, and antiviral signal activation by MDA5. Cell 152(1-2):276-89 (2013).

Zarnitsyn et al., Modeling transmembrane transport through cell membrane wounds created by acoustic cavitation, Biophys. J., 95(9):4124-38 (Nov. 2008).

Zhao et al., Antagonism of the interferon-induced OAS-RNase L pathway by murine coronavirus ns2 protein is required for virus replication and liver pathology, Cell Host Microbe, 11(6):607-16 (Jun. 2012).

Zhou et al. Interferon action and apoptosis are defective in mice devoid of 2',5'-oligoadenylate-dependent RNase L. EMBO J. 16(21): 6355-63 (1997).

Zhou et al., Expression cloning of 2-5A-dependent RNAase: a uniquely regulated mediator of interferon action. Cell 72(5):753-65 (Mar. 1993).

\* cited by examiner

| reporters with variant linkers | L1 | L2 |
|---|---|---|
| V1 | (GGGS) | (GGGS)$_2$ |
| V2 | GS(GGGS)$_2$ | (GGGS)$_2$ |
| V3 | (GGGS)$_4$ | (GGGS)$_2$ |
| V4 | (GGGS)$_3$ | (GGGS) |
| V5 | (GGGS)$_3$ | (GGGS)$_3$ |
| V6 | (GGGS)$_3$ | (GGGS)$_2$ |

FIG. 9A
FIG. 9B
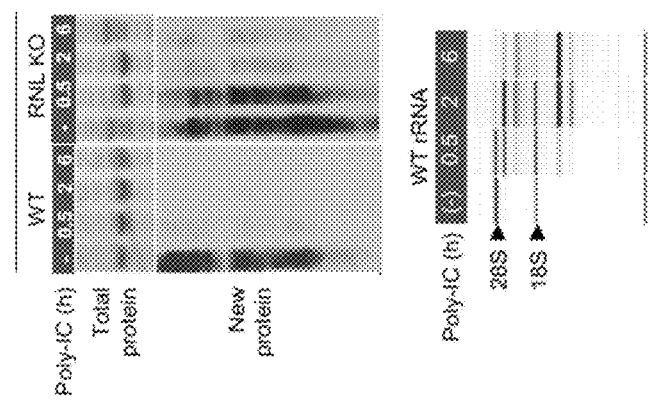
FIG. 9C
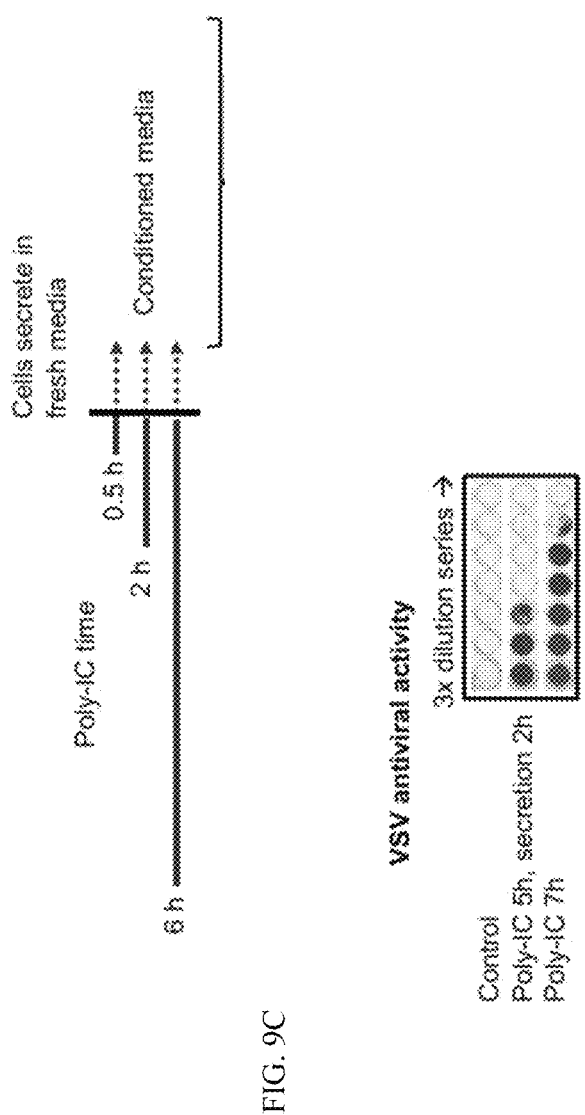

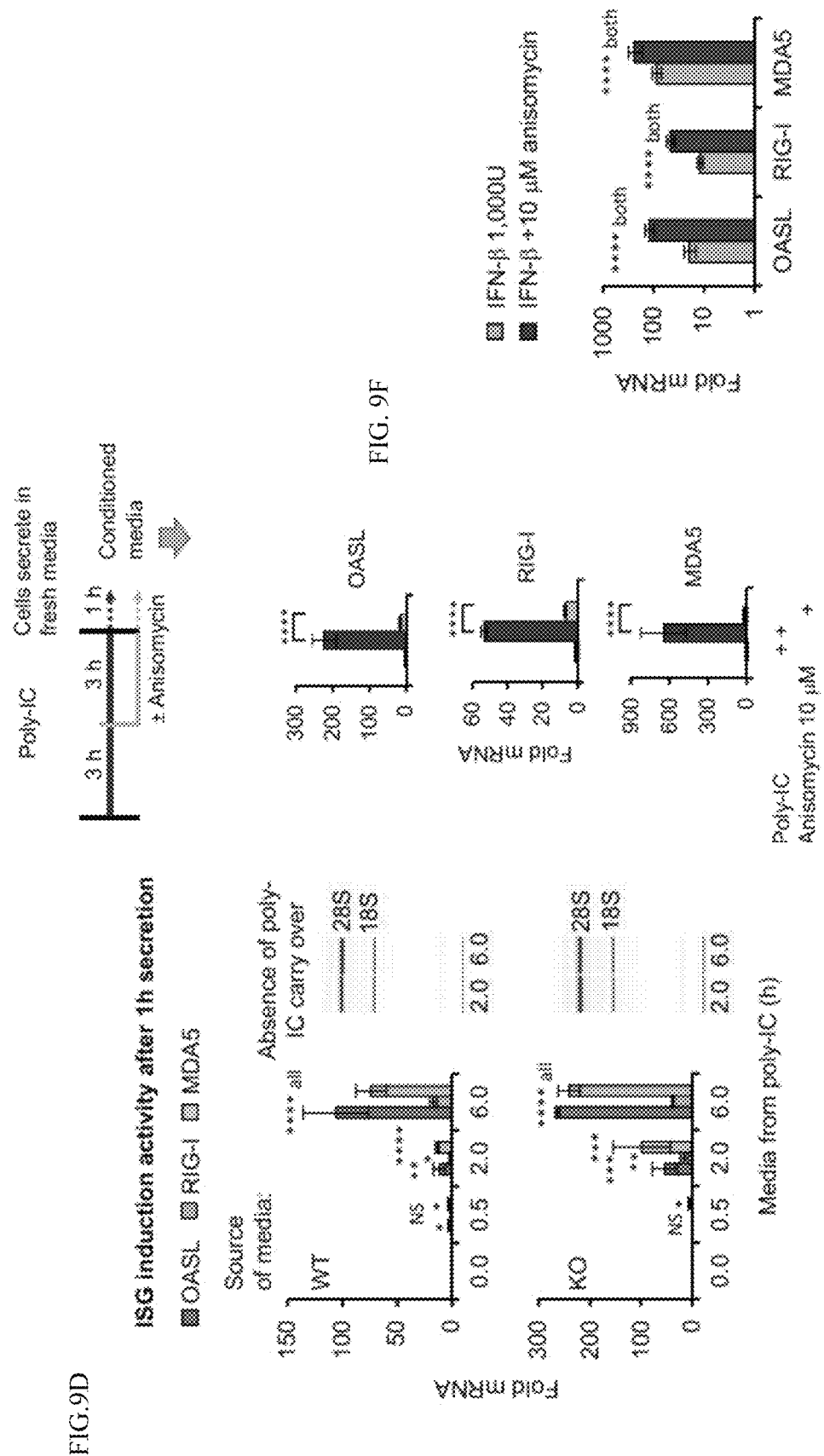

SEQUENCE LISTING

```
<160> NUMBER OF SEQ ID NOS: 26

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 1

Gly Gly Gly Ser
1

<210> SEQ ID NO 2
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 2

Gly Gly Gly Ser Gly Gly Gly Ser
1               5

<210> SEQ ID NO 3
<211> LENGTH: 12
<212> TYPE: PRT
<213> ORGANISM: Artificial Sequence
<220> FEATURE:
<223> OTHER INFORMATION: Synthetic Peptide
```

```
<400> SEQUENCE: 3

Gly Gly Gly Ser Gly Gly Gly Ser Gly Gly Gly Ser
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 4

Pro Lys Lys Lys Arg Lys Val Glu
1               5

<210> SEQ ID NO 5
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 5

Leu Gln Leu Pro Pro Leu Glu Arg Leu Thr Leu Asp
1               5                   10

<210> SEQ ID NO 6
<211> LENGTH: 12
<212> TYPE: DNA
<213> ORGANISM: Artificial Sequence
<220> FEATURE:
<223> OTHER INFORMATION: Synthetic Polynucleotide

<400> SEQUENCE: 6
gcttctagtt ag                                                           12

<210> SEQ ID NO 7
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 7
cttacacctg attcatttcc                                                   20

<210> SEQ ID NO 8
<211> LENGTH: 12
<212> TYPE: DNA
<213> ORGANISM: Artificial Sequence
<220> FEATURE:
<223> OTHER INFORMATION: Synthetic Polynucleotide

<400> SEQUENCE: 8
aggaactgga gc                                                           12

<210> SEQ ID NO 9
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 9
agactctctg tgtccctcat                                                   20
```

<210> SEQ ID NO 10
<211> LENGTH: 12
<212> TYPE: DNA
<213> ORGANISM: Artificial Sequence
<220> FEATURE:
<223> OTHER INFORMATION: Synthetic Polynucleotide

<400> SEQUENCE: 10
cactcttcca gc          12

<210> SEQ ID NO 11
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 11
gtacaggtct ttgcggatg          19

<210> SEQ ID NO 12
<211> LENGTH: 555
<212> TYPE: PRT
<213> ORGANISM: Artificial Sequence
<220> FEATURE:
<223> OTHER INFORMATION: Synthetic Polypeptide

<400> SEQUENCE: 12

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Arg Gly Glu
            20                  25                  30

Gly Glu Gly Asp Ala Thr Ile Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Lys Tyr Lys Thr Arg Ala Val Val
            100                 105                 110

Lys Phe Glu Gly Asp Thr Leu Val Asn Arg Ile Glu Leu Lys Gly Thr
        115                 120                 125

Asp Phe Lys Glu Asp Gly Asn Ile Leu Gly His Lys Leu Glu Tyr Asn
    130                 135                 140

Phe Asn Ser His Asn Val Tyr Ile Thr Ala Asp Lys Gln Lys Asn Gly
145                 150                 155                 160

Ile Lys Ala Asn Phe Thr Val Arg His Asn Val Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Thr Val Leu Ser
        195                 200                 205

Lys Asp Pro Asn Glu Lys Gly Gly Ser Gly Gly Ser Gly Gly
    210                 215                 220

Gly Ser Ala Ala Val Glu Asp Asn His Leu Leu Ile Lys Ala Val Gln
225                 230                 235                 240
```

```
Asn Glu Asp Val Asp Leu Val Gln Gln Leu Leu Glu Gly Gly Ala Asn
                245                 250                 255

Val Asn Phe Gln Glu Glu Glu Gly Gly Trp Thr Pro Leu His Asn Ala
            260                 265                 270

Val Gln Met Ser Arg Glu Asp Ile Val Glu Leu Leu Leu Arg His Gly
        275                 280                 285

Ala Asp Pro Val Leu Arg Lys Lys Asn Gly Ala Thr Pro Phe Ile Leu
    290                 295                 300

Ala Ala Ile Ala Gly Ser Val Lys Leu Leu Lys Leu Phe Leu Ser Lys
305                 310                 315                 320

Gly Ala Asp Val Asn Glu Cys Asp Phe Tyr Gly Phe Thr Ala Phe Met
                325                 330                 335

Glu Ala Ala Val Tyr Gly Lys Val Lys Ala Leu Lys Phe Leu Tyr Lys
            340                 345                 350

Arg Gly Ala Asn Val Asn Leu Arg Arg Lys Thr Lys Glu Asp Gln Glu
        355                 360                 365

Arg Leu Arg Lys Gly Gly Ala Thr Ala Leu Met Asp Ala Ala Glu Lys
    370                 375                 380

Gly His Val Glu Val Leu Lys Ile Leu Leu Asp Glu Met Gly Ala Asp
385                 390                 395                 400

Val Asn Ala Cys Asp Asn Met Gly Arg Asn Ala Leu Ile His Ala Leu
                405                 410                 415

Leu Ser Ser Asp Asp Ser Asp Val Glu Ala Ile Thr His Leu Leu Leu
            420                 425                 430

Asp His Gly Ala Asp Val Asn Val Arg Gly Glu Arg Gly Lys Thr Pro
        435                 440                 445

Leu Ile Leu Ala Val Glu Lys Lys His Leu Gly Leu Val Gln Arg Leu
    450                 455                 460

Leu Glu Gln Glu His Ile Glu Ile Asn Asp Thr Asp Ser Asp Gly Lys
465                 470                 475                 480

Thr Ala Leu Leu Leu Ala Val Glu Leu Lys Leu Lys Lys Ile Ala Glu
                485                 490                 495

Leu Leu Cys Lys Arg Gly Ala Ser Thr Asp Cys Gly Asp Leu Val Met
            500                 505                 510

Thr Ala Arg Arg Asn Tyr Asp His Ser Leu Val Lys Val Leu Leu Ser
        515                 520                 525

His Gly Ala Gly Gly Ser Gly Gly Gly Ser Arg Asp His Met Val
    530                 535                 540

Leu His Glu Tyr Val Asn Ala Ala Gly Ile Thr
545                 550                 555

<210> SEQ ID NO 13
<211> LENGTH: 1665
<212> TYPE: DNA
<213> ORGANISM: Artificial Sequence
<220> FEATURE:
<223> OTHER INFORMATION: Synthetic Polynucleotide

<400> SEQUENCE: 13
atgtccaaag gagaagaact gtttaccggt gttgtgccaa ttttggttga actcgatggt      60
gatgtcaacg gacataagtt ctcagtgaga ggcgaaggag aaggtgacgc caccattgga     120
aaattgactc ttaaattcat ctgtactact ggtaaacttc ctgtaccatg gccgactctc     180
gtaacaacgc ttacgtacgg agttcagtgc ttttcgagat acccagacca tatgaaaaga     240
catgactttt ttaagtcggc tatgcctgaa ggttacgtgc aagaaagaac aatttcgttc     300
```

-continued

```
aaagatgatg gaaatataa aactagagca gttgttaaat ttgaaggaga tactttggtt       360
aaccgcattg aactgaaagg aacagatttt aagaagatg gtaatattct tggacacaaa      420
ctcgaataca attttaatag tcataacgta tacatcactg ctgataagca aaagaacgga      480
attaaagcga atttcacagt acgccataat gtagaagatg cagtgttca acttgccgac      540 cattaccaac aaaacacccc tattggagac ggtccggtac ttcttcctga taatcactac    600
ctctcaacac aaacagtcct gagcaaagat ccaaatgaaa aaggaggcgg atccggagga    660
ggctccggcg gcggctccgc tgctgtcgaa gacaaccacc tcctgatcaa agccgtgcaa    720
aacgaggacg tcgatctcgt ccaacaactc ctcgaaggcg cgctaacgt caatttttcaa   780 gaggaggagg gcggctggac ccctctccat aacgccgtgc aaatgagcag gaagacatt   840 gtggagctcc tcctcaggca tggagctgac cctgtcctca gaaagaagaa cggagccacc  900
ccctttatcc tggccgccat tgctggctcc gtcaagctcc tcaagctctt cctgagcaaa   960
ggcgccgacg tcaatgagtg cgacttctac ggattcacag cctttatgga agccgctgtg  1020
tacggcaagg tgaaggccct gaagttcctc tacaaaaggg gcgccaacgt gaacctgaga  1080 aggaaaaacca aggaggatca ggagagactg aggaaaggcg gagctaccgc cctcatggat 1140
gctgccgaaa agggccacgt ggaagtcctg aagatcctcc tcgacgaaat gggcgctgac  1200
gtgaacgctt gcgacaacat gggaaggaat gctctgatcc acgctctcct cagcagcgac 1260
gactccgacg tggaagctat cacccacctc ctcctggatc acggcgccga tgtcaacgtc 1320
agaggagaaa gaggaaagac ccccctcatc ctggctgtgg agaaaaagca tctcggactc 1380
gtgcagagac tgctggagca agagcacatc gagatcaatg acaccgatag cgacggcaaa 1440
accgctctcc tcctcgccgt ggagctgaag ctgaagaaga tcgctgagct gctctgtaaa 1500
agaggcgcta gcacagactg cggagacctg gtcatgacag ccagaaggaa ctacgaccac 1560
tccctggtga aagtcctcct cagccatgga gctggcggag aagcggcgg aggctcccgt  1620 gaccacatgg tccttcatga gtatgtaaat gctgccggta tcacc                  1665
```

<210> SEQ ID NO 14
<211> LENGTH: 551
<212> TYPE: PRT
<213> ORGANISM: Artificial Sequence
<220> FEATURE:
<223> OTHER INFORMATION: Synthetic Polypeptide

<400> SEQUENCE: 14

```
Met Glu Glu Asp Asn Met Ala Ile Ile Lys Glu Phe Met Arg Phe Lys
1               5                   10                  15

Val His Met Glu Gly Ser Val Asn Gly His Glu Phe Glu Ile Glu Gly
            20                  25                  30

Glu Gly Glu Gly His Pro Tyr Glu Gly Thr Gln Thr Ala Lys Leu Lys
        35                  40                  45

Val Thr Lys Gly Gly Pro Leu Pro Phe Ala Trp Asp Ile Leu Ser Pro
    50                  55                  60

Gln Phe Met Tyr Gly Ser Lys Ala Tyr Val Lys His Pro Ala Asp Ile
65                  70                  75                  80

Pro Asp Tyr Leu Lys Leu Ser Phe Pro Glu Gly Phe Thr Trp Glu Arg
                85                  90                  95

Val Met Asn Phe Glu Asp Gly Gly Val Val Thr Val Thr Gln Asp Ser
            100                 105                 110

Ser Leu Gln Asp Gly Glu Phe Ile Tyr Lys Val Lys Leu Leu Gly Thr
```

```
                    115                 120                 125
Asn Phe Pro Ser Asp Gly Pro Val Met Gln Lys Lys Thr Met Gly Trp
130                 135                 140

Glu Ala Ser Thr Glu Arg Met Tyr Pro Glu Asp Gly Ala Leu Lys Gly
145                 150                 155                 160

Glu Ile Asn Gln Arg Leu Lys Leu Lys Asp Gly Gly His Tyr Asp Ala
                    165                 170                 175

Glu Val Lys Thr Thr Tyr Lys Ala Lys Lys Pro Val Gln Leu Pro Gly
                180                 185                 190

Ala Tyr Asn Val Asp Ile Lys Leu Asp Ile Thr Ser His Asn Glu Asp
                195                 200                 205

Gly Gly Gly Ser Gly Gly Gly Ser Gly Gly Gly Ser Ala Ala Val Glu
210                 215                 220

Asp Asn His Leu Leu Ile Lys Ala Val Gln Asn Glu Asp Val Asp Leu
225                 230                 235                 240

Val Gln Gln Leu Leu Glu Gly Gly Ala Asn Val Asn Phe Gln Glu Glu
                245                 250                 255

Glu Gly Gly Trp Thr Pro Leu His Asn Ala Val Gln Met Ser Arg Glu
                260                 265                 270

Asp Ile Val Glu Leu Leu Arg His Gly Ala Asp Pro Val Leu Arg
                275                 280                 285

Lys Lys Asn Gly Ala Thr Pro Phe Ile Leu Ala Ala Ile Ala Gly Ser
290                 295                 300

Val Lys Leu Leu Lys Leu Phe Leu Ser Lys Gly Ala Asp Val Asn Glu
305                 310                 315                 320

Cys Asp Phe Tyr Gly Phe Thr Ala Phe Met Glu Ala Ala Val Tyr Gly
                325                 330                 335

Lys Val Lys Ala Leu Lys Phe Leu Tyr Lys Arg Gly Ala Asn Val Asn
                340                 345                 350

Leu Arg Arg Lys Thr Lys Glu Asp Gln Glu Arg Leu Arg Lys Gly Gly
                355                 360                 365

Ala Thr Ala Leu Met Asp Ala Ala Glu Lys Gly His Val Glu Val Leu
                370                 375                 380

Lys Ile Leu Leu Asp Glu Met Gly Ala Asp Val Asn Ala Cys Asp Asn
385                 390                 395                 400

Met Gly Arg Asn Ala Leu Ile His Ala Leu Leu Ser Ser Asp Asp Ser
                    405                 410                 415

Asp Val Glu Ala Ile Thr His Leu Leu Leu Asp His Gly Ala Asp Val
                420                 425                 430

Asn Val Arg Gly Glu Arg Gly Lys Thr Pro Leu Ile Leu Ala Val Glu
                435                 440                 445

Lys Lys His Leu Gly Leu Val Gln Arg Leu Leu Glu Gln Glu His Ile
                450                 455                 460

Glu Ile Asn Asp Thr Asp Ser Asp Gly Lys Thr Ala Leu Leu Leu Ala
465                 470                 475                 480

Val Glu Leu Lys Leu Lys Lys Ile Ala Glu Leu Leu Cys Lys Arg Gly
                    485                 490                 495

Ala Ser Thr Asp Cys Gly Asp Leu Val Met Thr Ala Arg Arg Asn Tyr
                500                 505                 510

Asp His Ser Leu Val Lys Val Leu Leu Ser His Gly Ala Gly Gly Gly
                515                 520                 525

Ser Gly Gly Gly Ser Tyr Thr Ile Val Glu Gln Tyr Glu Arg Ala Glu
530                 535                 540
```

Gly Arg His Ser Thr Gly Gly
545             550

<210> SEQ ID NO 15
<211> LENGTH: 1653
<212> TYPE: DNA
<213> ORGANISM: Artificial Sequence
<220> FEATURE:
<223> OTHER INFORMATION: Synthetic Polynucleotide

<400> SEQUENCE: 15

| | |
|---|---|
| atggaggagg acaacatggc catcatcaag gagttcatga gattcaaggt gcacatggag | 60 |
| ggcagcgtga acggccacga gttcgagatc gagggcgagg gcgagggcca ccctacgag | 120 |
| ggcacccaga ccgccaagct gaaggtgacc aagggcggcc ccctgccctt cgcctgggac | 180 |
| atcctgagcc cccagttcat gtacggcagc aaggcctacg tgaagcaccc cgccgacatc | 240 |
| cccgactacc tgaagctgag cttccccgag ggcttcacct gggagagagt gatgaacttc | 300 |
| gaggacggcg gcgtggtgac cgtgacccag gacagcagcc tgcaggacgg cgagttcatc | 360 |
| tacaaggtga agctgctggg caccaacttc cccagcgacg gccccgtgat gcagaagaag | 420 |
| accatgggct gggaggccag caccgagaga atgtaccccg aggacggcgc cctgaagggc | 480 |
| gagatcaacc agagactgaa gctgaaggac ggcggccact acgacgccga ggtgaagacc | 540 |
| acctacaagg ccaagaagcc cgtgcagctg cccggcgcct acaacgtgga catcaagctg | 600 |
| gacatcacca gccacaacga ggacggaggc ggatccggag aggctccgg cggcggctcc | 660 |
| gctgctgtcg aagacaacca cctcctgatc aaagccgtgc aaaacgagga cgtcgatctc | 720 |
| gtccaacaac tcctcgaagg cggcgctaac gtcaattttc aagaggagga gggcggctgg | 780 |
| accccctctcc ataacgccgt gcaaatgagc agggaagaca ttgtggagct cctcctcagg | 840 |
| catggagctg accctgtcct cagaaagaag aacggagcca ccccctttat cctggccgcc | 900 |
| attgctggct ccgtcaagct cctcaagctc ttcctgagca aaggcgccga cgtcaatgag | 960 |
| tgcgacttct acggattcac agcctttatg gaagccgctg tgtacggcaa ggtgaaggcc | 1020 |
| ctgaagttcc tctacaaaag gggcgccaac gtgaacctga aggaaaaac caaggaggat | 1080 |
| caggagagac tgaggaaagg cggagctacc gccctcatgg atgctgccga aagggccac | 1140 |
| gtggaagtcc tgaagatcct cctcgacgaa atgggcgctg acgtgaacgc ttgcgacaac | 1200 |
| atgggaagga atgctctgat ccacgctctc ctcagcagcg acgactccga cgtggaagct | 1260 |
| atcacccacc tcctcctgga tcacggcgcc gatgtcaacg tcagaggaga agaggaaag | 1320 |
| acccccctca tcctggctgt ggagaaaaag catctcggac tcgtgcagag actgctggag | 1380 |
| caagagcaca tcgagatcaa tgacaccgat agcgacggca aaaccgctct cctcctcgcc | 1440 |
| gtggagctga agctgaagaa gatcgctgag ctgctctgta aaagaggcgc tagcacagac | 1500 |
| tgcggagacc tggtcatgac agccagaagg aactacgacc actccctggt gaaagtcctc | 1560 |
| ctcagccatg gagctggcgg aggaagcggc ggaggctcct acaccatcgt ggagcagtac | 1620 |
| gagagagccg agggcagaca cagcaccggc ggc | 1653 |

<210> SEQ ID NO 16
<211> LENGTH: 875
<212> TYPE: PRT
<213> ORGANISM: Artificial Sequence
<220> FEATURE:
<223> OTHER INFORMATION: Synthetic Polypeptide

<400> SEQUENCE: 16

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
            20                  25                  30

Tyr Ala Leu Val Pro Gly Thr Ile Ala Phe Thr Asp Ala His Ile Glu
        35                  40                  45

Val Asp Ile Thr Tyr Ala Glu Tyr Phe Glu Met Ser Val Arg Leu Ala
    50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
            115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
            195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
    275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
305                 310                 315                 320

Lys Glu Val Gly Glu Ala Val Ala Lys Arg Phe His Leu Pro Gly Ile
                325                 330                 335

Arg Gln Gly Tyr Gly Leu Thr Glu Thr Thr Ser Ala Ile Leu Ile Thr
            340                 345                 350

Pro Glu Gly Asp Asp Lys Pro Gly Ala Val Gly Lys Val Val Pro Phe
            355                 360                 365

Phe Glu Ala Lys Val Val Asp Leu Asp Thr Gly Lys Thr Leu Gly Val
    370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415
```

-continued

Gly Gly Gly Ser Gly Gly Ser Gly Gly Ser Ala Ala Val Glu
            420             425             430

Asp Asn His Leu Leu Ile Lys Ala Val Gln Asn Glu Asp Val Asp Leu
            435             440             445

Val Gln Gln Leu Leu Glu Gly Gly Ala Asn Val Asn Phe Gln Glu Glu
        450             455             460

Glu Gly Gly Trp Thr Pro Leu His Asn Ala Val Gln Met Ser Arg Glu
465             470             475             480

Asp Ile Val Glu Leu Leu Arg His Gly Ala Asp Pro Val Leu Arg
            485             490             495

Lys Lys Asn Gly Ala Thr Pro Phe Ile Leu Ala Ala Ile Ala Gly Ser
            500             505             510

Val Lys Leu Leu Lys Leu Phe Leu Ser Lys Gly Ala Asp Val Asn Glu
        515             520             525

Cys Asp Phe Tyr Gly Phe Thr Ala Phe Met Glu Ala Ala Val Tyr Gly
        530             535             540

Lys Val Lys Ala Leu Lys Phe Leu Tyr Lys Arg Gly Ala Asn Val Asn
545             550             555             560

Leu Arg Arg Lys Thr Lys Glu Asp Gln Glu Arg Leu Arg Lys Gly Gly
            565             570             575

Ala Thr Ala Leu Met Asp Ala Ala Glu Lys Gly His Val Glu Val Leu
            580             585             590

Lys Ile Leu Leu Asp Glu Met Gly Ala Asp Val Asn Ala Cys Asp Asn
        595             600             605

Met Gly Arg Asn Ala Leu Ile His Ala Leu Leu Ser Ser Asp Asp Ser
610             615             620

Asp Val Glu Ala Ile Thr His Leu Leu Leu Asp His Gly Ala Asp Val
625             630             635             640

Asn Val Arg Gly Glu Arg Gly Lys Thr Pro Leu Ile Leu Ala Val Glu
            645             650             655

Lys Lys His Leu Gly Leu Val Gln Arg Leu Leu Glu Gln Glu His Ile
            660             665             670

Glu Ile Asn Asp Thr Asp Ser Asp Gly Lys Thr Ala Leu Leu Leu Ala
        675             680             685

Val Glu Leu Lys Leu Lys Lys Ile Ala Glu Leu Leu Cys Lys Arg Gly
        690             695             700

Ala Ser Thr Asp Cys Gly Asp Leu Val Met Thr Ala Arg Arg Asn Tyr
705             710             715             720

Asp His Ser Leu Val Lys Val Leu Leu Ser His Gly Ala Gly Gly Gly
            725             730             735

Ser Gly Gly Gly Ser Trp Leu His Ser Gly Asp Ile Ala Tyr Trp Asp
            740             745             750

Glu Asp Glu His Phe Phe Ile Val Asp Arg Leu Lys Ser Leu Ile Lys
        755             760             765

Tyr Lys Gly Tyr Gln Val Ala Pro Ala Glu Leu Glu Ser Ile Leu Leu
        770             775             780

Gln His Pro Asn Ile Phe Asp Ala Gly Val Ala Gly Leu Pro Asp Asp
785             790             795             800

Asp Ala Gly Glu Leu Pro Ala Ala Val Val Val Leu Glu His Gly Lys
            805             810             815

Thr Met Thr Glu Lys Glu Ile Val Asp Tyr Val Ala Ser Gln Val Thr
            820             825             830

Thr Ala Lys Lys Leu Arg Gly Gly Val Val Phe Val Asp Glu Val Pro

```
                835                 840                 845
Lys Gly Leu Thr Gly Lys Leu Asp Ala Arg Lys Ile Arg Glu Ile Leu
            850                 855                 860

Ile Lys Ala Lys Lys Gly Gly Lys Ile Ala Val
865                 870                 875

<210> SEQ ID NO 17
<211> LENGTH: 2628
<212> TYPE: DNA
<213> ORGANISM: Artificial Sequence
<220> FEATURE:
<223> OTHER INFORMATION: Synthetic Polynucleotide

<400> SEQUENCE: 17
atggaagacg ctaaaaacat caagaagggc cccgctcctt tctatcctct ggaggacggc      60
accgccggcg aacaactcca taaagccatg aagaggtatg ctctggtgcc tggaaccatt     120
gccttcacag acgcccacat cgaagtggac atcacctacg ccgagtattt cgagatgtcc     180
gtcaggctcg ccgaggccat gaaaagatat ggcctgaaca caaaccacag gatcgtggtc     240
tgttccgaga cagcctcca gttcttcatg cccgtgctcg agccctcttc atcggagtg       300 gccgtggctc ccgccaatga tatctataac gagagggaac tcctgaactc catgggcatc     360
agccagccca ccgtggtgtt tgtgagcaag aagggcctgc agaaaattct caacgtccag     420
aagaaactgc ctattatcca aaagattatc attatggact ccaagaccga ctaccagggc     480
ttccagagca tgtacacctt cgtcacctcc cacctgcctc ctggcttcaa cgaatacgat     540
ttcgtgcccg agagcttcga tagggacaag acaatcgccc tcatcatgaa tagcagcgga     600
tccaccggac tccctaaagg cgtggccctc cctcatagaa ccgcctgtgt gagattcagc     660
cacgctaggg atcccatttt cggcaaccag atcatccctg acaccgccat cctgtccgtg     720
gtgcccttcc accatggatt cggaatgttc accacactcg gctacctgat ctgcggcttt     780
agggtcgtgc tgatgtacag gttcgaggag gagctctttc tcaggtccct gcaagactac     840
aagatccaga gcgctctcct ggtgcccacc ctgtttagct ttttcgccaa gtccacccttg    900 attgacaagt acgatctctc caacctgcac gagattgcct ccggaggagc ccccctgtcc     960
aaggaagtcg agaagctgtg gctaaaaggt tccacctgcc tggcattaga caggctat     1020 ggcctcaccg aaaccaccag cgccattctg atcacacccg aaggcgatga taagcctgga    1080
gccgtcggca aggtggtgcc ctttttcgag gccaaagtgg tggacctgga taccggaaag    1140
accctgggcg tgaatcagag gggcgaactg tgcgtcaggg gacctatgat catgtccggc    1200
tatgtcaaca cccccgaggc cacaaacgct ctgatcgata aggatggagg aggcggatcc    1260
ggaggaggct ccggcggcgg ctccgctgct gtcgaagaca accacctcct gatcaaagcc    1320
gtgcaaaacg aggacgtcga tctcgtccaa caactcctcg aaggcggcgc taacgtcaat    1380
tttcaagagg aggagggcgg ctggaccccct ctccataacg ccgtgcaaat gagcagggaa    1440
gacattgtgg agctcctcct caggcatgga gctgaccctg tcctcagaaa agaacgga     1500 gccacccccct ttatcctggc cgccattgct ggctccgtca agctcctcaa gctcttcctg    1560
agcaaaggcg ccgacgtcaa tgagtgcgac ttctacggat tcacagcctt tatggaagcc    1620
gctgtgtacg gcaaggtgaa ggccctgaag ttcctctaca aaaggggcgc caacgtgaac    1680
ctgagaagga aaaccaagga ggatcaggag agactgagga aaggcggagc taccgccctc    1740
atggatgctg ccgaaaaggg ccacgtgaa gtcctgaaga tcctcctcga cgaaatgggc    1800
gctgacgtga acgcttgcga caacatggga aggaatgctc tgatccacgc tctcctcagc    1860
```

```
agcgacgact ccgacgtgga agctatcacc cacctcctcc tggatcacgg cgccgatgtc   1920
aacgtcagag gagaaagagg aaagacccce ctcatcctgg ctgtggagaa aaagcatctc   1980
ggactcgtgc agagactgct ggagcaagag cacatcgaga tcaatgacac cgatagcgac   2040
ggcaaaaccg ctctcctcct cgccgtggag ctgaagctga agaagatcgc tgagctgctc   2100
tgtaaaagag gcgctagcac agactgcgga gacctggtca tgacagccag aaggaactac   2160
gaccactccc tggtgaaagt cctcctcagc catgggagctg gcggaggaag cggcggaggc   2220
tcctggctcc attccggaga catcgcctac tgggacgagg atgagcactt tttcatcgtc   2280
gacagactca gtccctgat caagtacaag ggataccaag tcgctcccgc tgaactggaa   2340
tccatcctcc tccagcaccc taacatcttc gacgctggcg tggctggcct ccctgacgat   2400
gacgctggcg aactgcctgc cgctgtcgtc gtcctcgaac acggcaagac catgaccgag   2460
aaggagatcg tggactacgt ggctagccag gtcaccacag ccaaaaaact gaggggagga   2520
gtggtgttcg tcgacgaagt gcccaaggga ctgaccggca aactggacgc caggaaaatt   2580
agggagatcc tgatcaaggc caagaaaggc ggaaagatcg ccgtgtga                2628
```

<210> SEQ ID NO 18
<211> LENGTH: 741
<212> TYPE: PRT
<213> ORGANISM: Homo Sapiens

<400> SEQUENCE: 18

```
Met Glu Ser Arg Asp His Asn Asn Pro Gln Glu Gly Pro Thr Ser Ser
1               5                   10                  15

Ser Gly Arg Arg Ala Ala Val Glu Asp Asn His Leu Leu Ile Lys Ala
            20                  25                  30

Val Gln Asn Glu Asp Val Asp Leu Val Gln Gln Leu Leu Glu Gly Gly
        35                  40                  45

Ala Asn Val Asn Phe Gln Glu Glu Gly Gly Trp Thr Pro Leu His
    50                  55                  60

Asn Ala Val Gln Met Ser Arg Glu Asp Ile Val Glu Leu Leu Leu Arg
65                  70                  75                  80

His Gly Ala Asp Pro Val Leu Arg Lys Lys Asn Gly Ala Thr Pro Phe
                85                  90                  95

Ile Leu Ala Ala Ile Ala Gly Ser Val Lys Leu Leu Lys Leu Phe Leu
            100                 105                 110

Ser Lys Gly Ala Asp Val Asn Glu Cys Asp Phe Tyr Gly Phe Thr Ala
        115                 120                 125

Phe Met Glu Ala Ala Val Tyr Gly Lys Val Lys Ala Leu Lys Phe Leu
    130                 135                 140

Tyr Lys Arg Gly Ala Asn Val Asn Leu Arg Arg Lys Thr Lys Glu Asp
145                 150                 155                 160

Gln Glu Arg Leu Arg Lys Gly Gly Ala Thr Ala Leu Met Asp Ala Ala
                165                 170                 175

Glu Lys Gly His Val Glu Val Leu Lys Ile Leu Leu Asp Glu Met Gly
            180                 185                 190

Ala Asp Val Asn Ala Cys Asp Asn Met Gly Arg Asn Ala Leu Ile His
        195                 200                 205

Ala Leu Leu Ser Ser Asp Asp Ser Asp Val Glu Ala Ile Thr His Leu
    210                 215                 220

Leu Leu Asp His Gly Ala Asp Val Asn Val Arg Gly Glu Arg Gly Lys
225                 230                 235                 240
```

```
Thr Pro Leu Ile Leu Ala Val Glu Lys Lys His Leu Gly Leu Val Gln
                245                 250                 255

Arg Leu Leu Glu Gln Glu His Ile Glu Ile Asn Asp Thr Asp Ser Asp
            260                 265                 270

Gly Lys Thr Ala Leu Leu Leu Ala Val Glu Leu Lys Leu Lys Lys Ile
        275                 280                 285

Ala Glu Leu Leu Cys Lys Arg Gly Ala Ser Thr Asp Cys Gly Asp Leu
    290                 295                 300

Val Met Thr Ala Arg Arg Asn Tyr Asp His Ser Leu Val Lys Val Leu
305                 310                 315                 320

Leu Ser His Gly Ala Lys Glu Asp Phe His Pro Ala Glu Asp Trp
                325                 330                 335

Lys Pro Gln Ser Ser His Trp Gly Ala Ala Leu Lys Asp Leu His Arg
            340                 345                 350

Ile Tyr Arg Pro Met Ile Gly Lys Leu Lys Phe Phe Ile Asp Glu Lys
        355                 360                 365

Tyr Lys Ile Ala Asp Thr Ser Glu Gly Gly Ile Tyr Leu Gly Phe Tyr
    370                 375                 380

Glu Lys Gln Glu Val Ala Val Lys Thr Phe Cys Glu Gly Ser Pro Arg
385                 390                 395                 400

Ala Gln Arg Glu Val Ser Cys Leu Gln Ser Ser Arg Glu Asn Ser His
                405                 410                 415

Leu Val Thr Phe Tyr Gly Ser Glu Ser His Arg Gly His Leu Phe Val
            420                 425                 430

Cys Val Thr Leu Cys Glu Gln Thr Leu Glu Ala Cys Leu Asp Val His
        435                 440                 445

Arg Gly Glu Asp Val Glu Asn Glu Glu Asp Glu Phe Ala Arg Asn Val
    450                 455                 460

Leu Ser Ser Ile Phe Lys Ala Val Gln Glu Leu His Leu Ser Cys Gly
465                 470                 475                 480

Tyr Thr His Gln Asp Leu Gln Pro Gln Asn Ile Leu Ile Asp Ser Lys
                485                 490                 495

Lys Ala Ala His Leu Ala Asp Phe Asp Lys Ser Ile Lys Trp Ala Gly
            500                 505                 510

Asp Pro Gln Glu Val Lys Arg Asp Leu Glu Asp Leu Gly Arg Leu Val
        515                 520                 525

Leu Tyr Val Val Lys Lys Gly Ser Ile Ser Phe Glu Asp Leu Lys Ala
    530                 535                 540

Gln Ser Asn Glu Glu Val Val Gln Leu Ser Pro Asp Glu Glu Thr Lys
545                 550                 555                 560

Asp Leu Ile His Arg Leu Phe His Pro Gly Glu His Val Arg Asp Cys
                565                 570                 575

Leu Ser Asp Leu Leu Gly His Pro Phe Phe Trp Thr Trp Glu Ser Arg
            580                 585                 590

Tyr Arg Thr Leu Arg Asn Val Gly Asn Glu Ser Asp Ile Lys Thr Arg
        595                 600                 605

Lys Ser Glu Ser Glu Ile Leu Arg Leu Leu Gln Pro Gly Pro Ser Glu
    610                 615                 620

His Ser Lys Ser Phe Asp Lys Trp Thr Thr Lys Ile Asn Glu Cys Val
625                 630                 635                 640

Met Lys Lys Met Asn Lys Phe Tyr Glu Lys Arg Gly Asn Phe Tyr Gln
                645                 650                 655
```

-continued

```
Asn Thr Val Gly Asp Leu Leu Lys Phe Ile Arg Asn Leu Gly Glu His
                660                 665                 670

Ile Asp Glu Glu Lys His Lys Met Lys Leu Lys Ile Gly Asp Pro
            675                 680                 685

Ser Leu Tyr Phe Gln Lys Thr Phe Pro Asp Leu Val Ile Tyr Val Tyr
        690                 695                 700

Thr Lys Leu Gln Asn Thr Glu Tyr Arg Lys His Phe Pro Gln Thr His
705                 710                 715                 720

Ser Pro Asn Lys Pro Gln Cys Asp Gly Ala Gly Gly Ala Ser Gly Leu
                725                 730                 735

Ala Ser Pro Gly Cys
            740

<210> SEQ ID NO 19
<211> LENGTH: 735
<212> TYPE: PRT
<213> ORGANISM: Mus Musculus

<400> SEQUENCE: 19

Met Glu Thr Pro Asp Tyr Asn Thr Pro Gln Gly Gly Thr Pro Ser Ala
1               5                   10                  15

Gly Ser Gln Arg Thr Val Val Glu Asp Asp Ser Ser Leu Ile Lys Ala
            20                  25                  30

Val Gln Lys Gly Asp Val Val Arg Val Gln Gln Leu Leu Glu Lys Gly
        35                  40                  45

Ala Asp Ala Asn Ala Cys Glu Asp Thr Trp Gly Trp Thr Pro Leu His
    50                  55                  60

Asn Ala Val Gln Ala Gly Arg Val Asp Ile Val Asn Leu Leu Leu Ser
65                  70                  75                  80

His Gly Ala Asp Pro His Arg Arg Lys Lys Asn Gly Ala Thr Pro Phe
                85                  90                  95

Ile Ile Ala Gly Ile Gln Gly Asp Val Lys Leu Leu Glu Ile Leu Leu
            100                 105                 110

Ser Cys Gly Ala Asp Val Asn Glu Cys Asp Glu Asn Gly Phe Thr Ala
        115                 120                 125

Phe Met Glu Ala Ala Glu Arg Gly Asn Ala Glu Ala Leu Arg Phe Leu
    130                 135                 140

Phe Ala Lys Gly Ala Asn Val Asn Leu Arg Arg Gln Thr Thr Lys Asp
145                 150                 155                 160

Lys Arg Arg Leu Lys Gln Gly Gly Ala Thr Ala Leu Met Ser Ala Ala
                165                 170                 175

Glu Lys Gly His Leu Glu Val Leu Arg Ile Leu Leu Asn Asp Met Lys
            180                 185                 190

Ala Glu Val Asp Ala Arg Asp Asn Met Gly Arg Asn Ala Leu Ile Arg
        195                 200                 205

Thr Leu Leu Asn Trp Asp Cys Glu Asn Val Glu Glu Ile Thr Ser Ile
    210                 215                 220

Leu Ile Gln His Gly Ala Asp Val Asn Val Arg Gly Glu Arg Gly Lys
225                 230                 235                 240

Thr Pro Leu Ile Ala Ala Val Glu Arg Lys His Thr Gly Leu Val Gln
                245                 250                 255

Met Leu Leu Ser Arg Glu Gly Ile Asn Ile Asp Ala Arg Asp Asn Glu
            260                 265                 270

Gly Lys Thr Ala Leu Leu Ile Ala Val Asp Lys Gln Leu Lys Glu Ile
        275                 280                 285
```

```
Val Gln Leu Leu Leu Glu Lys Gly Ala Asp Lys Cys Asp Asp Leu Val
    290                 295                 300

Trp Ile Ala Arg Arg Asn His Asp Tyr His Leu Val Lys Leu Leu Leu
305                 310                 315                 320

Pro Tyr Val Ala Asn Pro Asp Thr Asp Pro Ala Gly Asp Trp Ser
                325                 330                 335

Pro His Ser Ser Arg Trp Gly Thr Ala Leu Lys Ser Leu His Ser Met
                340                 345                 350

Thr Arg Pro Met Ile Gly Lys Leu Lys Ile Phe Ile His Asp Asp Tyr
            355                 360                 365

Lys Ile Ala Gly Thr Ser Glu Gly Ala Val Tyr Leu Gly Ile Tyr Asp
    370                 375                 380

Asn Arg Glu Val Ala Val Lys Val Phe Arg Glu Asn Ser Pro Arg Gly
385                 390                 395                 400

Cys Lys Glu Val Ser Cys Leu Arg Asp Cys Gly Asp His Ser Asn Leu
                405                 410                 415

Val Ala Phe Tyr Gly Arg Glu Asp Asp Lys Gly Cys Leu Tyr Val Cys
            420                 425                 430

Val Ser Leu Cys Glu Trp Thr Leu Glu Glu Phe Leu Arg Leu Pro Arg
    435                 440                 445

Glu Glu Pro Val Glu Asn Gly Glu Asp Lys Phe Ala His Ser Ile Leu
450                 455                 460

Leu Ser Ile Phe Glu Gly Val Gln Lys Leu His Leu His Gly Tyr Ser
465                 470                 475                 480

His Gln Asp Leu Gln Pro Gln Asn Ile Leu Ile Asp Ser Lys Lys Ala
                485                 490                 495

Val Arg Leu Ala Asp Phe Asp Gln Ser Ile Arg Trp Met Gly Glu Ser
            500                 505                 510

Gln Met Val Arg Arg Asp Leu Glu Asp Leu Gly Arg Leu Val Leu Tyr
            515                 520                 525

Val Val Met Lys Gly Glu Ile Pro Phe Glu Thr Leu Lys Thr Gln Asn
    530                 535                 540

Asp Glu Val Leu Leu Thr Met Ser Pro Asp Glu Glu Thr Lys Asp Leu
545                 550                 555                 560

Ile His Cys Leu Phe Ser Pro Gly Glu Asn Val Lys Asn Cys Leu Val
                565                 570                 575

Asp Leu Leu Gly His Pro Phe Phe Trp Thr Trp Glu Asn Arg Tyr Arg
            580                 585                 590

Thr Leu Arg Asn Val Gly Asn Glu Ser Asp Ile Lys Val Arg Lys Cys
            595                 600                 605

Lys Ser Asp Leu Leu Arg Leu Leu Gln His Gln Thr Leu Glu Pro Pro
    610                 615                 620

Arg Ser Phe Asp Gln Trp Thr Ser Lys Ile Asp Lys Asn Val Met Asp
625                 630                 635                 640

Glu Met Asn His Phe Tyr Glu Lys Arg Lys Asn Pro Tyr Gln Asp
                645                 650                 655

Thr Val Gly Asp Leu Leu Lys Phe Ile Arg Asn Ile Gly Glu His Ile
            660                 665                 670

Asn Glu Glu Lys Lys Arg Gly Met Lys Glu Ile Leu Gly Asp Pro Ser
    675                 680                 685

Arg Tyr Phe Gln Glu Thr Phe Pro Asp Leu Val Ile Tyr Ile Tyr Lys
    690                 695                 700
```

-continued

```
Lys Leu Lys Glu Thr Glu Tyr Arg Lys His Phe Pro Gln Pro Pro Pro
705                 710                 715                 720

Arg Leu Ser Val Pro Glu Ala Val Gly Pro Gly Gly Ile Gln Ser
            725                 730                 735

<210> SEQ ID NO 20
<211> LENGTH: 738
<212> TYPE: PRT
<213> ORGANISM: Rattus Norvegicus

<400> SEQUENCE: 20

Met Glu Thr Thr Asp His Ser Thr Pro Gln Cys Gly Ser Ala Ser Ala
1               5                   10                  15

Gly Gly Gln Lys Thr Val Gly Lys Asp Asp Tyr Leu Leu Ile Glu Ala
            20                  25                  30

Val Asn Lys Gly Asp Ala Asp Arg Val Gln Gln Leu Leu Glu Gln Gly
        35                  40                  45

Ala Asp Ala Asn Val Cys Glu Glu Ser Gly Gly Trp Thr Pro Leu His
    50                  55                  60

Asn Ala Val Gln Ser Gly Arg Val Asp Ile Val Asn Leu Leu Leu Arg
65                  70                  75                  80

Tyr Gly Ala Asp Pro His Arg Arg Lys Lys Asn Gly Ala Thr Pro Phe
                85                  90                  95

Ile Val Ala Gly Ile Cys Gly Asp Val Ser Leu Leu Gln Ile Phe Leu
            100                 105                 110

Ser Arg Gly Ala Asn Ile Asn Glu Arg Asp Met Tyr Gly Phe Thr Ala
        115                 120                 125

Phe Met Glu Ala Ala Glu Tyr Gly Asn Val Glu Ala Leu Lys Phe Leu
    130                 135                 140

Phe Ala Glu Gly Ala Asp Val Asn Leu Arg Arg Glu Thr Thr Glu Asp
145                 150                 155                 160

Arg Arg Arg Leu Lys Gln Gly Gly Ala Thr Ala Leu Met Ser Ala Ala
                165                 170                 175

Glu Asn Gly His Pro Glu Val Val Arg Ile Leu Leu Asp Glu Met Lys
            180                 185                 190

Ala Glu Ala Asp Ala Arg Asp Asn Met Gly Arg Asn Ala Leu Ile Arg
        195                 200                 205

Ser Leu Leu Asn Arg Asp Cys Glu Asn Val Glu Ile His Val Glu Glu
    210                 215                 220

Ile Thr Ser Val Leu Ile Gln Tyr Gly Ala Asp Ile Asn Val Arg Gly
225                 230                 235                 240

Glu Gly Glu Lys Thr Pro Leu Ile Ser Ala Val Lys Arg Lys His Thr
                245                 250                 255

Gly Leu Val Gln Met Leu Leu Ser Gln Glu Gly Ile Lys Val Asn Asp
            260                 265                 270

Arg Asp Ser Glu Gly Lys Thr Ala Leu Gln Ile Ala Val Glu Leu Lys
        275                 280                 285

Leu Lys Glu Ile Val Arg Leu Leu Glu Lys Gly Ala Asp Thr Lys
    290                 295                 300

Cys Gly Asp Leu Val Trp Ile Ala Lys Arg Asn Tyr Asp His Gly Leu
305                 310                 315                 320

Val Lys Leu Leu Leu Ser Tyr Glu Ala Asn His Asp Thr Asn Pro Pro
                325                 330                 335

Ala Lys Asp Trp Leu Pro His Ser Ala Arg Trp Gly Glu Ala Leu Glu
            340                 345                 350
```

Arg Leu His Ser Val Ser Arg Pro Met Thr Gly Lys Leu Lys Ile Phe
            355                 360                 365

Met Asn Asp Asp Tyr Lys Ile Ala Ser Thr Ser Glu Gly Gly Ile Tyr
        370                 375                 380

Leu Gly Ile Tyr Asp Asn Arg Glu Val Ala Val Lys Val Phe Cys Glu
385                 390                 395                 400

Asn Ser Ser Arg Gly Arg Lys Glu Val Ser Cys Leu Arg Asp Cys Gly
                405                 410                 415

Asp His Ser Asn Leu Leu Thr Phe Tyr Gly Ser Glu Glu His Lys Gly
            420                 425                 430

Ser Leu Tyr Val Cys Val Ser Leu Cys Glu Ser Thr Leu Glu Lys Phe
        435                 440                 445

Leu Asn Val Pro Arg Glu Glu Pro Met Glu Lys Gly Glu Asp Lys Phe
    450                 455                 460

Ala Leu Ser Val Leu Leu Ser Ile Phe Lys Gly Val Gln Lys Leu His
465                 470                 475                 480

Met His Gly Tyr Ser His Gln Asn Leu Gln Pro Pro Asn Ile Leu Ile
                485                 490                 495

Asp Ser Glu Lys Ala Val Arg Leu Ala Asp Phe Asp Gly Ser Ile Gln
            500                 505                 510

Trp Met Arg Glu Ser Gln Thr Val Gln Arg Asp Leu Glu Asp Leu Gly
        515                 520                 525

Arg Leu Val Leu Tyr Val Val Asn Lys Gly Glu Ile Pro Phe Glu Thr
    530                 535                 540

Leu Lys Gly Gln Asn Asp Glu Glu Leu Leu Thr Ile Ala Pro Asn Glu
545                 550                 555                 560

Glu Thr Lys Asp Leu Val His Cys Leu Phe Ser Pro Gly Glu Asn Val
                565                 570                 575

Lys Asn Cys Leu Met Asp Leu Leu Gly His Pro Phe Phe Trp Thr Trp
            580                 585                 590

Glu Asn Arg Tyr Arg Thr Leu Arg Asp Val Gly Asn Glu Ser Asp Ile
        595                 600                 605

Lys Val Arg Asn Asn Lys Ser Lys Leu Leu Lys Leu Leu Gln Pro Gln
    610                 615                 620

Thr His Ala Pro Ser Arg Ser Phe Asp Arg Trp Thr Ser Lys Ile Asp
625                 630                 635                 640

Lys Arg Val Met Ser Asp Met Asn Gly Phe Tyr Lys Ser Arg Lys Gly
                645                 650                 655

Tyr Arg Asp Thr Val Gly Asp Leu Leu Lys Phe Ile Arg Asn Ile Gly
            660                 665                 670

Glu His Ile Asn Glu Glu Lys Asn Arg Gln Met Lys Glu Ile Leu Gly
        675                 680                 685

Asp Pro Ser Arg Tyr Phe Gln Glu Thr Phe Pro Asp Leu Val Ile Tyr
    690                 695                 700

Ile Tyr Lys Lys Leu Lys Glu Thr Glu Phe Arg Lys His Phe Pro Gln
705                 710                 715                 720

Pro Pro Pro Ser Leu Ser Val Pro Glu Ala Ala Gly Pro Gly Gly Val
                725                 730                 735

Gln Ser

<210> SEQ ID NO 21
<211> LENGTH: 325
<212> TYPE: PRT

<213> ORGANISM: Pan troglodytes

<400> SEQUENCE: 21

Met Glu Thr Arg Asp His Asn Asn Pro Gln Glu Gly Pro Thr Ser Ser
1               5                   10                  15

Ser Gly Arg Arg Ala Ala Val Glu Asp Asn His Ser Leu Ile Lys Ala
            20                  25                  30

Val Gln Asn Gly Asp Val Asp Gln Val Gln Gln Leu Leu Glu Asp Gly
        35                  40                  45

Ala Asn Val Asn Phe Gln Glu Glu Gly Gly Trp Thr Pro Leu His
    50                  55                  60

Asn Ala Val Gln Met Ser Lys Glu Glu Ile Val Glu Leu Leu Leu Arg
65                  70                  75                  80

His Gly Ala Asp Pro Val Leu Arg Lys Lys Asn Gly Ala Thr Pro Phe
                85                  90                  95

Ile Leu Ala Ala Ile Ala Gly Ser Val Lys Leu Leu Glu Leu Phe Leu
            100                 105                 110

Ser Lys Gly Ala Asp Val Asn Glu Cys Asp Phe Tyr Gly Phe Thr Ala
        115                 120                 125

Phe Met Glu Ala Ala Val Tyr Gly Lys Val Glu Ala Leu Lys Phe Leu
    130                 135                 140

Tyr Lys Arg Gly Ala Asn Val Asn Leu Arg Arg Lys Thr Lys Glu Asp
145                 150                 155                 160

Gln Glu Arg Leu Arg Lys Gly Gly Ala Thr Ala Leu Met Asp Ala Ala
                165                 170                 175

Glu Glu Gly His Val Glu Val Leu Lys Ile Leu Leu Asp Glu Met Gly
            180                 185                 190

Ala Asp Val Asn Ala Cys Asp Asn Met Gly Arg Asn Ala Leu Ile His
        195                 200                 205

Ala Leu Leu Ser Ser His Asp Arg Asp Val Glu Ala Ile Thr Tyr Leu
    210                 215                 220

Leu Leu Asp His Gly Ala Asp Val Asn Val Arg Gly Glu Arg Gly Lys
225                 230                 235                 240

Thr Pro Leu Ile Leu Ala Val Glu Lys Lys His Leu Gly Leu Val Gln
                245                 250                 255

Arg Leu Leu Glu Gln Glu His Ile Glu Ile Asn Asp Thr Asp Ser Asp
            260                 265                 270

Gly Lys Thr Ala Leu Leu Leu Ala Val Glu Leu Lys Leu Lys Glu Ile
        275                 280                 285

Ala Glu Leu Leu Cys Lys Arg Gly Ala Ser Thr Asp Cys Gly Asp Leu
    290                 295                 300

Val Met Thr Ala Arg Arg Asn Tyr Asp His Ser Leu Val Lys Leu Leu
305                 310                 315                 320

Leu Ser His Gly Ala
                325

<210> SEQ ID NO 22
<211> LENGTH: 741
<212> TYPE: PRT
<213> ORGANISM: Pan troglodytes

<400> SEQUENCE: 22

Met Glu Thr Arg Asp His Asn Asn Pro Gln Glu Gly Pro Thr Ser Ser
1               5                   10                  15

Ser Gly Arg Arg Ala Ala Val Glu Asp Asn His Ser Leu Ile Lys Ala

-continued

```
                    20                  25                  30
Val Gln Asn Gly Asp Val Asp Gln Val Gln Gln Leu Leu Glu Asp Gly
                35                  40                  45
Ala Asn Val Asn Phe Gln Glu Glu Gly Gly Trp Thr Pro Leu His
    50                  55                  60
Asn Ala Val Gln Met Ser Lys Glu Glu Ile Val Glu Leu Leu Leu Arg
65                  70                  75                  80
His Gly Ala Asp Pro Val Leu Arg Lys Lys Asn Gly Ala Thr Pro Phe
                85                  90                  95
Ile Leu Ala Ala Ile Ala Gly Ser Val Lys Leu Leu Glu Leu Phe Leu
                100                 105                 110
Ser Lys Gly Ala Asp Val Asn Glu Cys Asp Phe Tyr Gly Phe Thr Ala
                115                 120                 125
Phe Met Glu Ala Ala Val Tyr Gly Lys Val Glu Ala Leu Lys Phe Leu
                130                 135                 140
Tyr Lys Arg Gly Ala Asn Val Asn Leu Arg Arg Lys Thr Lys Glu Asp
145                 150                 155                 160
Gln Glu Arg Leu Arg Lys Gly Gly Ala Thr Ala Leu Met Asp Ala Ala
                165                 170                 175
Glu Glu Gly His Val Glu Val Leu Lys Ile Leu Leu Asp Glu Met Gly
                180                 185                 190
Ala Asp Val Asn Ala Cys Asp Asn Met Gly Arg Asn Ala Leu Ile His
                195                 200                 205
Ala Leu Leu Ser Ser His Asp Arg Asp Val Glu Ala Ile Thr Tyr Leu
                210                 215                 220
Leu Leu Asp His Gly Ala Asp Val Asn Val Arg Gly Glu Arg Gly Lys
225                 230                 235                 240
Thr Pro Leu Ile Leu Ala Val Glu Lys Lys His Leu Gly Leu Val Gln
                245                 250                 255
Arg Leu Leu Glu Gln Glu His Ile Glu Ile Asn Asp Thr Asp Ser Asp
                260                 265                 270
Gly Lys Thr Ala Leu Leu Leu Ala Val Glu Leu Lys Leu Lys Glu Ile
                275                 280                 285
Ala Glu Leu Leu Cys Lys Arg Gly Ala Ser Thr Asp Cys Gly Asp Leu
                290                 295                 300
Val Met Thr Ala Arg Arg Asn Tyr Asp His Ser Leu Val Lys Leu Leu
305                 310                 315                 320
Leu Ser His Gly Ala Lys Glu Asp Phe His Pro Pro Ala Glu Asp Trp
                325                 330                 335
Lys Pro Gln Ser Ser His Trp Gly Ala Ala Leu Lys Asp Leu His Arg
                340                 345                 350
Ile Tyr Arg Pro Met Ile Gly Lys Leu Lys Phe Phe Ile Asp Glu Lys
                355                 360                 365
Tyr Lys Ile Ala Asp Thr Ser Glu Gly Gly Ile Tyr Leu Gly Phe Tyr
                370                 375                 380
Glu Lys Gln Glu Val Ala Val Lys Thr Phe Cys Glu Gly Ser Pro Arg
385                 390                 395                 400
Ala Gln Arg Glu Val Ser Cys Leu Gln Ser Ser Arg Glu Asn Ser His
                405                 410                 415
Leu Val Thr Phe Tyr Gly Ser Glu Ser His Arg Gly His Leu Phe Val
                420                 425                 430
Cys Val Thr Leu Cys Glu Gln Thr Leu Glu Ala Cys Leu Asp Val His
                435                 440                 445
```

```
Arg Gly Glu Asp Val Glu Asn Glu Glu Asp Glu Phe Ala Arg Asn Val
            450                 455                 460

Leu Ser Ser Ile Phe Lys Ala Val Gln Glu Leu His Leu Ser Cys Gly
465                 470                 475                 480

Tyr Thr His Gln Asp Leu Gln Pro Gln Asn Ile Leu Ile Asp Ser Lys
                485                 490                 495

Lys Ala Ala His Leu Ala Asp Phe Asp Lys Ser Ile Lys Trp Ala Gly
            500                 505                 510

Asp Pro Gln Glu Val Lys Arg Asp Leu Glu Asp Leu Gly Arg Leu Val
            515                 520                 525

Leu Tyr Val Val Lys Lys Gly Ser Ile Ser Phe Glu Glu Leu Lys Ala
530                 535                 540

Gln Ser Asn Glu Lys Val Val Gln Leu Ser Pro Asp Glu Glu Thr Lys
545                 550                 555                 560

Asp Leu Ile His His Leu Phe His Pro Gly Glu His Val Arg Asp Cys
                565                 570                 575

Leu Ser Asp Leu Leu Gly His Pro Phe Phe Trp Thr Trp Glu Ser Arg
            580                 585                 590

Tyr Arg Thr Leu Arg Asn Val Gly Asn Glu Ser Asp Ile Lys Thr Arg
            595                 600                 605

Lys Ser Glu Ser Glu Ile Leu Arg Leu Leu Gln Pro Gly Pro Ser Glu
610                 615                 620

His Ser Lys Ser Phe Asp Lys Trp Thr Thr Lys Ile Asn Glu Cys Val
625                 630                 635                 640

Met Lys Lys Met Asn Lys Phe Tyr Glu Lys Arg Gly Asn Phe Tyr Gln
                645                 650                 655

Asn Thr Val Gly Asp Leu Leu Lys Phe Ile Arg Asn Leu Gly Glu His
            660                 665                 670

Ile Asp Glu Glu Lys His Lys Lys Met Lys Leu Lys Ile Gly Asp Pro
            675                 680                 685

Ser Arg Tyr Phe Gln Lys Thr Phe Pro Asp Leu Val Ile Tyr Val Tyr
690                 695                 700

Thr Lys Leu Gln Asn Thr Glu Tyr Arg Lys His Phe Pro Gln Thr His
705                 710                 715                 720

Ser Pro Asn Lys Pro Gln Cys Asp Gly Ala Gly Gly Ala Cys Gly Leu
                725                 730                 735

Ala Ser Pro Gly Cys
            740

<210> SEQ ID NO 23
<211> LENGTH: 652
<212> TYPE: PRT
<213> ORGANISM: Pan troglodytes

<400> SEQUENCE: 23

Met Glu Thr Arg Asp His Asn Asn Pro Gln Glu Gly Pro Thr Ser Ser
1               5                   10                  15

Ser Gly Arg Arg Ala Ala Val Glu Asp Asn His Ser Leu Ile Lys Ala
            20                  25                  30

Val Gln Asn Gly Asp Val Asp Val Gln Gln Leu Leu Glu Asp Gly
            35                  40                  45

Ala Asn Val Asn Phe Gln Glu Glu Gly Gly Trp Thr Pro Leu His
50                  55                  60

Asn Ala Val Gln Met Ser Lys Glu Glu Ile Val Glu Leu Leu Leu Arg
```

-continued

```
                65                  70                  75                  80
His Gly Ala Asp Pro Val Leu Arg Lys Lys Asn Gly Ala Thr Pro Phe
                    85                  90                  95
Ile Leu Ala Ala Ile Ala Gly Ser Val Lys Leu Leu Glu Leu Phe Leu
                    100                 105                 110
Ser Lys Gly Ala Asp Val Asn Glu Cys Asp Phe Tyr Gly Phe Thr Ala
                    115                 120                 125
Phe Met Glu Ala Ala Val Tyr Gly Lys Val Glu Ala Leu Lys Phe Leu
            130                 135                 140
Tyr Lys Arg Gly Ala Asn Val Asn Leu Arg Arg Lys Thr Lys Glu Asp
145                 150                 155                 160
Gln Glu Arg Leu Arg Lys Gly Gly Ala Thr Ala Leu Met Asp Ala Ala
                    165                 170                 175
Glu Glu Gly His Val Glu Val Leu Lys Ile Leu Leu Asp Glu Met Gly
                    180                 185                 190
Ala Asp Val Asn Ala Cys Asp Asn Met Gly Arg Asn Ala Leu Ile His
                    195                 200                 205
Ala Leu Leu Ser Ser His Asp Arg Asp Val Glu Ala Ile Thr Tyr Leu
            210                 215                 220
Leu Leu Asp His Gly Ala Asp Val Asn Val Arg Gly Glu Arg Gly Lys
225                 230                 235                 240
Thr Pro Leu Ile Leu Ala Val Glu Lys Lys His Leu Gly Leu Val Gln
                    245                 250                 255
Arg Leu Leu Glu Gln Glu His Ile Glu Ile Asn Asp Thr Asp Ser Asp
                    260                 265                 270
Gly Lys Thr Ala Leu Leu Leu Ala Val Glu Leu Lys Leu Lys Glu Ile
                    275                 280                 285
Ala Glu Leu Leu Cys Lys Arg Gly Ala Ser Thr Asp Cys Gly Asp Leu
            290                 295                 300
Val Met Thr Ala Arg Arg Asn Tyr Asp His Ser Leu Val Lys Leu Leu
305                 310                 315                 320
Leu Ser His Gly Ala Lys Glu Asp Phe His Pro Ala Glu Asp Trp
                    325                 330                 335
Lys Pro Gln Ser Ser His Trp Gly Ala Ala Leu Lys Asp Leu His Arg
                    340                 345                 350
Ile Tyr Arg Pro Met Ile Gly Lys Leu Lys Phe Phe Ile Asp Glu Lys
                    355                 360                 365
Tyr Lys Ile Ala Asp Thr Ser Glu Gly Gly Ile Tyr Leu Gly Phe Tyr
            370                 375                 380
Glu Lys Gln Glu Val Ala Val Lys Thr Phe Cys Glu Gly Ser Pro Arg
385                 390                 395                 400
Ala Gln Arg Glu Val Ser Cys Leu Gln Ser Ser Arg Glu Asn Ser His
                    405                 410                 415
Leu Val Thr Phe Tyr Gly Ser Glu Ser His Arg Gly His Leu Phe Val
                    420                 425                 430
Cys Val Thr Leu Cys Glu Gln Thr Leu Glu Ala Cys Leu Asp Val His
                    435                 440                 445
Arg Gly Glu Asp Val Glu Asn Glu Glu Asp Glu Phe Ala Arg Asn Val
            450                 455                 460
Leu Ser Ser Ile Phe Lys Ala Val Gln Glu Leu His Leu Ser Cys Gly
465                 470                 475                 480
Tyr Thr His Gln Asp Leu Gln Pro Gln Asn Ile Leu Ile Asp Ser Lys
                    485                 490                 495
```

-continued

```
Lys Ala Ala His Leu Ala Asp Phe Asp Lys Ser Ile Lys Trp Ala Gly
            500                 505                 510

Asp Pro Gln Glu Val Lys Arg Asp Leu Glu Asp Leu Gly Arg Leu Val
        515                 520                 525

Leu Tyr Val Val Lys Lys Gly Ser Ile Ser Phe Glu Glu Leu Lys Ala
    530                 535                 540

Gln Ser Asn Glu Lys Val Val Gln Leu Ser Pro Asp Glu Glu Thr Lys
545                 550                 555                 560

Asp Leu Ile His His Leu Phe His Pro Gly Glu His Val Arg Asp Cys
                565                 570                 575

Leu Ser Asp Leu Leu Gly His Pro Phe Phe Trp Thr Trp Glu Ser Arg
            580                 585                 590

Tyr Arg Thr Leu Arg Asn Val Gly Asn Glu Ser Asp Ile Lys Thr Arg
        595                 600                 605

Lys Ser Glu Ser Glu Ile Leu Arg Leu Leu Gln Pro Gly Pro Ser Glu
    610                 615                 620

His Ser Lys Ser Phe Asp Lys Trp Thr Thr Lys Met Ser Lys Leu Arg
625                 630                 635                 640

His Arg Gln Ile Ile Phe Pro Thr Thr Gln Asn Gln
                645                 650

<210> SEQ ID NO 24
<211> LENGTH: 743
<212> TYPE: PRT
<213> ORGANISM: Sus Scrofa

<400> SEQUENCE: 24

Met Glu Thr Lys Arg His Asn Asn Pro Gln Glu Thr Pro Thr Pro Ser
1               5                   10                  15

Ser Asp Gly Gly Ala Ser Leu Glu Glu Met Leu Thr Gln Ala Val Gln
            20                  25                  30

Glu Ala Asp Ile Glu Gln Val Arg Gln Leu Leu Glu Arg Gly Ala Asp
        35                  40                  45

Ala Asn Phe Gln Glu Glu Glu Trp Gly Trp Ser Pro Leu His Ser Ala
    50                  55                  60

Val Gln Met Asp Ser Glu Asp Leu Val Ala Leu Leu Lys His Gly
65                  70                  75                  80

Ala Asp Pro Cys Leu Arg Lys Arg Asn Gly Ala Thr Pro Phe Ile Ile
                85                  90                  95

Ala Gly Ile Thr Gly Asn Val Arg Leu Leu Gln Leu Leu Leu Pro Asn
            100                 105                 110

Val Glu Asp Val Asn Glu Cys Asp Val Asn Gly Phe Thr Ala Phe Met
        115                 120                 125

Glu Ala Ala Val Tyr Gly Arg Val Glu Ala Leu Arg Phe Leu Tyr Glu
    130                 135                 140

Asn Gly Ala Asp Val Asn Met His Arg Lys Thr Lys Gln Asp Gln Glu
145                 150                 155                 160

Arg Ile Arg Lys Gly Gly Ala Thr Ala Leu Met Asp Ala Ala Glu Lys
                165                 170                 175

Gly His Val Gly Val Val Thr Ile Leu Leu His Ala Met Lys Ala Glu
            180                 185                 190

Val Asp Ala Arg Asp Asn Met Gly Arg Asn Ala Leu Val Tyr Ala Leu
        195                 200                 205

Leu Asn Pro Asp Asp Gly Lys Ala Lys Ala Ile Thr Arg Leu Leu Leu
```

```
                210                 215                 220
Asp His Gly Ala Asp Val Asn Val Arg Gly Glu Gly Ser Lys Thr Pro
225                 230                 235                 240

Leu Ile Leu Ala Val Glu Arg Lys Asn Leu Asp Leu Val Gln Met Leu
                245                 250                 255

Leu Glu Gln Glu Gln Ile Glu Val Asn Asp Thr Asp Arg Glu Gly Lys
                260                 265                 270

Thr Ala Leu Leu Leu Ala Val Glu Leu Arg Leu Glu Glu Ile Ala Lys
                275                 280                 285

Leu Leu Cys His Arg Gly Ala Ser Thr Asn Cys Gly Asp Leu Val Ala
290                 295                 300

Ile Ala Arg Arg Asn Tyr Asp Ser Asp Leu Val Lys Phe Leu Arg Leu
305                 310                 315                 320

His Lys Ala Gly Glu Asp Phe Arg Pro Ala Glu Asn Trp Lys Pro
                325                 330                 335

Gln Ser Ser Arg Trp Gly Glu Ala Leu Lys His Leu His Arg Ile Trp
                340                 345                 350

Arg Pro Met Ile Gly Lys Leu Lys Ile Phe Ile Asp Glu Glu Tyr Lys
                355                 360                 365

Ile Ala Asp Thr Ala Glu Gly Gly Ile Tyr Leu Gly Leu Tyr Glu Asp
370                 375                 380

Gln Glu Val Ala Val Lys Arg Phe Ser Glu Gly Ser Thr Arg Gly Gln
385                 390                 395                 400

Gln Glu Val Ser Cys Leu Gln Ser Ser Arg Ala Asn Asp Asn Val Val
                405                 410                 415

Thr Phe Tyr Gly Ser Glu Ser Asp Gly Ser Cys Leu His Val Cys Leu
                420                 425                 430

Ala Leu Cys Glu Tyr Thr Leu Gln Glu His Leu Ala Asn His Arg Gly
                435                 440                 445

Asp Ala Val Pro Asn Glu Glu Asp Glu Ser Ala Arg Asn Ile Leu Ser
450                 455                 460

Ser Leu Phe Lys Ala Ile Gly Glu Leu His Arg Ser Gly Tyr Ser His
465                 470                 475                 480

Gln Asp Leu Gln Pro Gln Asn Ile Leu Ile Asp Ser Lys Asn Gly Thr
                485                 490                 495

Phe Leu Ala Asp Phe Asp Lys Ser Ile Lys Trp Ala Glu Asp Pro Gln
                500                 505                 510

Lys Ile Lys Arg Asp Leu Glu Ala Leu Gly Leu Leu Val Leu Tyr Val
                515                 520                 525

Val Lys Lys Gly Asp Ile Ser Phe Glu Thr Leu Lys Asn Gln Ser Phe
530                 535                 540

Glu Glu Val Ile Gln Gly Ser Pro Asp Glu Thr Arg Asp Leu Ile
545                 550                 555                 560

His His Leu Phe His Pro Gly Asp Asn Val Glu Asp Arg Leu Ser Ser
                565                 570                 575

Leu Leu Ala His Pro Phe Phe Trp Ser Trp Glu Ser Arg Tyr Arg Thr
                580                 585                 590

Leu Arg Asp Val Gly Asn Glu Ser Asp Ile Lys Thr Arg Asn Gln Asn
                595                 600                 605

Ser Arg Ile Leu Gln Leu Leu Gln Pro Gly Thr Ser Glu Leu Ser Thr
                610                 615                 620

Ser Phe Ala Gln Trp Thr Thr Lys Ile Asp Ser Phe Val Met Glu Glu
625                 630                 635                 640
```

```
Met Asn Ala Tyr Tyr Lys Lys Ile Ser Lys Lys Lys Ala Lys His
                645                 650                 655

Thr Asn Glu Gly Asn Leu Tyr Gln Asp Thr Leu Gly Asp Leu Leu Lys
            660                 665                 670

Phe Ile Arg Asn Leu Gly Glu His Ile Asn Glu Gln Lys Asn Lys Lys
        675                 680                 685

Met Lys Ser Ile Ile Gly Glu Pro Ser Gln Tyr Phe Gln Glu Lys Phe
    690                 695                 700

Pro Asp Leu Val Met Tyr Val Tyr Thr Lys Leu Gln Asn Thr Glu Tyr
705                 710                 715                 720

Met Lys His Phe Pro Lys Thr His Asn Pro Asn Lys Leu Arg Cys Asp
                725                 730                 735

Gly Ala Gly Asp Gly Gln Thr
                740
```

<210> SEQ ID NO 25
<211> LENGTH: 724
<212> TYPE: PRT
<213> ORGANISM: Canis Lupus Familiaris

<400> SEQUENCE: 25

```
Met Glu Thr Lys Ser His Asn Asn Leu Gln Glu Arg Pro Thr Pro Ser
1               5                   10                  15

Ser Asn Arg Arg Thr Ser Val Asp Gly Asn Gln Leu Ile Gln Ala Ile
            20                  25                  30

Lys Lys Glu Asp Ile Lys Leu Ile Gln Gln Leu Leu Glu Glu Gly Ala
        35                  40                  45

Asp Val Asn Phe Gln Glu Asn Glu Trp Gly Trp Ser Pro Leu His Asn
    50                  55                  60

Ala Val Gln Ile Cys Gln Asp Ile Val Asp Leu Leu Leu Arg Tyr
65                  70                  75                  80

Gly Ala Asp Pro Phe Leu Lys Lys Asn Glu Ala Thr Pro Phe Ile
                85                  90                  95

Val Ala Gly Ile Val Gly Asn Val Lys Leu Leu Lys Leu Phe Leu Ser
            100                 105                 110

Lys Gly Ala Asp Val Asn Glu Cys Asp Ala Asn Gly Phe Thr Ala Phe
        115                 120                 125

Met Glu Ala Ala Val Lys Asp Arg Val Glu Ala Leu Arg Phe Leu Tyr
    130                 135                 140

Glu Asn Gly Ala Asn Val Asn Leu Ser Arg Arg Thr Lys Glu Asp Gln
145                 150                 155                 160

Lys Arg Leu Lys Lys Gly Gly Ala Thr Ala Leu Met Asp Ala Ala Glu
                165                 170                 175

His Gly His Val Glu Val Lys Ile Leu Leu Asp Glu Met Gly Ala
            180                 185                 190

Asp Val Asn Val Cys Asp Asn Met Gly Arg Asn Ala Leu Ile His Val
        195                 200                 205

Phe Arg Ser Ser Asp Gly Arg Asn Met Glu Gly Ile Ile Arg Leu Leu
    210                 215                 220

Leu Asp His Gly Ala Asp Val Asn Val Arg Gly Glu Lys Gly Lys Thr
225                 230                 235                 240

Pro Leu Ile Leu Ala Val Glu Lys Lys His Leu Gly Leu Val Gln Met
                245                 250                 255

Leu Leu Glu Gln Glu His Ile Glu Val Asp Asp Thr Asp Ser Glu Gly
```

```
                260                 265                 270
Asn Thr Ala Leu Leu Ala Val Gln Tyr Arg Gln Glu Glu Ile Val
            275                 280                 285

Lys Leu Leu Cys Asn Lys Gly Ala Asn Met Asp Cys Gly Glu Leu Val
            290                 295                 300

Met Ile Ala Arg Arg Asn Tyr Asp Asn Ser Leu Ala Arg Leu Leu Leu
305                 310                 315                 320

Ser Tyr Gly Ala Arg Glu Asp Trp Cys Arg Pro Ala Glu Asp Trp Lys
                325                 330                 335

Pro Gln Ser Ala Arg Trp Gly Glu Ala Leu Glu His Leu Arg Arg Ile
            340                 345                 350

Tyr Arg Pro Met Ile Gly Arg Leu Lys Ile Phe Ile Asp Asp Glu Tyr
            355                 360                 365

Lys Ile Ala Asp Thr Ser Glu Gly Gly Ile Tyr Leu Gly Phe Tyr Glu
            370                 375                 380

Gly Gln Glu Val Ala Val Lys Arg Phe Tyr Glu Gly Ser Ala His Gly
385                 390                 395                 400

Gln Gln Glu Val Ser Cys Leu Gln Ser Ser Arg Thr Asn Ser Asp Leu
                405                 410                 415

Val Thr Phe Tyr Gly Ser Glu Ser Tyr Arg Asp Cys Leu Tyr Val Cys
            420                 425                 430

Leu Ala Leu Cys Glu Gln Thr Leu Glu Glu Tyr Leu Ala Asn His Arg
            435                 440                 445

Arg Glu Val Val Glu Asn Glu Glu Asp Ser Phe Ala Arg Asn Val Leu
450                 455                 460

Ser Ser Val Phe Lys Ala Val Glu Glu Leu His Val Arg Cys Gly Tyr
465                 470                 475                 480

Thr His Gln Asp Leu Gln Pro Arg Asn Ile Leu Leu Asp Ser Lys Asn
                485                 490                 495

Ala Val Cys Leu Ala Asp Phe Asp Lys Ser Ile Lys Trp Thr Gly Glu
            500                 505                 510

Thr Gln Glu Ile Arg Lys Asp Leu Glu Ala Leu Gly Leu Leu Val Leu
            515                 520                 525

Tyr Val Val Lys Lys Gly Glu Val Pro Phe Val Thr Leu Lys Thr Gln
            530                 535                 540

Ser His Glu Lys Ile Ile Gln Leu Ser Pro Asp Glu Glu Thr Arg Asp
545                 550                 555                 560

Leu Ile Tyr His Leu Phe Asn Pro Gly Asp Asn Val Leu Glu His Leu
                565                 570                 575

Ser Gly Leu Leu Gly His Pro Phe Phe Trp Ser Trp Glu Asn Arg Tyr
            580                 585                 590

Arg Thr Leu Arg Asp Val Gly Asn Glu Ser Asp Ile Lys Gln Arg Leu
            595                 600                 605

Arg Asn Ser Arg Ile Val Gln Leu Leu Gln Leu Glu Asn Ser Glu Cys
610                 615                 620

Ser Arg Thr Phe Ala Gln Trp Thr Ser Lys Ile Asp Lys Tyr Val Met
625                 630                 635                 640

Thr Val Met Asn Lys Phe Tyr Glu Lys Arg Asn Phe Tyr Glu Asp
                645                 650                 655

Thr Pro Ser Asp Leu Leu Lys Phe Ile Arg Asn Leu Gly Glu His Ile
            660                 665                 670

Asn Glu Asp Lys Asn Lys Glu Met Arg Leu Ile Ile Glu Glu Pro Ser
            675                 680                 685
```

```
Arg Tyr Leu Gln Met Lys Phe Pro Asp Leu Val Ile Tyr Val Tyr Lys
    690             695             700             705
        wait
```

Arg Tyr Leu Gln Met Lys Phe Pro Asp Leu Val Ile Tyr Val Tyr Lys
        690             695             700

Lys Leu Gln Asn Thr Glu Tyr Arg Lys His Phe Pro Lys Ile His Asn
705             710             715             720

Pro Asn Lys Asp

<210> SEQ ID NO 26
<211> LENGTH: 741
<212> TYPE: PRT
<213> ORGANISM: Myotis davidii

<400> SEQUENCE: 26

Met Glu Thr Lys Ser His Asn Asn Pro Gln Asp Arg Pro Thr Pro Ala
1               5                   10                  15

Gly Asn Gly Arg Thr Ser Gly Asp Asn Asn His Leu Leu Ile Thr Ala
            20                  25                  30

Val Lys Gln Leu Asp Met Glu Leu Val Lys Gln Leu Leu Glu Gly Gly
        35                  40                  45

Ala Asp Val Asn Phe Gln Glu Glu Gly Gly Trp Ser Pro Leu His
    50                  55                  60

Asn Ala Val Gln Met Asp Asn Glu Asp Met Val Glu Leu Leu Leu Arg
65                  70                  75                  80

Tyr Gly Ala Asn Pro Cys Leu Arg Lys Arg Asn Gly Ala Thr Pro Phe
                85                  90                  95

Ile Val Ala Gly Ile Val Gly Asn Val Lys Leu Leu Arg Leu Phe Leu
            100                 105                 110

Ser Lys Gly Ala Glu Ile Asn Glu Arg Asp Leu His Gly Phe Thr Ala
        115                 120                 125

Phe Met Glu Ala Ala Glu Tyr Gly Lys Val Glu Ala Leu Arg Phe Leu
130                 135                 140

Tyr Glu Asn Gly Ala Glu Val Asn Leu Gly Arg Lys Thr Met Glu Asp
145                 150                 155                 160

Gln Glu Arg Leu Lys Lys Gly Gly Ala Thr Ala Leu Met Asp Ala Ala
                165                 170                 175

Lys His Gly Arg Val Glu Val Leu Arg Ile Leu Leu Glu Glu Met Gly
            180                 185                 190

Ala Asp Val Arg Ala Arg Asp Asn Met Gly Arg Asn Ala Leu Ile His
        195                 200                 205

Ala Leu Ala Ser Pro Lys Asn Ser Asn Val Glu Ala Ile Thr Arg Leu
210                 215                 220

Leu Leu His His Gly Ala Asp Val Asn Val Ser Gly Glu Gly Gly Lys
225                 230                 235                 240

Thr Pro Leu Ile Leu Ala Val Glu Lys Gly His Leu Thr Leu Val Arg
                245                 250                 255

Met Phe Leu Glu Gln Lys Pro Ile Glu Ile Asp Asp Thr Asp Arg Glu
            260                 265                 270

Gly Lys Thr Ala Leu Leu Trp Ala Val Glu Leu Asn Leu Thr Glu Ile
        275                 280                 285

Ala Gln Leu Leu Cys Gly Lys Gly Ala Ser Thr Asp Cys Gly Asn Leu
290                 295                 300

Val Met Leu Ala Arg Arg His Tyr Asn Ser Ser Leu Val Lys Leu Leu
305                 310                 315                 320

Leu His His Gly Ala Arg Glu Asp Tyr His Pro Pro Ala Gly Asp Trp
                325                 330                 335

```
Glu Pro Gln Ser Ser His Trp Gly Pro Ala Leu Lys His Leu His Arg
                340                 345                 350

Ile Tyr Arg Pro Met Ile Gly Arg Leu Lys Ile Phe Arg Asp Glu Glu
            355                 360                 365

Tyr Lys Ile Ala Asp Ser Ser Glu Gly Gly Ile Tyr Leu Gly Phe Tyr
        370                 375                 380

Asp Asp Gln Glu Val Ala Val Lys Arg Phe Ser Glu Asp Ser Ser Leu
385                 390                 395                 400

Gly Gln Arg Glu Ile Ser Cys Leu Gln Ser Ile Arg Gly Asn Ser Asn
                405                 410                 415

Leu Val Thr Ile Tyr Gly His Glu Ile His Lys Gly Cys Leu Tyr Val
            420                 425                 430

Cys Thr Ser Leu Cys Glu Leu Thr Leu Glu Arg His Leu Ala Gln His
        435                 440                 445

Arg Gly Glu Ala Val Glu Asn Glu Glu Asp Glu Phe Ser Arg Asn Ile
    450                 455                 460

Leu Ser Ile Phe Lys Ala Val Glu Cys Ile Leu Ser Cys Gly Tyr
465                 470                 475                 480

Thr His Gln Asp Leu Gln Pro Gln Asn Ile Leu Ile Asp Ser Lys Asn
                485                 490                 495

Ala Val Arg Val Ala Asp Phe Asp Lys Ser Ile Lys Trp Ala Gly Glu
            500                 505                 510

Pro Glu Gln Val Lys Ser Asp Leu Glu Ala Leu Gly Arg Leu Val Leu
        515                 520                 525

Tyr Val Val Arg Lys Gly Asp Ile Pro Phe Glu Thr Leu Lys Thr Gln
        530                 535                 540

Ser Asn Glu Glu Val Ile Thr Leu Ser Pro Asn Glu Glu Ile Gln His
545                 550                 555                 560

Leu Leu Gln Gln Leu Phe Arg Leu Arg Glu Asn Val Glu Asn Leu Leu
                565                 570                 575

Ser Asp Leu Leu Gly His Pro Phe Phe Trp Ser Trp Glu Ser Arg Tyr
            580                 585                 590

Arg Thr Leu Arg Asp Val Gly Asn Glu Ser Glu Ile Lys Thr Lys Ile
        595                 600                 605

Gln Ser Gln Glu Leu Ser Ile Leu Gln Leu Leu Gln Pro Arg Pro Ser
        610                 615                 620

Glu Pro Ser Arg Ser Phe Asp Lys Trp Thr Ser Glu Ile Asp Glu Gly
625                 630                 635                 640

Ile Met Lys Lys Met Gln Gly Phe Tyr Arg Lys Pro His Leu Lys
                645                 650                 655

Tyr Gln Asp Thr Val Gly Asp Leu Leu Lys Phe Ile Arg Asn Leu Gly
            660                 665                 670

Glu His Ile His Gln Glu Asp Asn Arg Trp Met Lys Ser Ile Ile Pro
        675                 680                 685

Asp Pro Ser Arg Tyr Phe Gln Glu Lys Phe Pro Asp Leu Ile Ile Tyr
        690                 695                 700

Val Tyr Lys Arg Leu Gln Asn Thr Glu Tyr Ala Lys His Phe Pro Gln
705                 710                 715                 720

Ile His Asn Ala His Arg Pro Gln Cys Asp Glu Gly Asn Gly Gly Gln
                725                 730                 735

Gln Ala Thr Arg Pro
            740
```

REPORTER CONSTRUCT AND BIOSENSOR FOR INTERFERON SECOND MESSENGER 2-5A

CROSS REFERENCE TO RELATED APPLICATIONS

This application claims the priority benefit of U.S. Provisional Patent Application No. 62/631,188, filed Feb. 15, 2018, hereby incorporated by reference in its entirety.

This invention was made with government support under Grant No: GM110161 awarded by the National Institutes of Health/National Institute of General Medical Sciences (NIH/NIGMS). The government has certain rights in the invention.

INCORPORATION BY REFERENCE OF MATERIAL SUBMITTED ELECTRONICALLY

This application contains, as a separate part of disclosure, a sequence listing in computer-readable form (filename: 51449_Seqlisting.txt; 80,668 bytes; created Feb. 15, 2019) which is incorporated by reference in its entirety.

FIELD OF THE DISCLOSURE

The present disclosure relates, in general, to a reporter construct comprising a split reporter system fused to an RNase L protein and uses of the reporter construct in monitoring levels of 2'-5'-linked oligoadenylates, interferons and dsRNA in a subject in order to detect and treat inflammation and immune responses in the subject.

BACKGROUND

Cytosolic double-stranded RNA (dsRNA) accumulates during stresses such as viral infections or deficient editing of cellular dsRNA by ADAR (Liddicoat et al., 2015) and is a major immunogen for the mammalian innate immune system[10,11]. To detect increase in dsRNA and mount a protective response, the immune system is equipped with three interferon (IFN)—inducible receptors of the oligoadenylate synthetase family—OAS1, OAS2 and OAS3[2]. Upon binding to dsRNA, the OASs synthesize 2'-5'-linked oligoadenylates (2-5A)[2]. The 2-5As thus serves as dsRNA-induced and IFN-induced second messengers that signal dsRNA buildup. DsRNA also activates other sensors, such as RIG-I and MDA5, which in turn induce the type I IFN response[10]. However, RIG-I and MDA5 are activated by specific features in the dsRNA (RIG-I needs a 5'-triphosphate moiety and a short blunt end, whereas MDA5 needs long dsRNA, length optimally ~1 kb or more) typical of viral origin, whereas the OASs are sensitive to dsRNAs with only >17 bp or more[12,13]. Thus the OAS enzymes, and thereby 2-5A, are good sensors of the presence of a broad range of dsRNAs inside cells.

The 2-5As are recognized by the 2-5A receptor, RNase L. RNase L is a kinase domain-containing endoribonuclease RNase L[14], which has broad roles in both immune stress and homeostasis. RNase L is required for combating viruses such as West Nile[15] and Hepatitis C[16], and pathogenic bacteria such as *E. coli* and *B. anthracis*[17]. During acute dsRNA response, RNase L cleaves 18S and 28S ribosomal RNA (rRNA) and induces apoptosis[18]. Aside from pathogen defense, RNase L controls cell proliferation and adhesion[8,9] by selectively cleaving mRNA transcripts that converge with the anti-proliferative miR200 program[8]. Defects in RNase L signaling lead to grossly enlarged spleen and thymus[5], obesity and insulin resistance in mice[19]. A loss of RNase L results in spreading of prostate cancer and metastasis in mice[7] and RNase L mutations predispose men to hereditary prostate cancer[20].

The broad cellular outcomes ranging from differentiation and proliferation to apoptosis executed by RNase L signify the cell's acute sensitivity to changes in intracellular dsRNA load. The infection-uncoupled roles of RNase L suggest the presence of endogenous dsRNA that basally activates OASs. This self-dsRNA is reported to further accumulate by the action of DNA methyltransferase inhibitors that cause bidirectional transcription of endogenous retroviruses[21,22]. The cell can reduce its dsRNA load via editing enzymes such as adenosine deaminase (ADAR) which disrupts intracellular dsRNA structures[23] and Dicer which cleaves long dsRNA[24]. Loss of Adar results in embryonic lethality in mice[25] and mutations in Adar are associated with human autoimmune disorders[26]. Similarly, loss of Dicer is reported to induce inflammation, highlighting the need for tight regulation of dsRNA load[24].

2-5A bind latent RNase L with sub-nanomolar affinity[5,27] and drive its dimerization and activation in a highly cooperative manner[27]. 2-5A is critical for RNase L activation and antiviral response. This is best exemplified by evidence that show some viruses encode 2'-5' phosphodiesterases to degrade 2-5A and subvert immune surveillance[28]. Given the central role that 2-5A occupies in innate immune response, several methods have been developed to measure 2-5A levels including analyses of ribosomal RNA cleavage (the first-identified target of RNase L)[29], FRET RNA probes[30] and radioactively labeled RNA probes[31]. Although sensitive, these methods are endpoint assays requiring cell lysis or animal sacrifice and thus unfeasible for continuous monitoring of 2-5A in cells, in vivo, and in real time. The previous assays are not suitable for cell-based high-throughput screens for 2-5A response modulators. Current methods to detect intracellular dsRNA by antibodies, such as dsRNA antibodies, have similar limitations.

SUMMARY

The disclosure provides a fusion protein comprising RNase L and a split reporter protein that can measure 2-5A in vitro and in live cells. By serving as a 2-5A meter, this reporter construct indicates accumulation of cellular dsRNA. This reporter thus provides a new type of tools for monitoring viral infections, immune responses, diagnostics of 2-5A buildup in clinical samples and diagnostic tracking of therapeutic responses to treatments associated with immune system activation. Moreover, it will enable high-throughput testing of small molecules, stresses and disease states that may induce dsRNA activating an innate immune response. The 2-5A reporter is compatible with biochemical and cell-based high-throughput screens.

The present disclosure provides a fusion protein comprising RNase L or a functional fragment thereof fused to a reporter protein, wherein fragments of the reporter protein are fused to both the N-terminal side and the C-terminal side of the RNase L protein or fragment thereof. For example, when the fusion protein comprises a reporter protein having an N-terminal fragment of reporter protein fused to a portion of the RNase L or fragment thereof it would be followed by a C-terminal fragment of reporter protein, optionally fused to the opposite side of the RNase L or fragment thereof from the N-terminal reporter protein fragment. As first shown by the inventors, the dimerization of RNase L brings parts of this protein in proximity[27]. Therefore, RNase L or a fragment thereof brings two halves of the dimerization-sensing tag protein into proximity, such that the reporter is activated and changes in reporter signal are detected.

In various embodiments, the reporter protein is selected from the group consisting of luciferase, green fluorescent protein (GFP), red fluorescent protein (RFP), yellow fluorescent protein (YFP) and sfCHERRY. Additional reporters contemplated herein are described in more detail in the Detailed Description.

In various embodiments, the reporter protein is luciferase. In related embodiments, the luciferase comprises an N-terminal fragment of luciferase on one side of the RNase L or fragment thereof and a C-terminal fragment of luciferase fused to the opposite side of the RNase L or fragment thereof from the N-terminal luciferase fragment.

In various embodiments, the luciferase is firefly luciferase and the N-terminal fragment comprises amino acids 1-416 of firefly luciferase and the C-terminal fragment comprises amino acid residues 417-500 of firefly luciferase.

In various embodiments, the reporter protein is GFP and the N-terminal fragment comprises amino acids 1-214 of GFP and the C-terminal fragment comprises amino acid residues 215-230 of GFP.

In various embodiments, the reporter protein is sfCHERRY and the N-terminal fragment comprises amino acids 1-208 of sfCHERRY and the C-terminal fragment comprises amino acid residues 209-226 of sfCHERRY.

Sequences of exemplary reporter proteins are set out in Tables 1-3.

In various embodiments, the reporter protein is connected to the RNase L or fragment thereof via one or more linkers. In various embodiments, the linker is a peptide linker or a covalent linker. In various embodiments, the fusion protein may comprise one or more linkers, wherein each linker may be from 4 to 30, 4 to 20, 8 to 30, 8 to 20, 12 to 30, 12 to 20, 16 to 30 or 16 to 20 amino acids in length. It is contemplated that the linker can consist of 4, 5, 6, 7, 8, 9, 10, 11, 12, 13, 14, 15, 16, 17, 18, 19, 20 or more amino acids. In various embodiments, the linker is a GGGS (SEQ ID NO: 1) linker, and comprises 1, 2, 3 or 4 GGGS (SEQ ID NO: 1) repeats. In various embodiments, the linker is selected from the group consisting of $(GGGS)_2$ (SEQ ID NO: 2) or $(GGGS)_3$ (SEQ ID NO: 3).

In various embodiments, the RNase L is human, chimpanzee, mouse, rat, pig, dog or bat RNase L. Exemplary RNase L amino acid sequences are set out in Table 4. In various embodiments, the functional fragment of RNase L comprises all or part of an RNase L ankyrin (ANK) domain. In various embodiments, the ANK domain comprises 1, 2, 3, 4, 5, 6, 7, 8 or 9 ANK repeats. In various embodiments, the ANK domain comprises all 9 ANK repeats. In various embodiments, the ANK domain comprises residues 21-325 of the human RNase L protein set out in Table 4.

In various embodiments, the RNase L or functional fragment thereof binds to 2'-5' linked oligoadenylates (2-5A).

In various embodiments, an amino acid or nucleotide sequence of RNase L or fragment thereof is modified by substitution, deletion or insertion. In some embodiments, the modification is a Y312A mutation in the human RNase L amino acid sequence.

In various embodiments, the fusion protein further comprises a nuclear localization signal (NLS) or a nuclear export signal (NES). In some embodiments, the NLS is amino acid sequence PKKKRKVE (SEQ ID NO: 4). In some embodiments, the NES is set out in amino acid sequence LQLPPLERLTLD (SEQ ID NO: 5).

In various embodiments, the fusion protein is a monomer or a dimer.

In various embodiments, binding of RNase L to 2'-5'linked oligoadenylates (2-5A) results in head-to-tail dimerization of the RNase L composition and activation of the reporter.

Further contemplated herein is a nucleotide encoding a fusion protein as described herein.

Also provided by the disclosure is a vector expressing the fusion protein described herein or a nucleotide encoding a fusion protein described herein. Exemplary vectors include, viral vectors, plasmid vectors, liposomes, or other vectors known in the art, and are discussed in greater detail in the Detailed Description.

In various embodiments, the disclosure provides a composition comprising the fusion protein, nucleotide encoding the fusion protein or vector expressing the fusion protein as described herein.

Also provided is a method of detecting 2'-5' linked oligoadenylates (2-5A) comprising contacting a sample with a composition comprising a fusion protein described herein, wherein an increase in reporter signal compared to control is indicative of an increase in 2-5A in the sample.

The disclosure also contemplates a method of determining levels of double stranded RNA (dsRNA) in a sample comprising contacting the sample with a composition comprising a fusion protein described herein, and detecting levels of dsRNA based on signal emitted from the reporter, wherein an increase in reporter signal compared to control is indicative of an increase in dsRNA in the sample.

In various embodiments of the methods, the increase in 2-5A and/or dsRNA is associated with an infection or autoimmune disease. In some embodiments, the infection is a bacterial or viral infection.

Further contemplated is a method for detecting or monitoring progression of an immune response in a subject comprising i) contacting a sample from the subject with a composition comprising a fusion protein as described herein; ii) detecting levels of intracellular double stranded RNA (dsRNA) based on the signal emitted from the reporter, wherein an increase in dsRNA levels compared to control is indicative of an increasing immune response.

In one aspect, the disclosure provides a method for treating an immune response in a subject comprising i) contacting a sample from the subject with a composition comprising a fusion protein described herein; ii) detecting levels of intracellular double stranded RNA (dsRNA) based on the signal emitted from the reporter, wherein a change in dsRNA levels compared to control is indicative of a modulated immune response; and, iii) treating the subject with a therapeutic agent to treat the immune response when there is a change in levels of dsRNA. For example, a therapeutic may be administered when there is an increased level of dsRNA detected or a decreased level of dsRNA detected. In various embodiments of the methods, an increase in 2-5A and/or dsRNA is associated with an ongoing immune response.

In various embodiments of the methods, an increase in 2-5A and/or dsRNA is associated with an infection or autoimmune disease. In some embodiments, the infection is a bacterial or viral infection.

Also provided is a method for identifying a modulator of 2'-5' linked oligoadenylate (2-5A) binding to RNase L comprising i) contacting a sample with a composition comprising a fusion protein as described herein in the presence of a candidate modulator compound, and ii) detecting levels of intracellular dsRNA based on signal emitted from the reporter after step (i), wherein when the compound increases 2-5A binding to RNase L and increases dsRNA, the modulator is useful as a cancer therapeutic or anti-viral; or wherein when the compound decreases 2-5A binding to RNase L and decreases dsRNA, the modulator is useful as a therapeutic to treat autoimmune disease associated with self-dsRNA. In various embodiments, the composition comprising a fusion protein is/are reporter-bearing cell(s).

In various embodiments the sample is isolated from a subject or is an in vitro sample. The sample includes, but is not limited to, cells, cell lysate, any bodily fluid, blood, plasma, cerebrospinal fluid, urine, saliva, or tissue. In certain embodiments the cells are live cells. In some embodiments, the sample is a cell or cell lysate In various embodiments, the detecting comprises one or more of i) contacting the sample with luciferin substrate and detection is by luminescence readout; ii) isolation of RNA samples to detect 2-5A levels and the detection is by RNA analysis; iii) isolation of dsRNA and detection of dsRNA levels; iv) detection of luciferase or RNase L protein levels by Western blot; or v) immunofluorescence.

In some embodiments, the detecting is carried out in live cells. In some embodiments, the methods are high-throughput methods.

In another aspect, the disclosure provides a kit comprising a fusion protein as described herein, a nucleotide encoding a fusion protein, a vector expressing a fusion protein as described herein or a composition comprising said fusion protein, nucleotide or vector, and instructions for use.

BRIEF DESCRIPTION OF THE DRAWINGS

FIG. 2A) Schematic for the reporter construct with two linkers L1 and L2 are shown. Six different reporter constructs were tested with changes in either L1 or L2. FIG. 2B). Luminescence assays were carried out with 5 µM 2-5A.

FIG. 3A) Luminescence assays were carried out with a fixed saturating concentration of 2-5A (pA3=1 µM). Final concentration of 400 µM luciferin substrate was used in these reactions. FIG. 3B) Luminescence assay with 200 nM of V6 or Y312A V6 control recombinant reporter protein. FIG. 3C) HeLa cells treated with 6 hrs of dsRNA (poly IC) were lysed and passed through a centrifugal filter to collect flow-through of small molecules <3 kDa. Small nucleic acids from the flow through were ethanol precipitated. Luciferase assay was carried out with equivalent amounts of RNA from each treated sample. Data is presented as fold change in reporter activity in poly IC treated sample relative to mock sample. FIG. 3D) Small RNA from poly IC treated samples contains 2-5A as shown by cleavage of radiolabeled RNase L substrate.

FIG. 4A) Immunoblot analysis against the FLAG tag shows both V6 and Y312A V6 control proteins expressed in HeLa cells after 24 hours of transfection. FIG. 4B) Fold induction of V6 or Y312A V6 control reporter measured immediately after poly IC addition. FIG. 4C) Total RNA from HeLa cells treated with poly IC for the indicated times were harvested and run on a BioAnalyzer.

FIG. 5A) D-luciferin ethyl ester dose titration. HeLa cells expressing V6 or Y312A V6 constructs were transfected with poly IC for 6 hrs. Fold induction of the reporter is shown with different doses of the luciferin substrate tested. FIG. 5B) Lack of negative regulation in 2-5A levels following poly IC treatment. Endpoint assays where V6 or Y312A V6 reporter expressing constructs were treated with poly IC for the indicated times in a tissue culture incubator.

FIG. 6A) NLS/NES-FLAG tagged V6 reporter construct expressed in HeLa cells for 24 hours was visualized by anti-FLAG immunofluorescence. Nuclei are stained with DAPI. FIG. 6B) Live cell monitoring of 2-5A after addition of poly IC in cells expressing V6 constructs with different subcellular tags. FIG. 6C) In response to double stranded RNA, 2-5A is rapidly equilibrated between nuclear and cytoplasmic compartments.

(FIG. 8A) Luminescence analysis of 2-5A dynamics in A549 cells stably expressing FLAG-V6 2-5A biosensor at the indicated times after poly I:C treatment. P-value was computed from the three experiments at the highest dose of poly-IC vs 0.1 µg/ml poly-IC. (FIG. 8B) qRT-PCR analysis of ISG expression in A549 cells after poly-IC treatment vs untreated controls. Data are means ±S.E. from 3 biological replicates (4 h time point with 1 µg/ml poly-IC had 2 replicates; several measurements use 4 replicates). (FIG. 8C) RNA nano-chip analysis of 28S rRNA cleavage in A549 cells treated with poly IC for the indicated times. Arrows indicate a major RNase L-induced cleavage product. Images are representative of 3 independent experiment. (FIG. 8D) qRT-PCR analysis of ISG expression in A549 cells at 24 hours after poly-IC, IFN-β, or combined treatment. Data are means ±S.E. from three biological replicates. (FIG. 8E) Luminescence analysis of 2-5A dynamics in A549 cells with and without 24-hour IFN-β pre-treatment. Data are means ±S.E. pooled from at least 3 independent experiments. (FIG. 8F) Puromycin western blot analysis of nascent protein synthesis in WT and RNase L knockout (RNL-KO) A549 cells after treatment with poly I:C for the indicated times. Blots are representative of three independent experiments. (FIG. 8G) Western blot and autoradiography analysis of nascent protein synthesis in A549 cells labeled with puromycin or $^{35}$S metabolic labeling after treatment with poly I:C for the indicated times. Blots are representative of four independent experiments.

FIGS. 9A-9F IFN synthesis after 2-5A-induced global translation shutoff. (FIG. 9A) Diagram of interferon secretion experiment. (FIG. 9B) Puromycin western blot (upper) and RNA nano-chip (lower) analysis of translation and 28S rRNA cleavage in poly-IC-treated A549 cells. Images are representative of four independent experiments. (FIG. 9C) Antiviral activity of conditioned media from poly-IC-treated A549 cells (upper). Condensed results from three additional replicates are shown on figure S8. (FIG. 9D) qRT-PCR analysis of ISG expression in WT and RNL-KO A549 cells treated with conditioned media. from poly-ICIttreated A549 cells (lower). Data are means ±S.E. pooled from 3 biological replicates. RNA nano-chip (inset) of intact rRNA is representative of all experiments. (FIG. 9E) qRT-PCR analysis of ISG expression in A549 cells treated with anisomycin after translational arrest by poly-IC, but before the transcriptional IFN response. Data are means ±S.E. pooled from 3 biological replicates. (FIG. 9F) Effect of anisomycin treatment on transcriptional IFN signaling.

(FIG. 10A) Poly-A+ RNA-seq profiles analysis of IFN mRNA expression in A549 cells treated with poly-IC (1 µg/ml, 9 hours). Data were mapped to hg19 assembly and plotted. Of note, our RNA-seq found that actual IFN-λ genes span slightly beyond their annotated coordinates in the reference genome hg19. This is still uncorrected in hg38. (FIG. 10B) Western blot analysis of pSTAT1 levels in CHO reporter cells for type I IFN (upper) or type III IFN (lower). Reporter cells were treated with conditioned media from A549 cells incubated with poly IC and anisomycin, as indicated. Blots are representative of 3 independent experiments. (FIG. 10C) Proposed role for 2-5A/RNase L in dsRNA sensing. 2-5A rapidly switches translation from basal proteins to prioritized IFN-β and IFN-λ synthesis and secretion.

FIGS. 11-19 show amino acid and DNA sequences of representative fusion constructs according to the invention.

DETAILED DESCRIPTION

Definitions

Figure 1:
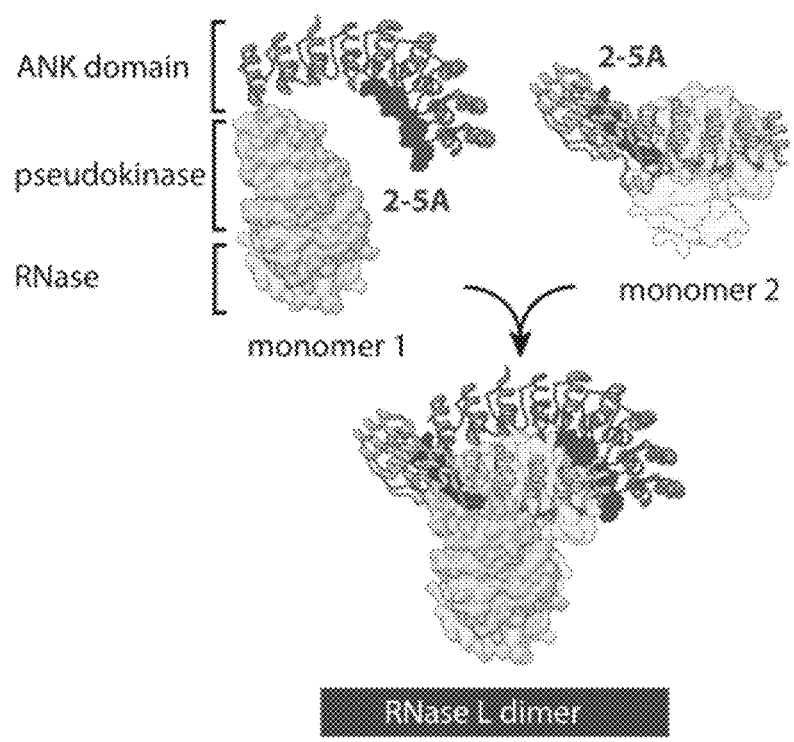
FIG. 1. Split luciferase system to engineer a novel 2-5A reporter. RNase L activation occurs via self-association into homo-dimers. The N terminal ANK domain dimerizes with two 2-5A molecules bound in a signature head-to-tail architecture. In the reporter system, the ANK domain is flanked by N terminal and C terminal firefly luciferase domains. Upon dimerization in the presence of 2-5A, the head-to-tail configuration permits the luciferase fragments to come together to reconstitute the functional luciferase enzyme. Luminescence can be detected in the presence of luciferin substrate.
Figure 1:
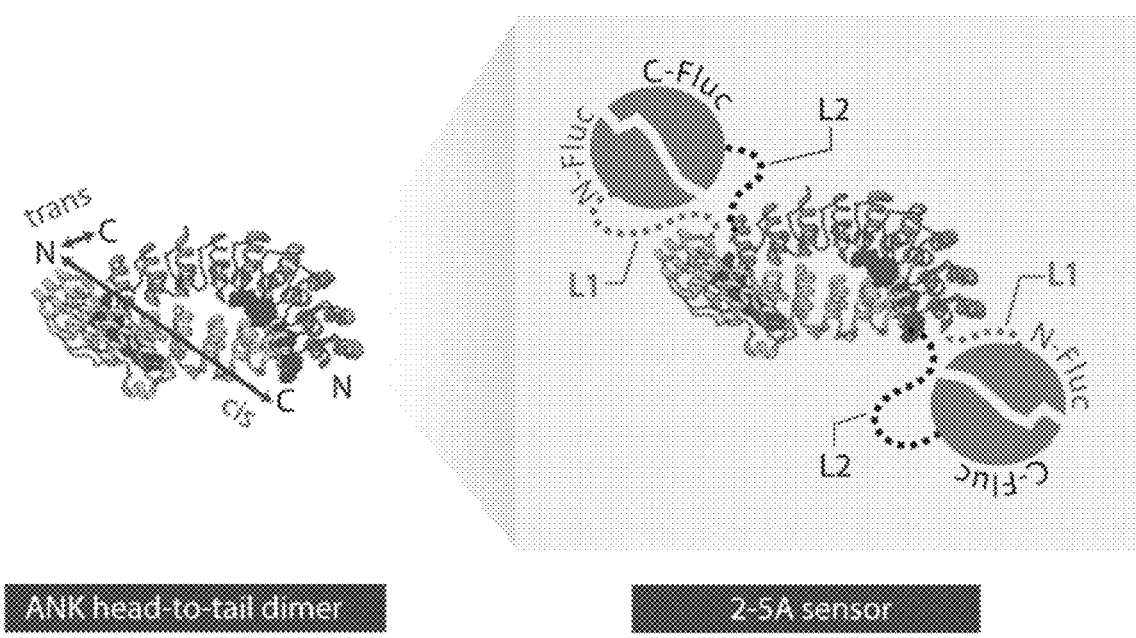

Unless otherwise stated, the following terms used in this application, including the specification and claims, have the definitions given below.

As used in the specification and the appended claims, the indefinite articles "a" and "an" and the definite article "the" include plural as well as singular referents unless the context clearly dictates otherwise.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, or 0.05% of a given value or range. Whenever the term "about" or "approximately" precedes the first numerical value in a series of two or more numerical values, it is understood that the term "about" or "approximately" applies to each one of the numerical values in that series.

Definition of standard chemistry terms may be found in reference works, including Carey and Sundberg, Advanced Organic Chemistry, 3$^{rd}$ Edition, Vols. A and B (Plenum Press, New York 1992). The practice of the present disclosure may employ, unless otherwise indicated, certain conventional methods of synthetic organic chemistry, mass spectrometry, preparative and analytical chromatography, protein chemistry, biochemistry, recombinant DNA technology and pharmacology, within the skill of the art. See, e.g., T. E. Creighton, Proteins: Structures and Molecular Properties (W.H. Freeman and Company, 1993); A. L. Lehninger, Biochemistry (Worth Publishers, Inc., 4$^{th}$ Edition, 2004); Sambrook, et al., Molecular Cloning: A Laboratory Manual (2$^{nd}$ Edition, 1989); Methods In Enzymology (S. Colowick and N. Kaplan eds., Academic Press, Inc.); Remington's Pharmaceutical Sciences, 18$^{th}$ Edition (Easton, Pa.: Mack Publishing Company, 1990).

All publications, patents and patent applications cited herein, whether supra or infra, are hereby incorporated by reference in their entirety.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gln (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

Conventional notation is used herein to portray polypeptide and peptide sequences: the left-hand end of a polypeptide or peptide sequence is the amino-terminus; the right-hand end of a polypeptide sequence is the carboxyl-terminus.

The term "RNase L" or RNase L fragment" refers to a mammalian endoribonuclease regulated by the action of double stranded RNA (dsRNA) and interferons (IFNs) α/β/λ, which induce the intracellular synthesis of a specific RNase L activator, 2-5A. Human RNase L is a 741 amino acid protein, having the nucleotide and polypeptide sequences set out in NCBI accession numbers NM_021133.3 and NP_066956.1, respectively. RNase Lisa member of the protein kinase superfamily and contains 9 ankyrin (ANK) repeats at residues 24-53, 58-87, 91-120, 124-153, 167-197, 201-234, 238-268, 272-301, 303-329 of human RNase L, contains a KEN domain at residues 365-586 of human RNase L, and a protein kinase domain from residues 589-723 of human RNase L. The nine ankyrin repeats, also called 2-5A sensor, constitute the N-terminus 2-5A binding domain. Ankyrin repeats typically fold together to form a single, linear solenoid structure called ankyrin repeat domains or ANK domains. The protein kinase domain is predicted to be catalytically inactive. Exemplary RNase L proteins are set out in Table 4, and portions of the ANK domain are underlined therein.

The term "domain" as used herein refers to a contiguous sequence on a polynucleotide or polypeptide that has a particular function, e.g., ANK domain of RNase L. The term "region" as used herein refers to a contiguous or non-contiguous sequence on a polypeptide or polynucleotide.

The term "reporter" as used herein refers to a protein, nucleotide or other compound that can be used as a readout for enzymatic or other biological activity. In some embodiments, the reporter may be a fluorescent or luminescent reporter, e.g., luciferase, green fluorescent protein (GFP), red fluorescent protein (RFP), yellow fluorescent protein (YFP), cyan fluorescent protein (CFP), blue fluorescent protein (BFP), a split fluorescent protein (see e.g., US Patent Publication 20150099271, International Patent Publication No. WO/2005/074436), sfCHERRY, and bilirubin-inducible fluorescent protein UnaG, dsRed, eqFP611, Dronpa, TagRFPs, KFP, EosFP, Dendra, IrisFP.

A split-fluorescent protein (SFP) refers to a protein complex composed of two or more protein fragments that individually are not fluorescent, but, when they form a complex result in a functional fluorescent protein complex. SFP include, but are not limited to, split-GFP, split YFP, and others known in the art (see e.g., U.S. Patent Publication 20150099271).

The term "linker" refers to a polypeptide polynucleotide or other compound that connects or links one molecule with another, e.g., connecting a polypeptide with another polypeptide or a polynucleotide. A linker may be either a polypeptide linker or a chemical linker. In various embodiments, the linker is a peptide linker. In the present reporter construct, the fusion protein may comprise one or more additional linkers, wherein each linker may be from 0 to 300, 0 to 60, 0 to 30, 0 to 10, 0 to 20, 4 to 30, 4 to 20, 8 to 30, 8 to 20, 12 to 30, 12 to 20, 16 to 30 or 16-20 amino acids in length. It is contemplated that the linker can consist of 0, 1, 2, 3, 4, 5, 6, 7, 8, 9, 10, 11, 12, 13, 14, 15, 16, 17, 18, 19, 20 or more amino acids. In various embodiments, the linker is a GGGS (SEQ ID NO: 1) repeat, and may be 1, 2, 3 or 4 GGGS (SEQ ID NO: 1) repeats. In various embodiments, the fusion protein comprises a natural linker in the RNase L protein.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, genomic RNA, mRNA, non-coding RNAs, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be a oligodeoxynucleoside phosphoramidate (P-NH2) or a mixed phosphoramidate-phosphodiester oligomer. Peyrottes et al. (1996) Nucleic Acids Res. 24: 1841-8; Chaturvedi et al. (1996) Nucleic Acids Res. 24: 2318-23; Schultz et al. (1996) Nucleic Acids Res. 24: 2966-73. A phosphorothioate linkage can be used in place of a phosphodiester linkage. Braun et al. (1988) J. Immunol. 141: 2084-9; Latimer et al. (1995) Molec. Immunol. 32: 1057-1064. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer. Reference to a polynucleotide sequence (such as referring to a SEQ ID NO) also includes the complement sequence.

The following are non-limiting examples of polynucleotides: a gene or gene fragment, exons, introns, genomic RNA, mRNA, tRNA, rRNA, snoRNA, vtRNA, Y-RNA, microRNA, ribozymes, cDNA, U-RNA, snRNAs, exRNAs, piRNAs and scaRNAs, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracil, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support.

The phrase "substantially homologous" or "substantially identical" in the context of two nucleic acids or polypeptides, generally refers to two or more sequences or subsequences that have at least 40%, 60%, 80%, 90%, 95%, 96%, 97%, 98% or 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of either or both comparison biopolymers. It is understood that RNA and DNA sequences can be considered identical, but have the RNA base substituted for the DNA base, or vice versa, in the sequence. For example, an RNA sequence is considered identical to a DNA sequence if it has a U in place of a T in the same position.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Natl. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by visual inspection. Alignment is also measured using such algorithms as PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Another algorithm that is useful for generating multiple alignments of sequences is Clustal W (Thompson et al., *Nucleic Acids Research* 22: 4673-4680, 1994). Another example of algorithm that is suitable for determining percent sequence identity and sequence similarity is the BLAST algorithm, which is described in Altschul et al., *J. Mol. Biol.* 215:403-410, 1990. Software for performing BLAST analyses is publicly available through the National Center for Biotechnology Information.

"Encoding" refers to the property of specific sequences of nucleotides in a polynucleotide, such as a gene, a cDNA, or an mRNA, to serve as templates for synthesis of other polymers and macromolecules in biological processes having either a defined sequence of nucleotides or a defined sequence of amino acids and the biological properties resulting therefrom. Thus, a gene or polynucleotide encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Vector" or "expression vector" as used herein refers to a replicon, such as plasmid, phage, virus, or cosmid, to which another polynucleotide segment, i.e. an "insert", may be attached so as to bring about the replication of the attached segment in a cell and, in some embodiments, expression of a desired protein encoded by the polynucleotide replicon. Exemplary vectors are described further below.

"Appropriate conditions" as used herein refers to those conditions that are determined by one of ordinary skill in the art, and refer to cell culture conditions, in vitro experimental conditions or nucleic acid hybridization conditions.

"Purified" as used herein refers to a reporter construct or 2-5A or polynucleotide (e.g., dsRNA) that has been isolated under conditions that reduce or eliminate the presence of unrelated materials, i.e., contaminants, including endogenous materials from which the composition is obtained. By way of example, and without limitation, a purified polypeptide or polynucleotide is substantially free of host cell or culture components, including tissue culture or cell proteins and non-specific pathogens. In various embodiments, purified material substantially free of contaminants is at least 50% pure; at least 60%, at least 70%, at least 80%, at least 90%, at least 95%, at least 96%, at least 97%, at least 98% or even at least 99% pure. Purity can be evaluated by chromatography, gel electrophoresis, immunoassay, composition analysis, biological assay, and other methods known in the art.

"Inflammation," "immune response" or "inflammatory response" as used herein refers to any and all such inflammatory reactions including, but not limited to, immune-related responses and/or allergic reactions to a physical, chemical, or biological stimulus. An immune response may involve the humoral immune system as well as the innate and adaptive immune systems, including activation of B cells, T cells, other lymphocytes, monocytes, neutrophils, eosinophils and basophils, production of antibodies, cytokines and chemokines and other immunologic response mechanisms well-known to those of skill in the art. Diseases or disorders that result from or cause inflammation are readily known to a person of skill in the art, and are described in additional detail below.

Expression of the Construct

For recombinant production of the fusion protein or reporter construct, the nucleic acid encoding it is isolated and inserted into a replicable vector for further cloning (amplification of the DNA) or for expression. DNA encoding the reporter construct is readily isolated and sequenced using conventional procedures (e.g., by using oligonucleotide probes that are capable of binding specifically to genes encoding the proteins). Many vectors are available. The vector components generally include, but are not limited to, one or more of the following: a signal sequence, an origin of replication, one or more selective marker genes, an enhancer element, a promoter, and a transcription termination sequence.

Exemplary expression vectors include, but are not limited to, viral vectors including, but not limited to the following: (e.g. viral vectors based on vaccinia virus; poliovirus; adenovirus (see, e.g., Li et al., Invest Opthalmol Vis Sci 35:2543 2549 (1994); Borras et al., Gene Ther 6:515 524 (1999); Li and Davidson, PNAS 92:7700-7704 (1995); Sakamoto et al., H Gene Ther 5:1088-1097 (1999); WO 94/12649, WO 93/03769; WO 93/19191; WO 94/28938; WO 95/11984 and WO 95/00655); adeno-associated virus (see, e.g., Ali et al., Hum Gene Ther 9:81 86 (1998), Flanner et al., PNAS 94:6916-6921 (1997); Bennett et al., Invest Opthalmol Vis Sci 38:2857-2863 (1997); Jomary et al., Gene Ther 4:683-690 (1997), Rolling et al., Hum Gene Ther 10:641-648, (1999); Ali et al., Hum Mol Genet 5:591-594 (1996); Srivastava in WO 93/09239, Samulski et al., J. Vir. 63:3822-3828 (1989); Mendelson et al., Virol. 166:154-165 (1988); and Flotte et al., PNAS 90:10613-10617 (1993)); SV40; herpes simplex virus; human immunodeficiency virus (see, e.g., Miyoshi et al., PNAS 94:10319-23 (1997); Takahashi et al., J Virol 73:7812-7816 (1999)); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus).

Plasmid vectors include, but are not limited to, pXT1, pSG5 (Stratagene), pSVK3, pBPV, pMSG, and pSVLSV40 (Pharmacia). Suitable transcription and translation control elements, including constitutive and inducible promoters, transcription enhancer elements, transcription terminators, may be used in the expression vector (see e.g., Bitter et al., Methods in Enzymology, 153:516-544 (1987)).

Suitable host cells for cloning or expressing the polynucleotide in the vectors herein are prokaryote, yeast, or higher eukaryote cells. Suitable prokaryotes for this purpose include eubacteria, such as Gram-negative or Gram-positive organisms, for example, *Enterobacteriaceae* such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

Examples of useful mammalian host cell lines are Chinese hamster ovary cells, including CHOK1 cells (ATCC CCL61), DXB-11, DG-44, and Chinese hamster ovary cells/-DHFR (CHO, Urlaub et al., *Proc. Natl. Acad. Sci. USA* 77: 4216 (1980)); monkey kidney CV1 line transformed by SV40 (COS-7, ATCC CRL 1651); human embryonic kidney line (293 or 293 cells subcloned for growth in suspension culture, (Graham et al., *J. Gen Virol.* 36: 59 (1977)); baby hamster kidney cells (BHK, ATCC CCL 10); mouse sertoli cells (TM4, Mather, (*Biol. Reprod.* 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y Acad. Sci.* 383: 44-68 (1982)); MRC 5 cells; FS4 cells; and a human hepatoma line (Hep G2).

Host cells are transformed or transfected with the above-described expression or cloning vectors for protein production and cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful and preferred for the expression of proteins.

Host cells containing desired fusion protein nucleic acid sequences may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al. *Meth. Enz.* 58: 44 (1979); Barnes et al. *Anal. Biochem.* 102: 255 (1980); U.S. Pat. Nos. 4,767,704; 4,657,866; 4,927,762; 4,560,655; or 5,122,469; WO90103430; WO 87/00195; or U.S. Pat. Re. No. 30,985, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Methods of Use

RNase L and associated molecules such as 2-5A and dsRNA are involved in the immune response pathway, with increased 2-5A and/or dsRNA levels detectable when the immune system is activated, for example, during infection, in cancers, in autoimmune diseases or other instances when there is an ongoing immune response.

It is contemplated that the 2-5A and/or dsRNA products are detected in a sample, optionally an invitro sample or one isolated from a subject. The sample includes, but is not limited to, cells, cell lysate, any bodily fluid, blood, plasma, cerebrospinal fluid, urine, saliva, or tissue. In certain embodiments the cells are live cells.

The subject can be a mammal, including humans, other primates, cows, horses, sheep, pigs, cats, dogs, hamsters, mice, rats and bats, as well as non-mammal animals including fowl and other birds. In various embodiments, the subject is a human.

Provided herein is a method of detecting 2'-5' linked oligoadenylates (2-5A) comprising contacting a sample with a composition comprising a fusion protein described herein, wherein an increase in reporter signal compared to control is indicative of an increase in 2-5A in the sample.

Further contemplated is a method for detecting or monitoring progression of an immune response in a subject comprising i) contacting a sample from the subject with a composition comprising a fusion protein as described herein; ii) detecting levels of intracellular double stranded RNA (dsRNA) based on the signal emitted from the reporter, wherein an increase in dsRNA levels compared to control is indicative of an increasing immune response.

The disclosure also contemplates a method of determining levels of double stranded RNA (dsRNA) in a sample comprising contacting the sample with a composition comprising a fusion protein described herein, and detecting levels of dsRNA based on signal emitted from the reporter, wherein an increase in reporter signal compared to control is indicative of an increase in dsRNA in the sample.

Provided in the disclosure is a method for detecting inflammation, an immune response or an interferon response in a subject comprising detecting 2-5A and/or dsRNA products according to the methods herein, wherein an increase in overall 2-5A and/or dsRNA indicates the subject is suffering from inflammation, an immune response or an interferon response.

Also contemplated herein is a method for treating an immune response in a subject comprising i) contacting a sample from the subject with a composition comprising a fusion protein described herein; ii) detecting levels of intracellular double stranded RNA (dsRNA) based on the signal emitted from the reporter, wherein a change in dsRNA levels compared to control is indicative of a modulated immune response; and, iii) treating the subject with a therapeutic agent to treat the immune response when there is a change in levels of dsRNA detected. In various embodiments, an increase in dsRNA is associated with an ongoing immune response.

Also contemplated herein is a method for treating an immune response in a subject comprising i) contacting a sample from the subject with a composition comprising a fusion protein described herein; ii) detecting levels of intracellular double stranded RNA (dsRNA) based on the signal emitted from the reporter, wherein an increase in dsRNA levels compared to control is indicative of an ongoing immune response; and, iii) treating the subject with a therapeutic agent to treat the immune response when there is an increased level of dsRNA detected.

The disclosure contemplates a method for determining efficacy of an anti-inflammatory treatment in a subject suffering from inflammation comprising detecting 2-5A and/or dsRNA levels in a subject according to the methods herein before and after administration of an anti-inflammatory agent, wherein a decrease in overall detecting 2-5A and/or dsRNA levels after administration indicates the anti-inflammatory agent is reducing inflammation in the subject.

In various embodiments, the inflammation is a result of an infection, an autoimmune disease, asthma or cancer. In some embodiments, the subject is suspected of suffering from a disorder with cell loss, such as a neurodegenerative disorder or diabetes.

Exemplary infections include bacterial, viral, fungal or parasitic infections. Exemplary autoimmune diseases include, but are not limited to, systemic lupus erythematosus, multiple sclerosis, rheumatoid arthritis, connective tissue disease, autoimmune pulmonary inflammation, Guillain-Barre syndrome, autoimmune thyroiditis, insulin dependent diabetes mellitus, myasthenia gravis, graft-versus-host disease and autoimmune inflammatory eye disease. Exemplary allergic reactions and conditions include, but are not limited to, asthma (particularly allergic asthma) or other respiratory problems, anaphylaxis, serum sickness, drug reactions, food allergies, insect venom allergies, mastocytosis, allergic rhinitis, hypersensitivity pneumonitis, urticaria, angioedema, eczema, atopic dermatitis, allergic contact dermatitis, erythema multiforme, Stevens-Johnson syndrome, allergic conjunctivitis, atopic keratoconjunctivitis, venereal keratoconjunctivitis, giant papillary conjunctivitis and contact allergies.

Exemplary cancers include, but are not limited to, leukemias, brain tumors (including meningiomas, glioblastoma multiforme, anaplastic astrocytomas, cerebellar astrocytomas, other high-grade or low-grade astrocytomas, brain stem gliomas, oligodendrogliomas, mixed gliomas, other gliomas, cerebral neuroblastomas, craniopharyngiomas, diencephalic gliomas, germinomas, medulloblastomas, ependymomas. choroid plexus tumors, pineal parenchymal tumors, gangliogliomas, neuroepithelial tumors, neuronal or mixed neuronal glial tumors), lung tumors (including small cell carcinomas, epidermoid carcinomas, adenocarcinomas, large cell carcinomas, carcinoid tumors, bronchial gland tumors, mesotheliomas, sarcomas or mixed tumors), prostate cancers (including adenocarcinomas, squamous cell carcinoma, transitional cell carcinoma, carcinoma of the prostatic utricle, or carcinosarcomas), breast cancers (including adenocarcinomas or carcinoid tumors), or gastric, intestinal, or colon cancers (including adenocarcinomas, invasive ductal carcinoma, infiltrating or invasive lobular carcinoma, medullary carcinoma, ductal carcinoma in situ, lobular carcinoma in situ, colloid carcinoma or Paget's disease of the nipple), skin cancer (including melanoma, squamous cell carcinoma, tumor progression of human skin keratinocytes, basal cell carcinoma, hemangiopericytoma and Karposi's sarcoma), lymphoma (including Hodgkin's disease and non-Hodgkin's lymphoma), and sarcomas (including osteosarcoma, chondrosarcoma and fibrosarcoma).

In various embodiments, an increase in detecting 2-5A and/or dsRNA levels is indicative of aberrant signaling in the immune response pathway.

It is contemplated that the method is useful in a subject who is receiving treatment for an infection, autoimmune disease, asthma, cancer or a disease in which there is cell loss such as a neurodegenerative disease. The treatment is one that is appropriate for the disorder, e.g., chemo-or radio-therapeutic for cancer, a cancer-specific antibody or antibody drug conjugate, other anti-inflammatory agents, anti-infective agents such as antibiotics, anti-virals, antifungals, and specific treatments for autoimmune diseases.

Also provided is a method for identifying a modulator of 2'-5' linked oligoadenylate (2-5A) binding to RNase L comprising i) contacting a sample with a composition comprising a fusion protein as described herein in the presence of a candidate modulator compound, and ii) detecting levels of intracellular double stranded RNA (dsRNA) based on the signal emitted from the reporter after step (i), wherein when the compound increases 2-5A binding to RNase L and increases dsRNA, the modulator is useful as a cancer therapeutic or anti-viral; or wherein when the compound decreases 2-5A binding to RNase L and decreases dsRNA, the modulator is useful as a therapeutic to treat autoimmune disease associated with self-dsRNA.

In various embodiments of the methods, the detecting comprises one or more of i) contacting the sample with luciferin substrate and detection is by luminescence readout; ii) isolation of RNA samples to detect 2-5A levels and the detection is by RNA analysis; iii) isolation of dsRNA and detection of dsRNA levels; iv) detection of luciferase or RNase L protein levels by Western blot; or v) immunofluorescence.

Kits

As an additional aspect, the disclosure includes kits which comprise one or more fusion protein/reporter construct, nucleotides encoding said fusion protein/reporter construct or vector expressing said fusion protein/construct, or compositions described herein packaged in a manner which facilitates their use to practice methods of the disclosure. In one embodiment, such a kit includes a compound or composition described herein (e.g., a vector or composition comprising a fusion protein or reporter construct or polynucleotide encoding said protein), packaged in a container such as a sealed bottle or vessel, with a label affixed to the container or included in the package that describes use of the compound or composition in practicing the methods described herein. Preferably, the compound or composition is packaged in a unit dosage form. The kit may further include a device suitable for using the composition according to a specific route of administration or for practicing a screening assay. Preferably, the kit contains a label that describes use of the compositions.

Additional aspects and details of the disclosure will be apparent from the following examples, which are intended to be illustrative rather than limiting.

EXAMPLES

This reporter design draws from the structural basis of 2-5A sensing by its natural receptor, RNase L. The crystal structures of both the full length and ANK (2-5A sensing) domain of RNase L with 2-5A revealed that the ANK domain forms a head-to-tail dimer upon binding two 2-5A molecules[27] (FIG. 1). It was hypothesized herein that adding luciferase halves on either side of the ANK domain would reconstitute the functional luciferase only upon 2-5A-dependent RNase L dimerization. Thus, the amount of light emitted by cells in the presence of luciferin provides a direct readout for 2-5A levels (FIG. 1). The head-to-tail nature of dimerization makes this split system favorable because instead of co-expressing two different constructs, as is common for such systems, one construct suffices to capture 2-5A.

Methods

Tissue culture: Cells were grown using ATCC (American Type Culture Collection) or provider recommended conditions in MEM media+10% FBS (HeLa) or RPMI media+10% FBS (A549), or DMEM media+10% FBS (293T). All media were purchased from Gibco, Life Technologies. HeLa and 293T were a gift from Yibin Kang (Princeton University, Princeton). WT, RNase L KO, and OAS KO A549 were generated by the laboratory of Susan Weiss (University of Pennsylvania, Philadelphia). Luminescence assays in live cells were carried out in a plate reader or in 12-well plates at 37° C.

Protein preparation: The reporter construct was synthesized and cloned into pUC57 by GeneWiz. Construct was transferred from pUC57 into pGEX-6P (GE Healthcare Life Sciences) vector which contained an N-terminal GST tag for protein purification. GST tagged reporter protein was expressed in E. coli BL21 (DE3)—CodoPlus RIPL (Agilent technologies). Cells were lysed on an Emulsiflex C3 (Avestin) in buffer containing 20 mM Hepes (pH 7.4), 300 mM NaCl, 5 mM $MgCl_2$, 0.1 mM EDTA, 10% (vol/vol) glycerol, 5 mM DTT and 1% Triton X-100. Crude lysates were spun down at 35,000 g for 30 minutes. Clarified lysates were affinity purified using glutathione sepharose (GE Healthcare Life Sciences) and the GST tag was removed with Prescission Protease (GE Healthcare Life Sciences). A BSA protein assay was used to determine the concentration of the recombinant split luciferase protein (size: 95.3 KDa).

In vitro Luminescence assays: The luminescence reactions contained 20 mM Hepes (pH7.4), 100 mM NaCl, 5 mM $MgCl_2$, 5% (vol/vol) glycerol, 1 mM DTT, 3 mM ATP, 250 uM Coenzyme A hydrate (Sigma Aldrich). After adding specified concentrations of reporter protein and 2-5A (p2-5A$_3$, pA3), D-luciferin, Potassium salt (Gold Biotechnology) was added at a final concentration of 400 uM. The reactions were allowed to stabilize for 2 minutes and immediately after luminescence measurements were taken on a plate reader (Berthold Technologies). Acquisition time for the reaction was set to be 10 seconds.

2-5A extraction: HeLa cells treated for 6 hours with 1 ug/ml polyIC were lysed with RIPA (Thermo Fisher Scientific) buffer along with 0.5 mM PMSF protease inhibitor. The lysate was spun down at 12000 g for 10 minutes at 4° C. The supernatant was passed through a 3 KDa centrifugal filter to collect small nucleic acids. An equivalent amount of RNA from mock or polyIC treated sample was added to the luminescence assay. The RNA samples were tested for the presence of 2-5A with RNase L activation assay and radiolabeled RNA probes as described previously[31].

Western blot: The wild type (WT) or Mutant reporter sequence was transferred from pGEX.6P into pCDNA4.TO vector with an N-terminal FLAG tag. 24 hours after transfection, cells were lysed in sample buffer (NuPage), separated on 10% BisTris PAGE (NuPAGE), and transferred to PVDF membranes (Life Technologies). After 30 minutes blocking in 5% milk, the membranes were incubated with 1:2000 mouse anti-FLAG M2 (Sigma) or 1:5000 mouse anti-human GAPDH (Sigma) primary antibodies at 4° C. overnight. The membranes were then washed with TBST and incubated with horseradish peroxidase-conjugated anti-mouse secondary antibodies (1:10,000 Jackson ImmunoResearch) for 30 minutes. The membranes were washed again and detected with ECL Western Blotting Detection Reagents (GE Healthcare Life Sciences) on X-ray film.

Stable human cell lines expressing FLAG-V6 and FLAG V6-Y312A: For generating lentivirus, 293T cells were seeded into 6 well plates to achieve 50% confluency at 24 hours. Cells were transfected using FuGene with 1.5 µg pLEX.MCS (vector plasmid containing FLAG tagged WT or Y312A reporter), 1.33 µg pCMVdR8.91 (Gag-Pol packaging plasmid) and 0.17 µg pMD2.G (envelope plasmid). Lentivirus-containing medium was collected after 48 hours. Following collection, the medium was passed through 0.45 µm filter. Polybrene 5 µg/mL (f/c) and HEPES (pH 7.5; 100 mM f/c) were then added. HeLa cells at 40% confluence were infected with 600 µl of lentivirus-containing media in 10 cm dishes. The media was changed after 24 hours post-infection, and puromycin (1.5 µg/mL f/c) was added 3 days post-infection. Monoclonal cells were picked by limiting dilution. For HeLa cells, single cell clones were screened based on high fold-changes in reporter activity during poly-IC treatment. A549 cells at 90% confluency were plated in 24 wells and transduced with 200 µl lentivirus. 48 hours post transduction, media containing 2 µg/mL puromycin was added. After 72 hours of selection, surviving cells were plated by limiting dilution to pick single clones. For A549 cells, single cell clones were screened by western blotting with anti-FLAG M2 (Agilent).

Reporter assay in live cells: NLS and NES tag sequences cloned in the reporter immediately following the FLAG tag were PKKKRKVE (SEQ ID NO: 4) and LQLPPLERLTLD (SEQ ID NO: 5), respectively. HeLa cells were seeded at a cell density of $2 \times 10^5$ cells per well on 96 well plates. These 96 well plates were clear bottom and white for optimum luminescence readings. After the cells adhered to the plates (in approximately 6 hours), V6 or Y312A V6 (with or without localization tags) constructs were transfected using Lipofectamine 2000. 24 hours after transfection, the cells were pre-treated with 100 uM D-luciferin ethyl ester (1% DMSO) (f/c) (Marker Gene Technologies). After one hour of substrate pre-treatment, pIC-lipo complexes were added to the cells along with a second addition of 100 uM D-luciferin substrate. Luminescence measurements were taken on Repeated mode in the plate reader: every 15 minutes for the course of three hours. Luminescence acquisition time: 1 minute/well.

Immunofluorescence microscopy: HeLa cells were seeded in 8-chamber wells (NUNC™ LAB-TEK™ Chambered Coverglass) at 60% confluency. 24 hours after reporter construct transfection, HeLa cells were fixed with 4% paraformaldehyde for 15 minutes at room temperature. Samples were permeabilized with 0.1% Triton for 20 minutes at room temperature. Blocking was carried out with 20% goat serum for 1 hour at 4° C. The samples were then incubated with 1:400 mouse anti-FLAG M2 (Sigma) primary antibodies for 2 hours at 4° C. The samples were rinsed 3 times with PBS and incubated with Alexa Fluor 488 goat anti mouse (1:400). Samples were imaged with widefield microscope according to the standard protocol.

Results

Figure 2A:
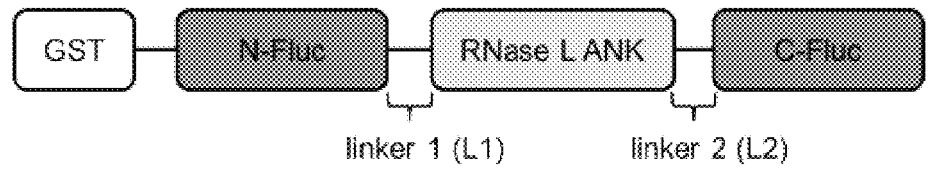
FIGS. 2A-2B. Dependence of linker lengths on reporter activity.
Figure 2B:
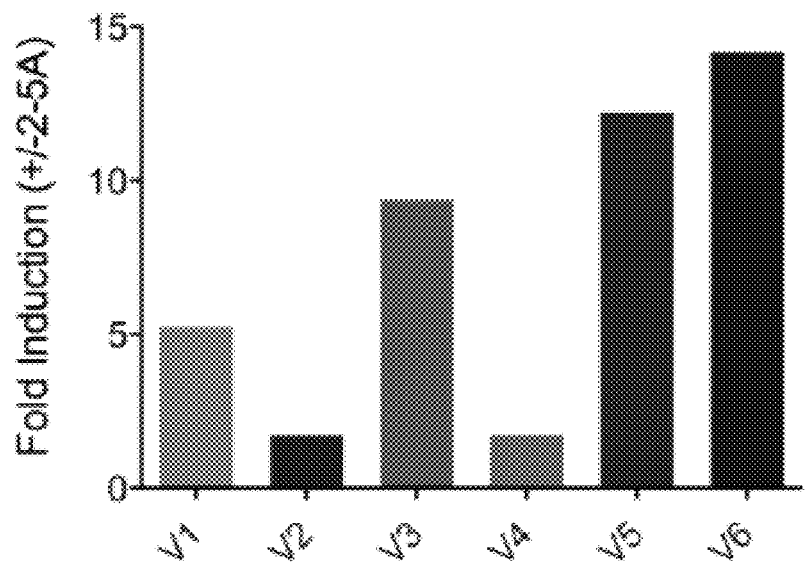

N-terminus firefly luciferase residues 1-416 and C-terminus firefly luciferase residues 417-500 (NFluc1-416/CFLuc417-500) were chosen as the split fragments tethered to the RNase L ANK domain via linkers on either side. This split site was previously reported to give high absolute signal but near zero self-complementation signal[32]. The linker lengths on either side of the ANK domain were manipulated and tested six different constructs (V1 through V6) for their signal to noise ratio (FIG. 2A). In vitro assays determined that the reporter was sensitive to changes in linker length. Among the different constructs, V6 construct with (GGGS)$_3$ (SEQ ID NO: 3) as linker 1 and (GGGS)$_2$ (SEQ ID NO: 2) as linker 2 gave the best signal to noise ratio in the assay and is used for all further characterizations (FIG. 2B). Finally, to account for background luminescence, another version of the reporter harboring a Y312A mutation in the ANK domain was generated which is sufficient to abolish 2-5A binding and RNase L activation[27].

Figure 3A:
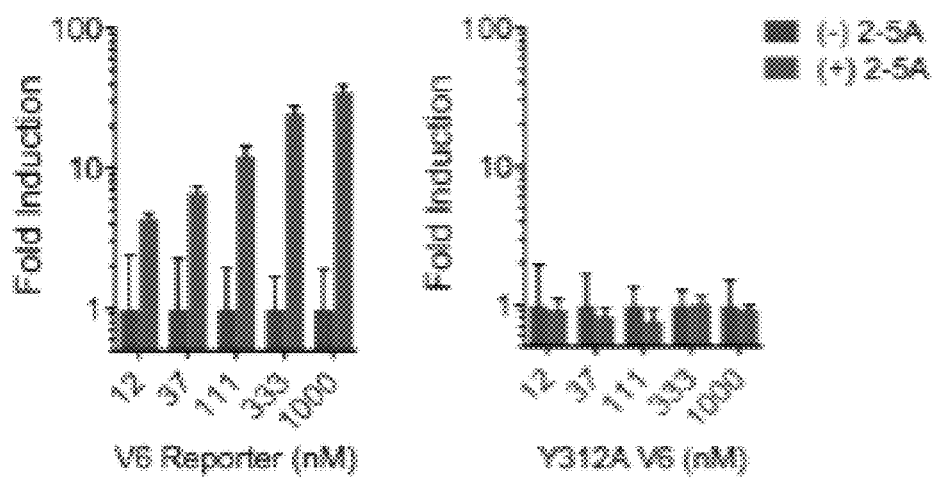
FIGS. 3A-3D. Biochemical assays verify that the reporter can detect 2-5A in vitro.
Figure 3B:
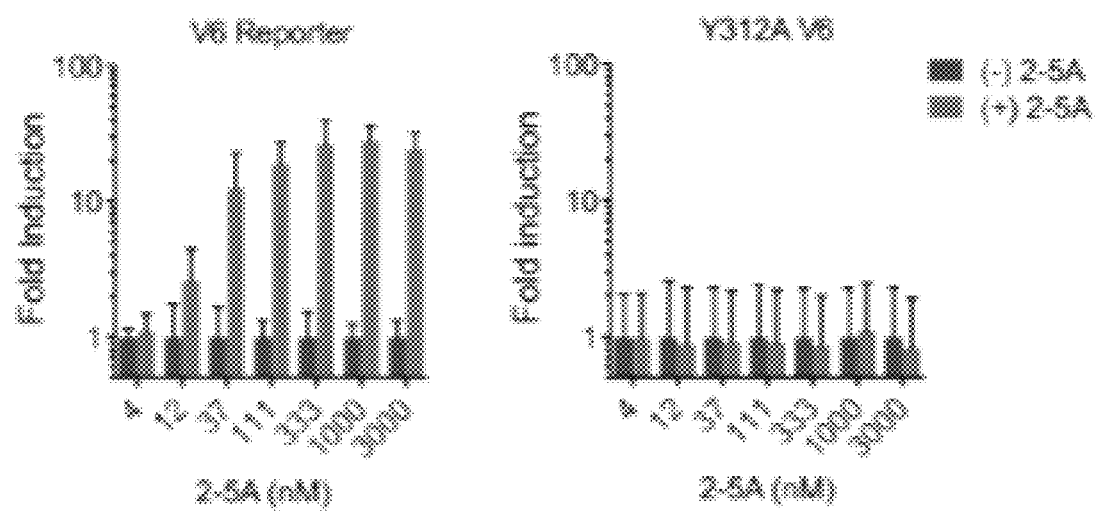

To first test the reporter in a proof-of-concept luminescence assay, V6 or Y312A V6 control reporter protein was titrated in the presence of saturating 2-5A (pA3=1 µM). Increasing V6 reporter protein concentration showed increases in fold change luminescence with 2-5A versus without 2-5A. The Y312A V6 control did not respond to 2-5A at any of the concentrations tested as expected (FIG. 3A). Next, luminescence was measured by titrating in 2-5A and using a fixed concentration of the V6 or Y312A V6 control reporter (200 nM). The V6 reporter protein was sensitive to nanomolar concentrations of 2-5A and showed increases in fold change luminescence with increasing 2-5A concentrations while the control reporter remained inactive (FIG. 3B).

Figure 3C:
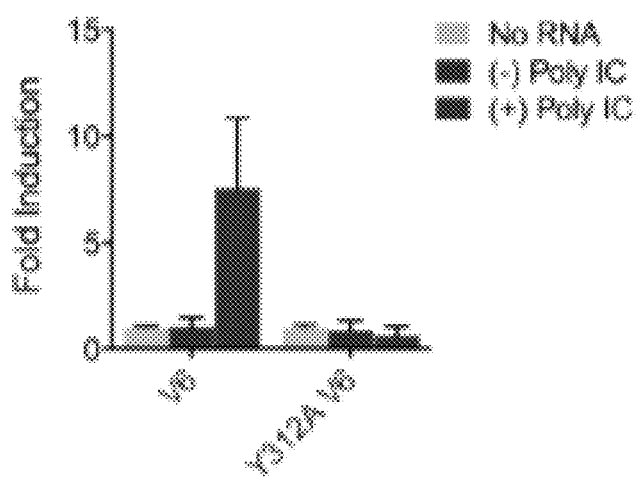
Figure 3D:
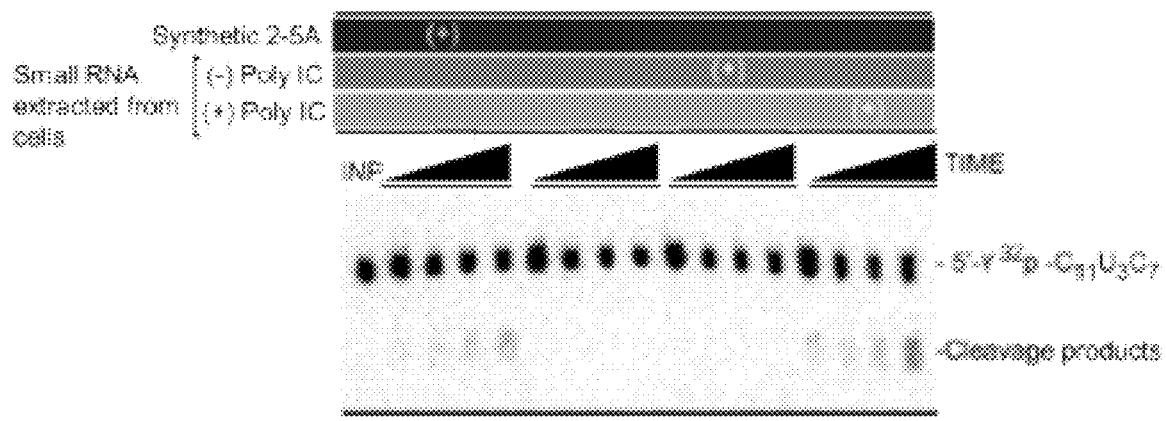
Figure 4A:
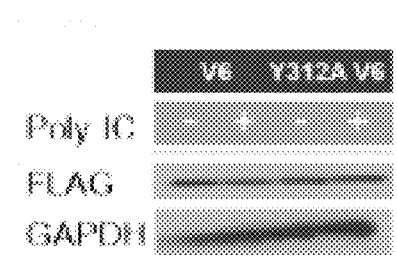
FIGS. 4A-4C. Real time measurement of 2-5A in poly IC treated cells.
Figure 4B:
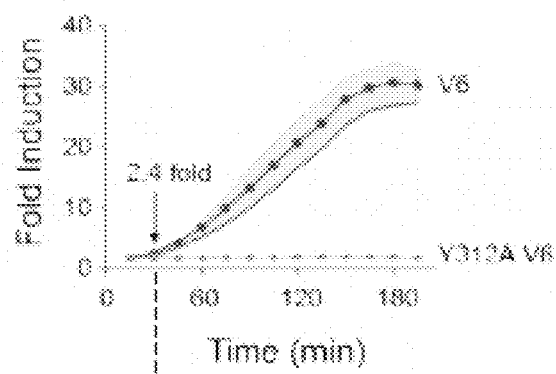
Figure 4C:
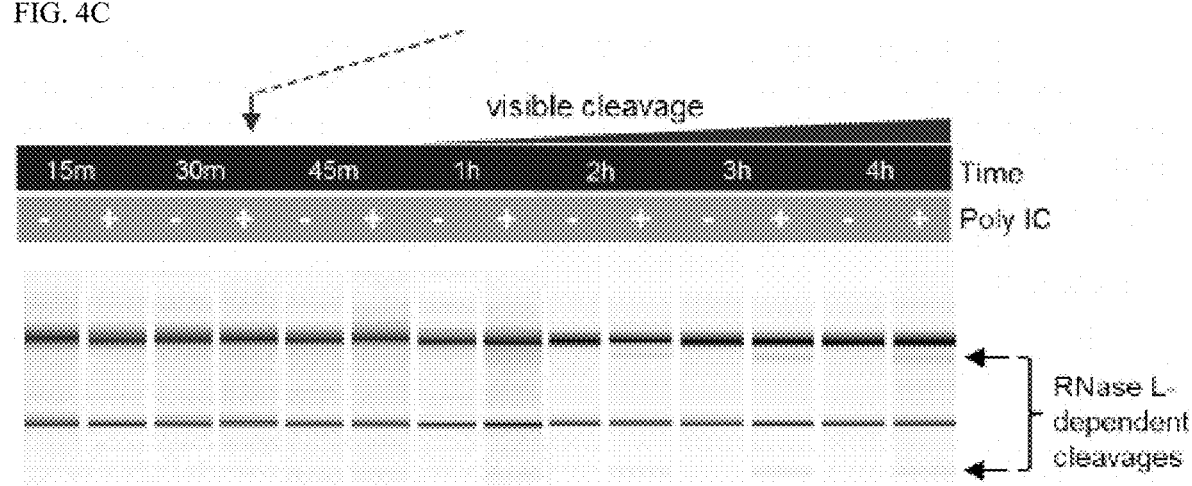
Figure 5A:
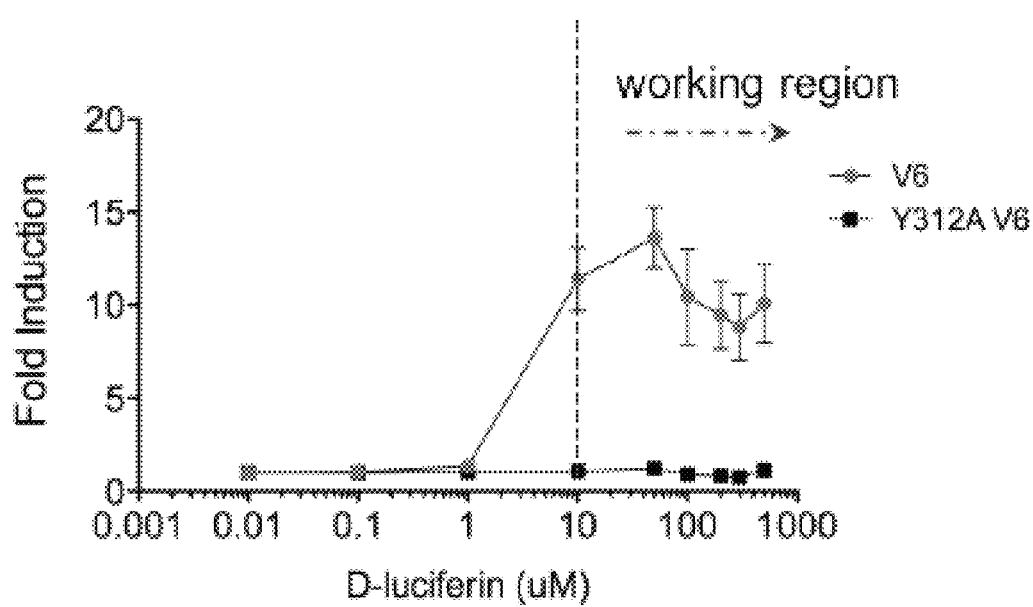
FIGS. 5A-5B. Dose Titrations.
Figure 5B:
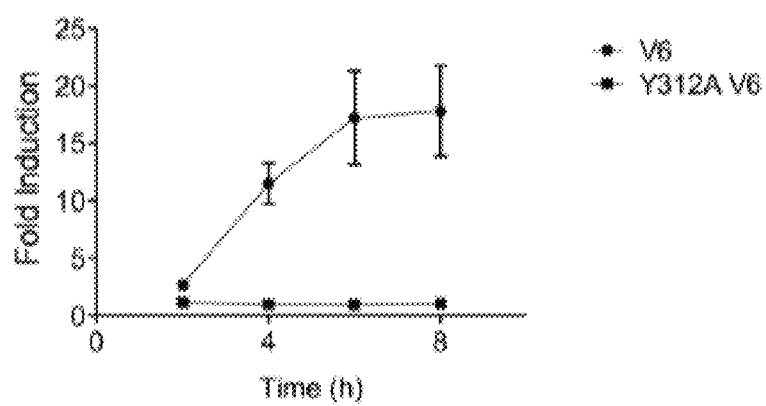

In order to test if the reporter could detect cellular 2-5A that is naturally synthesized in response viral infections, HeLa cells were transfected with poly IC for 6 hours to mimic a viral infection. The cells were harvested and the cell lysate was passed through a 3 kDa cut-off centrifugal filter to isolate and purify only small nucleic acids which were tested for their ability to activate the reporter in vitro. Nucleic acids derived the poly-IC treated cells, but not mock treated cells, stimulated the reporter roughly 8-fold, suggesting 2-5A was synthesized in response to poly IC (FIG. 3C). The reporter V6 had sufficient sensitivity to detect low amounts of 2-5A purified from human cells treated with poly-Inosine/poly-Cytidine (poly-IC) dsRNA. The presence of 2-5A in this sample was confirmed by testing its ability to activate recombinant RNase L directly. Indeed, the small nucleic acids that activated the reporter also activated recombinant RNase L as seen by cleavage of a radiolabeled RNA substrate by RNase L (FIG. 3D). These reporter measurements closely agreed with the standard endoribonuclease readout based on RNA cleavage After verifying that the reporter responds to 2-5A in biochemical assays, the reporter's ability to detect 2-5A in live cells was tested. FLAG-tagged V6 or Y312A V6 reporter constructs were expressed in HeLa cells and 24 hours later confirmed expression by western blot (FIG. 4A). Reporter expressing cells were pretreated with 100 µM membrane permeable D-luciferin ethyl ester for one hour followed by poly IC transfection (FIG. 4B). The optimum dose of luciferin substrate was determined by dose titration, FIG. 5A. To ensure that the substrate was present in excess and that the signal would not be affected by consumption of substrate, luciferin substrate was added again immediately following poly IC treatment. Cells expressing the mutant reporter did not respond to poly IC over the course of time. With V6 reporter expressing cells, a slight initial lag time in signal was observed indicating poly IC entry. 2-5A build-up was observed as early as 30 minutes (2.4 fold with the V6 reporter in poly IC treated vs untreated cells) with a maximum fold change of 30 units 3 hours post poly IC treatment (FIG. 4A). In contrast, 28S rRNA cleavage in the L1 stalk was absent after 30 minutes and faint products appeared only 1 hour after poly IC treatment, and further increased after 3 to 4 hours (FIG. 4C). This indicates that 2-5A response as shown by the reporter is a fast acting response. Even though RNase L activation might be occurring rapidly as well, the enzyme has to cleave enough rRNA substrate for cleavage products to appear on the gel. Endpoint measurements were taken for up to 8 hours for 2-5A levels in cells treated with poly IC. It was observed that even up to 8 hours, there is a lack of negative regulation in 2-5A levels in cells treated with poly IC (FIG. 5B). This contrasts with a previous study carried out in extracts where 2-5A levels were found to decrease 60 minutes post poly IC treatment[33]. HeLa cells expressing control FLAG-V6-Y312A produced no increase in luminescence, confirming that WT V6 detects cellular 2-5A in real time.

Figure 6A:
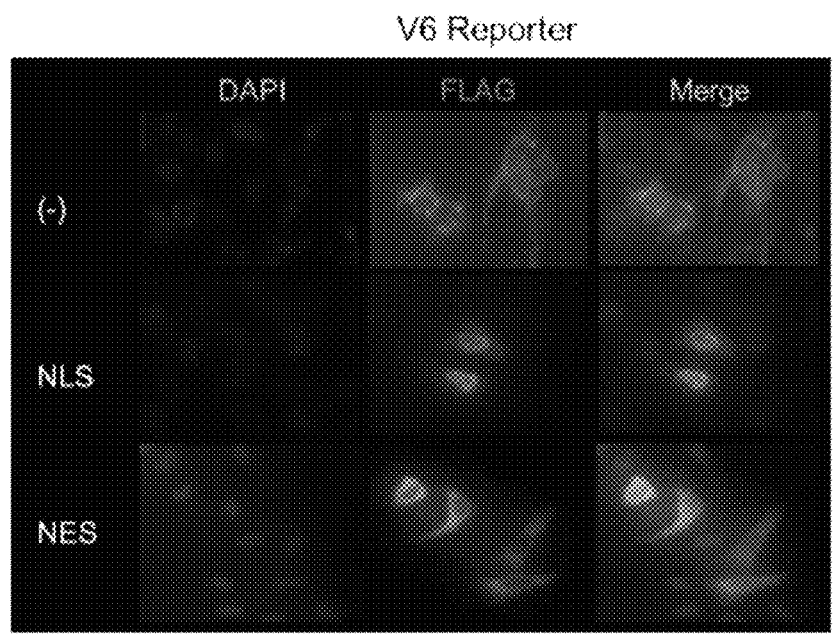
FIGS. 6A-6C. 2-5A levels in nuclear/cytoplasmic compartments.
Figure 6B:
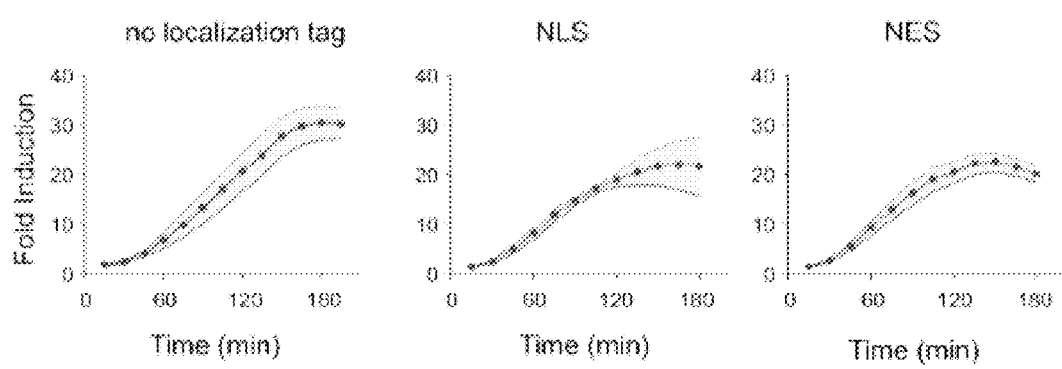
Figure 6C:
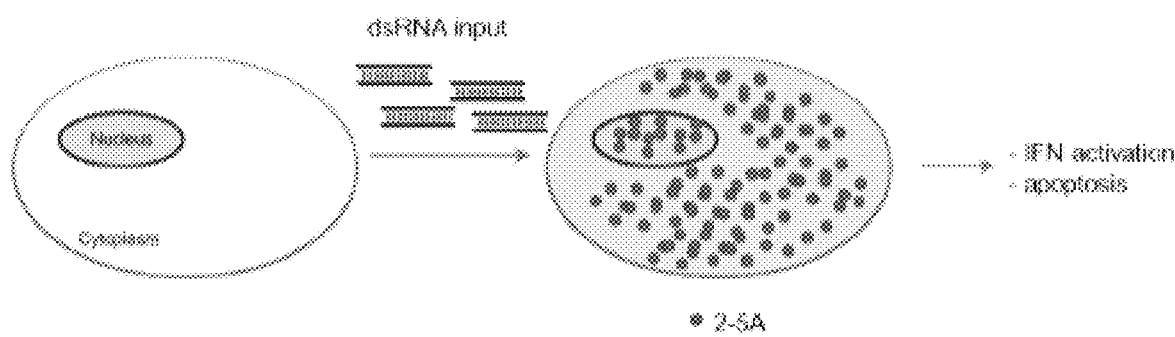

Even though OASs have been thought to be predominantly cytosolic to survey for the presence of dsRNA, a few reports have shown that in interferon treated cells, OASs can be localized to different sub-cellular compartments including nuclear, peri-nuclear space and mitochondria[34,35]. In order to probe whether a 2-5A response is called for in the nucleus and also to understand the dynamics of 2-5A build-up in the nuclear versus cytoplasmic compartment, nuclear localization and nuclear export signal (NLS/NES) tags were added to the reporter. With immunofluorescence microscopy, the localization of the NLS/NES tagged reporters in their respective compartments was confirmed. The V6 reporter with no tag behaved similarly to the NES construct in that it was predominantly localized in the cytoplasm (FIG. 6A). Upon poly IC addition, light signal was observed in cells expressing the NLS construct confirming the presence of 2-5A in this subcellular compartment. However, the dynamics of 2-5A build-up is similar in nuclear versus cytoplasmic compartment (FIG. 6B), inferring that regardless of where dsRNA sensing by OASs take place, 2-5A molecules calling for RNase L action, are available early on in both nuclear and cytoplasmic compartments. Indeed, 2-5A produced at the center of a HeLa cell, may take only several seconds to diffuse across the nucleus, through the nuclear pores, and to become evenly distributed between the nucleus and the cytosol (FIG. 6C). These measurements did not support localized 2-5A action and indicated that 2-5A was poised to establish communication between the OASs and RNase L across the cell.

Figure 7:
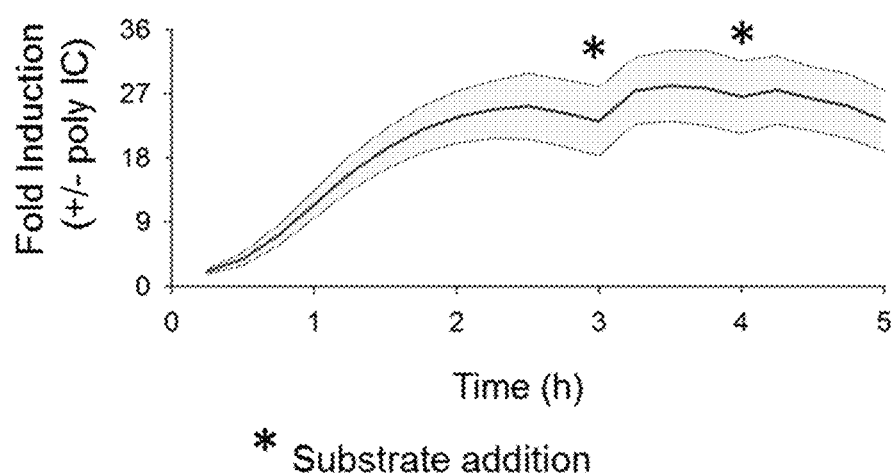
FIG. 7. Analysis of HeLa cells stably transduced with a lentiviral construct containing the reporter. Luminescence measurements were taken on Repeated mode every 15 minutes for the course of three hours. Luminescence acquisition time: 1 minute/well. Data is presented as fold change with poly IC vs without poly IC.

In an additional experiment, HeLa cells were stably transduced with a lentiviral construct containing the reporter. A monoclonal population of reporter expressing cells was then selected by limiting serial dilution. For reporter assay, these monoclonal cells were seeded at a cell density of $2 \times 10^5$ cells per well on 96 well plates. After the cells adhered to the plates (in approximately 6 hours), the cells were pre-treated with 100 uM D-luciferin ethyl ester (1% DMSO) (f/c). After one hour of substrate pre-treatment, poly IC-Lipofectamine complexes were added to the cells along with a second addition of 100 uM D-luciferin substrate. Luminescence measurements were taken on Repeated mode in the plate reader: every 15 minutes for the course of three hours. Luminescence acquisition time: 1 minute/well. Data is presented as fold change with poly IC Vs without poly IC (FIG. 7). Upon poly IC treatment, 2-5A build-up is observed as early as 30 mins (3.7 fold) with a maximum fold change of 28 units 3.5 hours after poly IC treatment. To ensure that the signal does not decrease due to substrate consumption, substrate was added at 3 and 4 hours after poly IC addition.

Through proof of concepts experiments, it was verified herein that the reporter is amenable for use in biochemical assays and in live cells. The potential high-throughput nature of this technology can be harnessed to screen for small molecule modulators of the 2-5A/RNase L axis. Aside from being antiviral, activators of the pathway have the potential to be chemotherapeutic if they induce dsRNA in cells. DNA methyltransferases, for example, have been shown to be potent anti-cancer drugs because they induce endogenous dsRNA hence activating toxic cellular antiviral programs[11]. As RNase L is also pro-apoptotic, it may be predicted that drugs leading to 2-5A synthesis would be toxic and effective in killing target cells. Conversely, the reporter can also be used to screen for drugs that dampen dsRNA led 2-5A responses which can be useful for autoimmune diseases caused due to immune-reactive self-dsRNA. The reporter can be used for profiling different viruses based on their 2-5A response and for diagnostic purposes to test patient samples for viral infections or inflammatory stress responses. Use of this reporter in in vivo models of diseases will radically transform the understanding of RNase L signaling and offer new possibilities to understand the role played by dsRNA/RNase L in the innate immune system.

Example 2—Measurement of IFN Response

The pathways of 2-5A and IFNs are closely interconnected. IFNs stimulate 2-5A production by transcriptionally inducing the OASs (Wreschner et al., Nature 289, 414-7 (1981), West et al., Mol Cell Biol 2, 1436-43 (1982); Stark et al., Nature 278, 471-3 (1979)). Conversely, 2-5A can amplify (Malathi et al., Nature 448, 816-9 (2007)) and suppress (Banerjee et al., MBio 5, e00856-14 (2014)) IFN-β protein production. Considering that RNase L stops translation and ultimately causes apoptosis38, IFNs may critically require mechanisms to delay RNase L activation and evade RNase L. To test whether such mechanisms exist, stable A549 and HeLa human cell lines that carry FLAG-V6 were generated and used these cells to measure 2-5A synthesis throughout dsRNA response.

Methods

Live cell 2-5A measurements in stable cell lines expressing V6 or V6-Y312A reporters: A549 or HeLa cells stably expressing V6 or V6-Y312A control reporters were seeded at a density of $1 \cdot 10^4$ /well on TC-treated, clear flat bottom white 96-well plates. Before transfection with poly-IC, cells were pre-treated with 100 µM D-luciferin ethyl ester (1% DMSO) (f/c) (Marker Gene Technologies). After one hour of substrate pre-treatment, a poly-IC/lipofectamine complex (1 µg/mL Poly-IC+0.5 µL Lipofectamine 2000 in a final volume of 100 µL) was added to the cells along with a second addition of 100 µM D-luciferin and HEPES (pH 7.5; 20 mM f/c). Dilutions of poly-IC were made by diluting the poly-IC/lipofectamine complexes. Luminescence measurements were taken in repeat-mode using plate reader at time intervals shown on the figures. After three hours, fresh D-luciferin ethyl ester (100 µM) was re-supplied at every hour to ensure excess reporter substrate. Luminescence acquisition time was one minute per well. For IFN-β pre-treatment, a dose of 1000 U/mL (f/c) was used 24 hours before poly-IC treatment.

qRT-PCR analysis: Cells were harvested in 350 µL RLT buffer (Qiagen) and RNA was purified according to the RNeasy protocol (Qiagen). cDNA was prepared using oligo-dT and a High Capacity RNA to cDNA kit (Applied Biosystems). qPCR was performed using the Power SYBR green PCR mix in a 96 well format on StepOnePlus qPCR instrument (Life Technologies). qPCR primers used in this work were from Integrated DNA Technologies and are available via the manufacturer if not specifically recited in the Table below.

| qPCR Primers used | | | | |
|---|---|---|---|---|
| Gene | Forward | SEQ ID NO: | Reverse | SEQ ID NO: |
| MDA5 | GCTTCT AGTTAG | 6 | CTTACACCTG ATTCATTTCC | 7 |
| RIG-I | AGGAAC TGGAGC | 8 | AGACTCTCTG TGTCCCTCAT | 9 |
| ACT B | CACTCT TCCAGC | 10 | GTACAGGTCT TTGCGGATG | 11 |

OAS1 Hs.PT.58.19958183
OAS2 Hs.PT.58.24570700
OAS3 Hs.PT.58.45631304
OASL HS.PT.58.50426392

Ribopuromycilation and $^{35}$S labeling to monitor nascent translation: To generate puromycin-tagged nascent peptides, human cells were treated with 0.1-1 µg/mL of poly-IC for times specified on the figures, after which the growth media was supplemented with 10 µg/mL puromycin (Invitrogen). Puromycin pulse lasted for 5 min. Cells were trypsinized and harvested in NuPAGE LDS sample buffer for western blot analyses. Proteins were separated by 10% BisTris PAGE (NuPAGE), and transferred on PVDF membranes (Life Technologies). The membrane was stained with Ponceau to normalize for sample loading, then washed and blocked with 5% non-fat dry milk in TBST buffer. The membranes were probed with 1:1000 mouse anti-puromycin antibody (EMD Millipore) that binds to de novo synthesized proteins, followed by horseradish peroxidase-conjugated goat anti-mouse secondary antibody (1:10,000, Jackson ImmunoResearch). Metabolic labeling with $^{35}$S was conducted using the following procedure. After cell treatment with poly-IC, media was changed to methionine-free RPMI+10% FBS supplemented with 11 µCi EASY TAG™ EXPRESS35S Protein Labeling Mix (Perkin Elmer). Cellular proteins were resolved by 10% BisTris PAGE (NuPAGE) and analyzed by phosphorimaging.

Secreted IFN detection by qPCR in conditioned media: A549 WT and RNase L knock out (KO) cells in 12-well plates were transfected with 1 µg/mL poly-IC and lipofectamine 2000 for 0.5, 2 or 6 hours. At the end of the time course, cells were washed four times with 1 mL of growth medium (RPMI+10% FBS) to remove residual poly IC. After the washes, fresh 1 mL medium was added and the cells were kept in fresh media for one hour to allow for protein secretion. Treatments of naive cells with conditioned media were done in a separate 12-well plate and using cells seeded 1 day before the analysis. Naïve cell media was replaced with 1 mL of the conditioned medium from above. Cells were grown in the conditioned media for 16 hours and harvested in 300 µL RLT (Qiagen). For pulse-chase experiments in FIG. 9C, 10 µM anisomycin was added 3 hours after poly-IC addition. Anisomycin level was additionally maintained during the last hour allocated for IFN secretion into fresh media. To exclude a possible inhibitory effects of anisomycin on IFN response (FIG. 9D), WT cells were treated for 16 hours with 1000 U/mL recombinant IFN-β in plain or conditioned media.

RNA-seq: Poly-A+ RNA sequencing was conducted and processed as described previously18,46. The datasets (FIG. 9C) were deposited to GEO database under accession number GSE120355.

Reporter assay to detect type-I and type-III IFNs: Previously developed reporter cell lines, which are selectively sensitive to either human type I (Huang et al., Proc Natl Acad Sci USA 104:9822-7 (2007)) or type III (Kotenko et al., Nat Immunol 4:69-77 (2003)) IFNs, were used to detect the presence of IFNs in the media. Briefly, $4 \times 10^6$ cells were treated with each sample and incubated at 37° C. for 20 min. The cells were then washed with PBS, lysed and analyzed by immuno-blotting with antibodies specific for phosphorylated STAT1 (pSTAT1; BD clone 14/P STAT1 (RUO)).

Media antiviral activity assay: Equal numbers of human retinal pigment epithelial ARPE-19 cells were plated in all wells of a 96 well plate on day 1. On day 2, the cells were then treated with 3-fold serial dilutions of samples, starting from the first wells on the left to the last wells on the right. The cells were then incubated for 24 hours to allow induction of IFN response and then challenged with vesicular stomatitis virus, keeping the virus concentration constant in all wells ($1 \cdot 10^3$ PFU/well). The virus-treated cells are then incubated for 48 hours and the cells not killed by the virus are visualized by staining with crystal violet.

Diffusion calculations: First, diffusive relaxation rate was estimated in a simplistic cell without the nucleus. This will define how fast a non-uniform concentration of 2-5A should relax in a sphere the size of a cell. The slowest mode to relax will be the spherically symmetric one with a single peak at the cell center, and zero gradient at the cell membrane (reflecting boundary conditions). The diffusion equation with no sources or sinks is: $\partial c/\partial t = D \cdot \nabla^2 c$, which in the case of spherical symmetry simplifies to $\partial c/\partial t = D \cdot (1/r^2) \cdot \partial/\partial r (r^2 \cdot \partial c/\partial r)$. This simplifies further if the substitution is made: $c=u/r$, and use $\partial c/\partial r = (1/r) \cdot \partial u/\partial r - (1/r^2) \cdot u$ and $\partial c/\partial t = (1/r) \cdot \partial u/\partial t$, yielding $(1/r) \cdot \partial u/\partial t = D \cdot [(1/r^2) \cdot \partial/\partial r (r \cdot \partial u/\partial r - u)]$, and finally $\partial u/\partial t = D \cdot \partial^2 u/\partial r^2$. One can expand u in eigenfunctions of the right hand side, which are just sines and cosines, and the general solution for u(r,t) will be of the form: $u(r,t) = \Sigma u_k \cdot \sin(k \cdot r) \cdot \exp(-\lambda_k \cdot t)$ plus similar terms for cosines.

Rather than solving for complete generality, it was noted that you want the slowest decaying mode for which c is finite at r=0 (eliminating cosines), and has a no-flux boundary condition at the sphere's radius R. No flux at R implies $\partial c/\partial r=0$, which implies that $\partial u/\partial r \cdot (1/u)=1/r$ at r=R. Therefore, k·cos (k·R)/sin(k·R)=1/R, i.e. tan(k·R)=k·R, and it is needed to solve this equation to obtain k. The lowest-k solution (slowest mode of diffusion) is k·R=4.49. After defining k*=4.49/R, the corresponding relaxation rate of this mode is found from the diffusion equation: $(-\lambda_{k*}) \cdot u = -D \cdot k^{*2} \cdot u$, so that $\lambda k^* = D \cdot k^{*2}$.

Up to this point, the calculation has neglected contributions to the solution for u(r,t) that are zero when acted on by $\nabla^2$, so we can add terms $c_0(t) \cdot r$ or $c_1(t)$ to u(r,t), or equivalently terms $c_0(t)$ or $c_1(t)/r$ to c(r,t). Only the constant term satisfies continuity at the center of the sphere for c(r,t), as well as zero flux at the boundary, and this constant term does not decay in time. So the solution for c(r,t) at long times has the form: $c(r,t)=c_0+(c^*/r) \cdot \exp(-\lambda_{k*} \cdot t) \cdot \sin(k^* \cdot r)$. It approaches the constant $c_0$ at very long times, with the leading spatially non-uniform term decaying at a rate: $\lambda_{k*}=D \cdot k^{*2}=D \cdot (4.49/R)^2$.

A HeLa cell radius (R) is $\sim 20 \cdot 10^{-4}$ cm. Diffusion coefficients of small macromolecules (<10 kDa) in the HeLa cytosol and nucleus are ~0.2 of diffusion in free buffer49 and for 2-5A (~1-2 kDa) are extrapolated as ~0.2·5·$10^{-6}$ cm$^2$/s=$10^{-6}$ cm$^2$/s. These parameters imply a rate constant $\lambda_{k*}=D \cdot (4.49/R)^2=10^{-6} \cdot (4.49/20 \cdot 10^{-4})2=5$ s$^{-1}$, or a relaxation time of approximately 0.2 s.

To evaluate how the nuclear envelope changes the relaxation rate between cytoplasm and nucleoplasm, we need to examine the ratio of the sum of circumferences of the nuclear pores to the circumference of the nucleus (Zarnitsyn et al., Biophys J 95:4124-38 (2008)). This ratio is given by pore diameter times number of pores divided by nuclear diameter: 5.2 nm×2000/20 microns≈0.5. From the calculations of Zarnitsyn et al. for transport through a collection of pores contained within a disc-shaped region in a flat sheet, the above value of 0.5 corresponds to transport at ~25% of the free diffusion limit. Therefore, in the presence of the nuclear envelope, is it estimated that the net relaxation rate will be ~0.25·$\lambda_{k*}$~1 s$^{-1}$, corresponding to a relaxation time of 2-5A between nucleus and cytoplasm of 1s.

Results

Figure 8B:
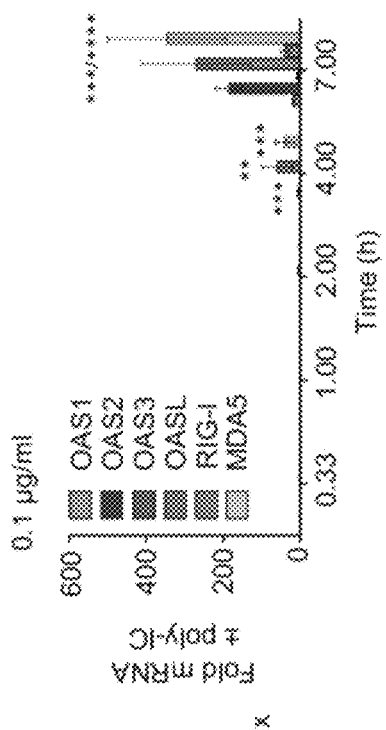
FIGS. 8A-8G Dynamics of 2-5A, transcriptional IFN response and translation in A549 cells.
Figure 8A:
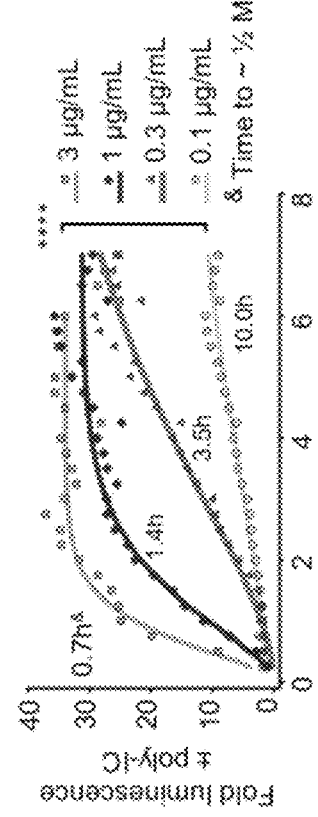
Figure 8C:
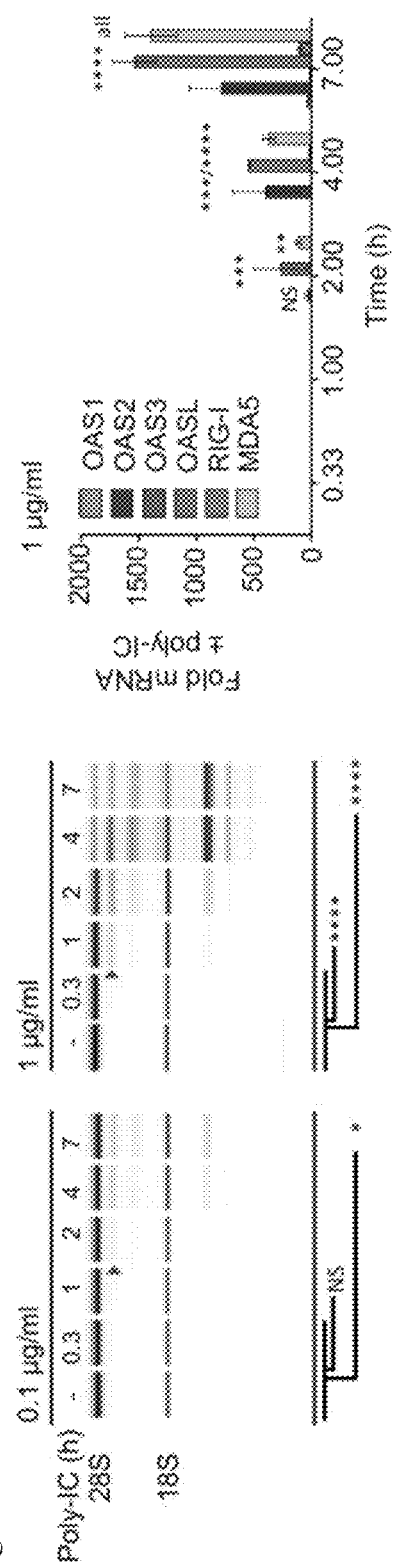
Figure 8D:
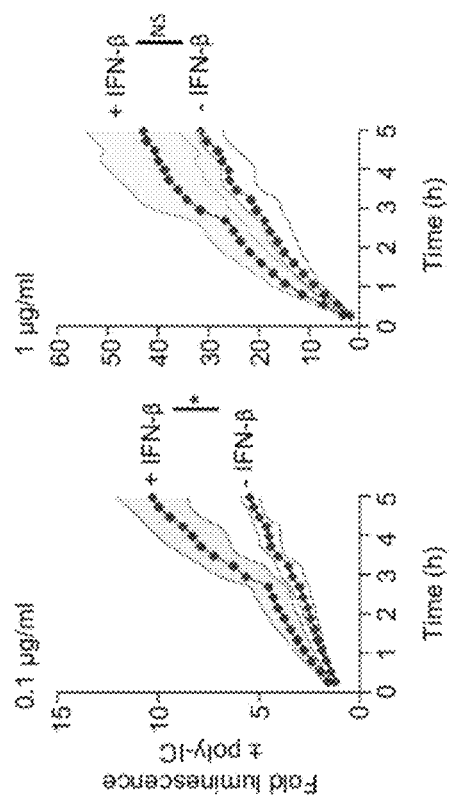

Time-dependent 2-5A synthesis was readily observed over a range of poly-IC concentrations (FIG. 8A). Accumulation of 2-5A started nearly immediately after dsRNA addition, exhibiting a discernible lag at low doses and no lag at higher doses of poly-IC. In contrast, transcription of IFN stimulated genes (ISGs) measured by qPCR of OAS1/2/3/L and the helicases RIG-I and MDA5, developed with a lag of 2-4 hours and became strong after maximal 2-5A production (FIGS. 8, A and B). Rapid 2-5A synthesis before the IFN response was confirmed by cleavage of 28S rRNA in A549 cells (FIG. 8C), and in HeLa cells using a combination of biosensor and qPCR readouts. These observations suggest that 2-5A production may precede the IFN response and that 2-5A is supplied by basal rather than IFN-induced OASs. Therefore, 2-5A/OAS activation does not require IFN stimulation, as reported (Sadler et al., Nat Rev Immunol 8:559-68 (2008)). Similarly, basal OASs are solely responsible for protection of mouse myeloid cells from murine coronavirus (Birdwell et al., J Virol 90:3160-72 (2016)). It was also found that the OAS/RNase L activation was not inhibited by pre-treatment with a transcription inhibitor Actinomycin D and priming the cells with IFN-β had only a modest ≤2-fold effect on 2-5A synthesis while a strong overall transcriptional response was present (FIG. 8, D to E). These data further support the involvement of the basally expressed OASs in 2-5A production, prior to ISG transcriptional response.

Figure 8F:
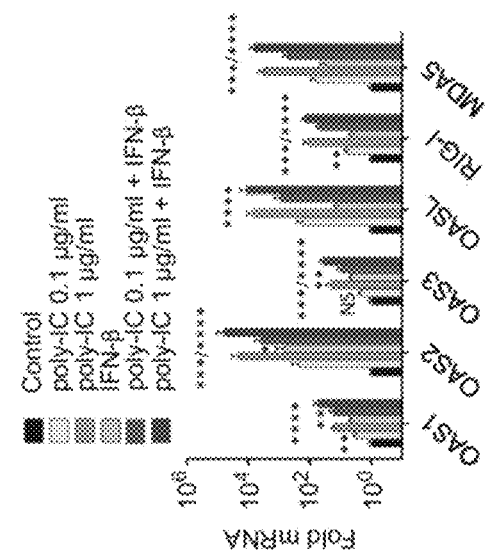
Figure 8E:
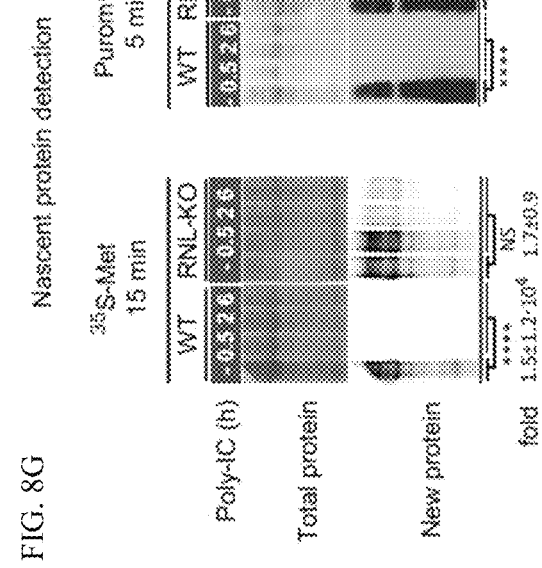
Figure 8G:
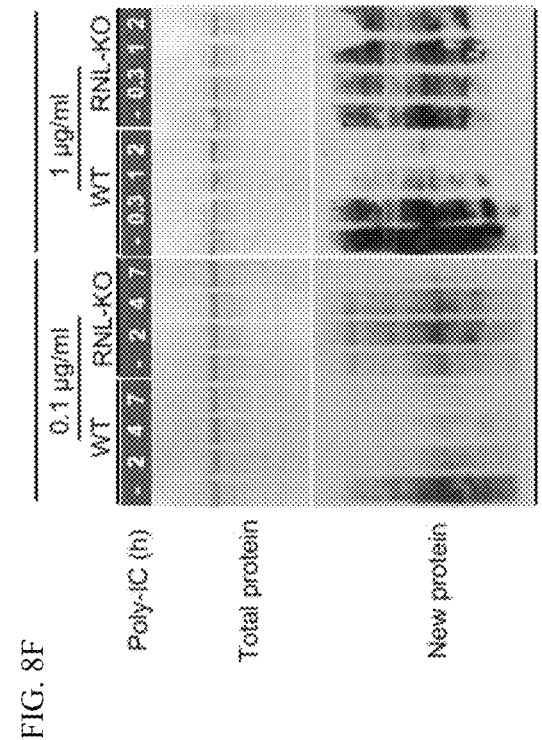

To determine whether cellular 2-5A dynamics corresponds to a rapid arrest of translation by RNase L, nascent protein synthesis was measured by puromycin pulse labeling in WT and RNase L−/−A549 cells (Donovan et al., RNA 23:1660-1671 (2017)). Treatment of WT, but not RNase L−/− cells with poly-IC halted global translation before ISG induction (FIGS. 8F and 8B). RNase L−/− cells exhibited a delayed and incomplete translational attenuation, presumably due to PKR. Translational arrest ahead of ISG induction was also present in HeLa cells. Disengagement of basal protein synthesis before the IFN response was further confirmed using metabolic labeling of nascent proteome with 35S (FIG. 8G).

IFNs β and λ escape the translational shutoff caused by 2-5A: 2-5A rapidly stops cell-wide protein synthesis. To examine IFN protein production under these conditions, we treated WT and RNase L−/− cells with poly-IC and assayed the media for IFN activity (FIG. 9A). These tests revealed a time-dependent increase of media antiviral activity and media ability to induce ISGs, which developed after RNase L-mediated translational arrest (FIG. 9B). At time points well beyond translational arrest, we observed an increase in antiviral activity (FIG. 9C) and ISG induction by two orders of magnitude from media of poly I:C-treated WT and RNase L−/− cells (FIG. 9D). In agreement with the ISG induction readout, media from WT and RNase L−/− cells exhibited comparable antiviral activity and similar time-dependent increase of IFN potency. These data suggest that shutdown of bulk translation by RNase L thus does not inhibit IFN production.

To test whether IFN arises from actively ongoing translation rather than from other potential mechanisms (e.g. delayed secretion of pre-translated IFN stores), pulse-treatment with a translation inhibitor, anisomycin (FIG. 9E) was used. In this setting, cells were first treated with poly-IC for three hours, which stopped protein synthesis but did not yet activate a strong transcriptional IFN response. Next, anisomycin was added to arrest all protein synthesis and the cells were kept for three additional hours. Control cells were kept for the same duration without anisomycin. During the last hour, media was changed to remove poly-IC, but anisomycin treatment was continued to keep the cells translationally arrested. When IFN activity in the media was assayed, it was found that anisomycin treatment after the 2-5A-induced global translational inhibition, but before the IFN response, blocked IFN production (FIG. 9E). A control experiment showed that anisomycin was compatible with IFN sensing by naïve cells (FIG. 9F). Of note, anisomycin had a mild stimulatory effect on ISG mRNAs due to an unknown mechanism; this effect acted in the opposite direction from blocking IFNs and thus did not affect the suitability of anisomycin as a control in our tests. Together, our experiments indicated that IFNs are indeed translated when the bulk of protein synthesis remains silenced by 2-5A.

Figure 10A:
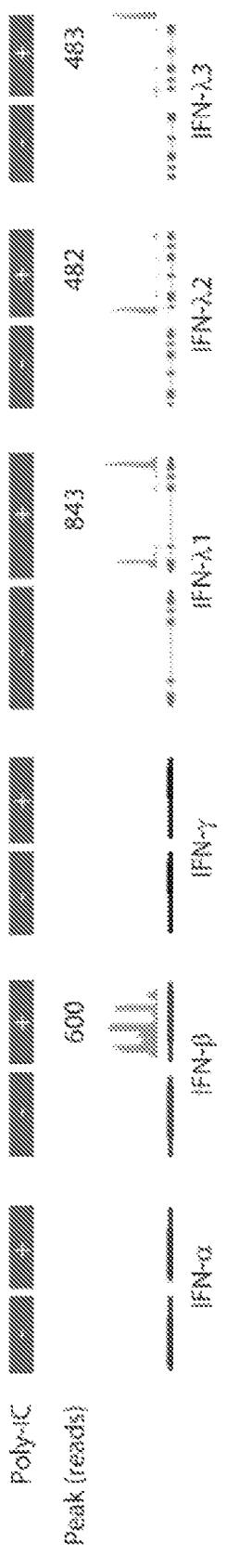
FIGS. 10A-10C Type-I and type-III IFNs escape RNase L.
Figure 10B:
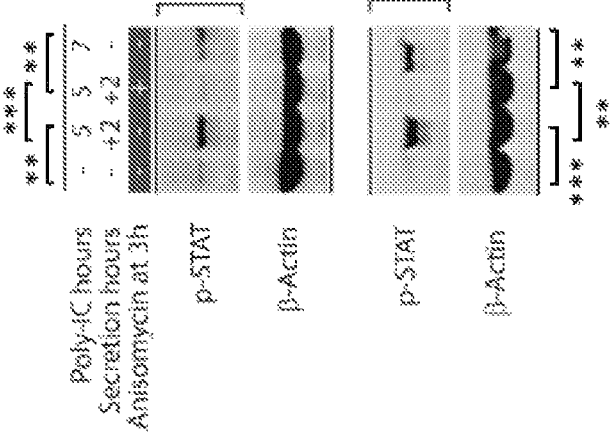
Figure 10C:
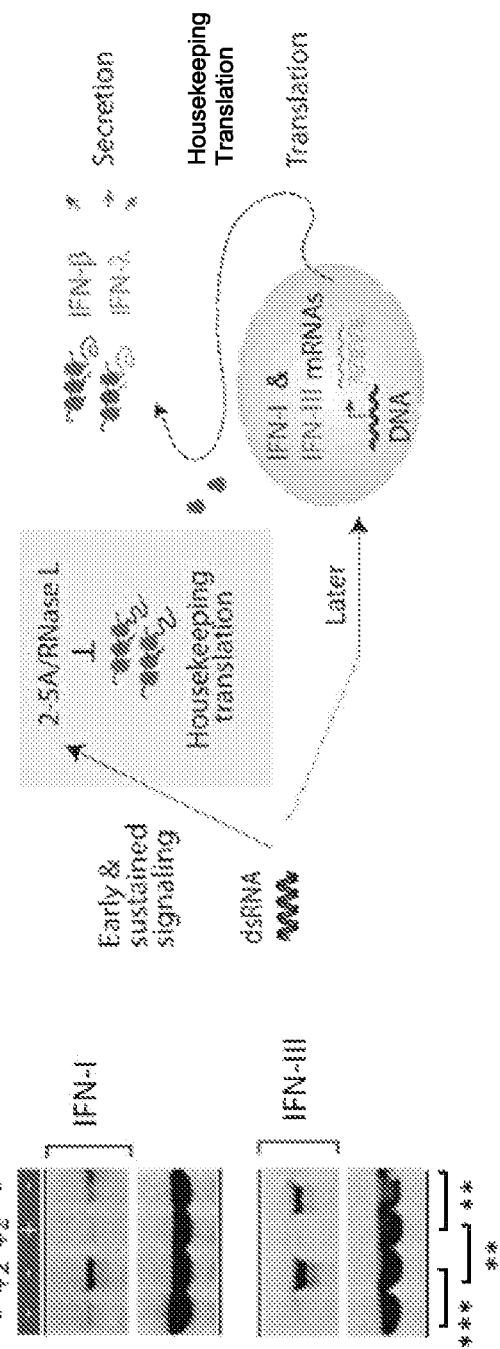

A549 cells treated with poly-IC express both type I and type III interferons (FIG. 10A). To determine which of these IFNs escape RNase L in our experiments, we employed hamster CHO reporter cell lines developed previously for specific detection of human IFNs of type I and type III. Hamster cells do not respond to human IFNs, however the reporter cells are rendered sensitive via expression of chimeric type I and type III human IFN receptors fused to a potent STAT1 docking domain (Huang, supra; Kotenko, supra). The reporter cells analysis, based on readout of phospho-STAT, indicates the presence of type I and type III IFNs, exhibiting strongest p-STAT response to IFNs-λ (FIG. 10B).

Conclusion

A biosensor for 2-5A was developed and it was determined that this second messenger is synthesized without a delay and mediates immediate dsRNA sensing. 2-5A activates RNase L, which suppresses protein synthesis (Taniuchi et al., Sci Rep 6:32886 (2016)). This mechanism is potent and attenuates basal cell-wide translation by more than 1,000-fold. Using this biosensor, it was noted that 2-5A arrests host translational activity prior to induction of the interferon response. The translation-arrested cells still maintain efficient production and secretion of IFNs β and λ. The results herein thus kinetically separates RNA cleavage and translational shutoff by RNase L from interferon-mediated cellular reprogramming, revealing an unanticipated order of signaling events where basal translation is shut down first and the IFN response develops second.

The action of RNase L resembles arrest of the initiation step, which can be accompanied by a characteristic collapse of polysomes (Clemens et al., Cell 13:565-72 (1978)). A similar polysomal collapse is observed upon activation of integrated stress response (ISR) that employs serine/threonine kinases to phosphorylate and inactivate the translation initiation factor eIF2α (Iwasaki et al., Nature 534:558-61 (2016)). In the ISR, the arrest of translational initiation can be bypassed by mRNAs encoding stress proteins, such as ATF4 and IBTKα due to the presence of 5' uORFs that increase translation under conditions of limiting initiation (Donovan, RNA supra). Although it remains unclear how IFNs bypass RNase L and whether they may use a related route (Lane et al., Nature 467:929-34 (2010)), by evading 2-5A/RNase L translational arrest cells may ensure that infection does not prevent the production of IFNs, a central task of the innate immune system. In mice RNase L amplifies IFN protein synthesis (Malathi, supra), indicating that cellular resources released by RNase L upon translational shutoff (translation can consume as much as 75% of a cell's energy balance (Hsieh et al., Nature 485:55-61 (2012)) may become reallocated for enhanced production of IFNs.

The observations of subcellular 2-5A dynamics suggest a possible explanation for the bipartite organization of the OAS-RNase L system. The effector (RNase L) and the dsRNA-sensing moiety (the OASs) in the 2-5A system are separated. This arrangement contrasts with the single-protein structure of another dsRNA sensor, PKR, which encodes the dsRNA-binding domain and the effector kinase domain in the same polypeptide. The results herein indicated that the bipartite arrangement of OASs/RNase L may, sense dsRNA at a distance from the site of RNase L action. The range of OAS-RNase L communication depends on efficiency of 2-5A diffusion, which occurs with rates sufficient for 2-5A equilibration between the nucleus and the cytosol faster than the rate of 2-5A production. Therefore, RNase L is poised to respond to 2-5A from cytoplasmic and nuclear OASs, suggesting that detection of dsRNA in both compartments is a likely biologic function of cytosolic RNase L.

A number of clinically important translation inhibitors, such as rapalogs and a new generation of anticancer drugs based on INK128, work by reprogramming protein synthesis through inhibition of mTOR (Lukacs et al., J Biol Chem 275:625-9 (2000)). The work herein for the first time describes RNase L not as a general RNA decay machine, but as a translation-reprogramming receptor. Normally, RNase L is activated as a part of the innate immune system. However, RNase L activation by small molecules could be explored for developing adjuvants and anticancer therapeutics with some of the beneficial effects of mTOR blockers, and with an added advantage of maintaining the protein synthesis activity of the innate immune system. The search for such on demand activators can be facilitated by biochemical, cell-based as well as in vivo applications of the 2-5A biosensor described here.

Numerous modifications and variations in the disclosure as set forth in the above illustrative examples are expected to occur to those skilled in the art. Consequently only such limitations as appear in the appended claims should be placed on the disclosure.

REFERENCES

1. Hovanessian, A. G. & Justesen, J. The human 2'-5'oligoadenylate synthetase family: unique interferon-inducible enzymes catalyzing 2'-5' instead of 3'-5' phosphodiester bond formation. Biochimie 89, 779-88 (2007).
2. Kristiansen, H., Gad, H. H., Eskildsen-Larsen, S., Despres, P. & Hartmann, R. The oligoadenylate synthetase family: an ancient protein family with multiple antiviral activities. J. Interferon Cytokine Res. 31, 41-7 (2011).
3. Silverman, R. H. Viral encounters with 2',5'-oligoadenylate synthetase and RNase L during the interferon antiviral response. J. Virol. 81, 12720-9 (2007).
4. Chakrabarti, A., Jha, B. K. & Silverman, R. H. New insights into the role of RNase L in innate immunity. J. Interferon Cytokine Res. 31, 49-57 (2011).
5. Zhou, a et al. Interferon action and apoptosis are defective in mice devoid of 2',5'-oligoadenylate-dependent RNase L. EMBO J. 16, 6355-63 (1997).
6. Mullan, P. B. et al. The 2,5 oligoadenylate synthetase/ RNaseL pathway is a novel effector of BRCA1- and interferon-gamma-mediated apoptosis. Oncogene 24, 5492-501 (2005).
7. Banerjee, S. et al. RNase L is a negative regulator of cell migration. Oncotarget 6, (2015).
8. Rath, S. et al. Human RNase L tunes gene expression by selectively destabilizing the microRNA-regulated transcriptome. Proc. Natl. Acad. Sci. U.S.A. 112, 15916-21 (2015).
9. Al-Ahmadi, W., Al-Haj, L., Al-Mohanna, F. a, Silverman, R. H. & Khabar, K. S. a. RNase L downmodulation of the RNA-binding protein, HuR, and cellular growth. Oncogene 28, 1782-91 (2009).
10. Goubau, D., Deddouche, S. & Reis E Sousa, C. Cytosolic sensing of viruses. Immunity 38, 855-69 (2013).
11. Licht, J. D. DNA Methylation Inhibitors in Cancer Therapy: The Immunity Dimension. Cell 162, 938-939 (2015).
12. Lu, C. et al. Recognition by RIG-I C-terminal Domain. 18, 1032-1043 (2011).
13. Wu, B. et al. Structural basis for dsRNA recognition, filament formation, and antiviral signal activation by MDA5. Cell 152, 276-89 (2013).
14. Zhou, a, Hassel, B. a & Silverman, R. H. Expression cloning of 2-5A-dependent RNAase: a uniquely regulated mediator of interferon action. Cell 72, 753-65 (1993).
15. Samuel, M. a et al. PKR and RNase L contribute to protection against lethal West Nile Virus infection by controlling early viral spread in the periphery and replication in neurons. J. Virol. 80, 7009-7019 (2006).

16. Washenberger, C. L. et al. Hepatitis C virus RNA: dinucleotide frequencies and cleavage by RNase L. Virus Res. 130, 85-95 (2007).
17. Li, X.-L. et al. An essential role for the antiviral endoribonuclease, RNase-L, in antibacterial immunity. Proc. Natl. Acad. Sci. U.S.A. 105, 20816-21 (2008).
18. Cooper, D. A., Jha, B. K., Silverman, R. H., Hesselberth, J. R. & Barton, D. J. Ribonuclease L and metal-ion-independent endoribonuclease cleavage sites in host and viral RNAs. Nucleic Acids Res. 42, 5202-5216 (2014).
19. Fabre, O. et al. RNase L controls terminal adipocyte differentiation, lipids storage and insulin sensitivity via CHOP10 mRNA regulation. Cell Death Differ. 19, 1470-81 (2012).
20. Carpten, J. et al. Germline mutations in the ribonuclease L gene in families showing linkage with HPC1. Nat. Genet. 30, 181-4 (2002).
21. Chiappinelli, K. B. et al. Inhibiting DNA Methylation Causes an Interferon Response in Cancer via dsRNA Including Endogenous Retroviruses. Cell 162, 974-986 (2015).
22. Roulois, D. et al. DNA-Demethylating Agents Target Colorectal Cancer Cells by Inducing Viral Mimicry by Endogenous Transcripts. Cell 162, 961-973 (2015).
23. George, C. X., Ramaswami, G., Li, J. B. & Samuel, C. E. Editing of cellular self RNAs by adenosine deaminase ADAR1 suppresses innate immune stress responses. J. Biol. Chem. jbc.M115.709014 (2016). doi:10.1074/jbc.M115.709014
24. White, E., Schlackow, M., Kamieniarz-Gdula, K., Proudfoot, N. J. & Gullerova, M. Human nuclear Dicer restricts the deleterious accumulation of endogenous double-stranded RNA. Nat. Struct. Mol. Biol. 21, 552-9 (2014).
25. Liddicoat, B. J. et al. No Title. (2015).
26. Rice, G. I. et al. Mutations in ADAR1 cause Aicardi-Goutières syndrome associated with a type I interferon signature. Nat. Genet. 44, 1243-8 (2012).
27. Han, Y., Whitney, G., Donovan, J. & Korennykh, A. Innate immune messenger 2-5A tethers human RNase L into active high-order complexes. Cell Rep. 2, 902-13 (2012).
28. Zhao, L. et al. Antagonism of the interferon-induced OAS-RNase L pathway by murine coronavirus ns2 protein is required for virus replication and liver pathology. Cell Host Microbe 11, 607-16 (2012).
29. (ppp(A2'p)nA). 9, 1571-1581 (1981).
30. Thakur, C. S., Xu, Z., Wang, Z., Novince, Z. & Silverman, R. H. A Convenient and Sensitive Fluorescence Resonance Energy Transfer Assay for RNase L. 116, 103-113
31. Han, Y. et al. Structure of human RNase L reveals the basis for regulated RNA decay in the IFN response. Science 343, 1244-8 (2014).
32. Manuscript, A. & Complementation, S.-F. L. F. NIH Public Access. 79, 2346-2353 (2011).
33. Williams, B. R., Kerr, I. M., Gilbert, C. S., White, C. N. & Ball, L. A. Synthesis and breakdown of pppA2'p5'A2'p5'A and transient inhibiton of protein synthesis in extracts from interferon-treated and control cells. Eur. J Biochem. 92, 455-462 (1978).
34. Kjaer, K. H. et al. Mitochondrial localization of the OAS1 p46 isoform associated with a common single nucleotide polymorphism. BMC Cell Biol. 15, 33 (2014).
35. Besse, S., Rebouillat, D., Marie, I., Puvion-Dutilleul, F. & Hovanessian, a G. Ultrastructural localization of interferon-inducible double-stranded RNA-activated enzymes in human cells. Exp. Cell Res. 239, 379-392 (1998).

What is claimed:

1. A fusion protein comprising RNase L or a fragment thereof fused to a reporter protein, wherein fragments of the reporter protein are fused to both the N-terminal side and the C-terminal side of the RNase L protein or fragment thereof, and wherein the RNase L or fragment thereof binds to 2'-5' linked oligoadenylates (2-5A).

2. The fusion protein of claim 1, wherein the reporter protein is selected from the group consisting of luciferase, green fluorescent protein (GFP), red fluorescent protein (RFP), yellow fluorescent protein (YFP) and sfCHERRY.

3. The fusion protein of claim 1, wherein the luciferase comprises an N-terminal fragment of luciferase on one side of the RNase L or fragment thereof and a C-terminal fragment of luciferase is fused to the opposite side of the RNase L or fragment thereof from the N-terminal fragment of luciferase.

4. A fusion protein comprising RNase L or a fragment thereof fused to a reporter protein, wherein fragments of the reporter protein are fused to both the N-terminal side and the C-terminal side of the RNase L protein or fragment thereof, wherein the luciferase comprises an N-terminal fragment of luciferase on one side of the RNase L or fragment thereof and a C-terminal fragment of luciferase is fused to the opposite side of the RNase L or fragment thereof from the N-terminal fragment of luciferase, and wherein the luciferase is firefly luciferase and the N-terminal fragment comprises amino acids 1-416 of firefly luciferase and the C-terminal fragment comprises amino acid residues 417-500 of firefly luciferase.

5. A fusion protein comprising RNase L or a fragment thereof fused to a reporter protein, wherein fragments of the reporter protein are fused to both the N-terminal side and the C-terminal side of the RNase L protein or fragment thereof, wherein
   i) the reporter protein is GFP and the N-terminal fragment comprises amino acids 1-214 of GFP and the C-terminal fragment comprises amino acid residues 215-230 of GFP; or
   ii) the reporter protein is sfCHERRY and the N-terminal fragment comprises amino acids 1-208 of sfCHERRY and the C-terminal fragment comprises amino acid residues 209-226 of sfCHERRY.

6. The fusion protein of claim 1, wherein the reporter protein is connected to the RNase L or fragment thereof via one or more linkers, optionally wherein the linker comprises a GGGS linker (SEQ ID NO: 1).

7. The fusion protein of claim 1, wherein the fragment of RNase L comprises all or part of an RNase L ANK domain.

8. The fusion protein of claim 4, wherein the RNase L or fragment thereof binds to 2'-5' linked oligoadenylates (2-5A).

9. The fusion protein of claim 1, further comprising a nuclear localization signal (NLS) or a nuclear export signal (NES).

10. A fusion protein comprising RNase L or a fragment thereof fused to a reporter protein, wherein fragments of the reporter protein are fused to both the N-terminal side and the C-terminal side of the RNase L protein or fragment thereof, wherein binding of RNase L to 2'-5'linked oligoadenylates (2-5A) results in head-to-tail dimerization of the RNase L proteins and activation of the reporter.

11. A nucleotide encoding a fusion protein of claim 1.

12. A vector expressing the fusion protein of claim 1.

13. A composition comprising the fusion protein of claim 1.

14. A method of detecting 2'-5' linked oligoadenylates (2-5A) comprising contacting a sample with a composition comprising a fusion protein of claim 1, wherein an increase in reporter signal compared to control is indicative of an increase in 2-5A in the sample.

15. A method of determining levels of double stranded RNA (dsRNA) in a sample comprising contacting the sample with a composition comprising a fusion protein of claim 1, and detecting levels of dsRNA based on signal emitted from the reporter, wherein an increase in reporter signal compared to control is indicative of an increase in dsRNA in the sample.

16. The method of claim 15, wherein the increase in dsRNA is associated with an infection or autoimmune disease.

17. A method for detecting or monitoring progression of an immune response in a subject comprising
   i) contacting a sample from the subject with a composition comprising a fusion protein of claim 1;
   ii) detecting levels of intracellular double stranded RNA (dsRNA) based on the signal emitted from the reporter, wherein an increase in dsRNA levels compared to control is indicative of an increasing immune response.

18. A method for treating an immune response in a subject comprising
   i) contacting a sample from the subject with a composition comprising a fusion protein of claim 1;
   ii) detecting levels of intracellular double stranded RNA (dsRNA) based on the signal emitted from the reporter, wherein a change in dsRNA levels compared to control is indicative of a modulated immune response; and,
   iii) treating the subject with a therapeutic agent to treat the immune response when there is a change in levels of dsRNA detected.

19. A method for identifying a modulator of 2'-5' linked oligoadenylate (2-5A) binding to RNase L comprising
   i) contacting a sample with a composition comprising a fusion protein of claim 1 in the presence of a candidate modulator compound, and
   ii) detecting levels of intracellular double stranded RNA (dsRNA) based on the signal emitted from the reporter after step (i),
   wherein when the compound increases 2-5A binding to RNase L and increases dsRNA, the modulator is useful as a cancer therapeutic or anti-viral; or
   wherein when the compound decreases 2-5A binding to RNase L and decreases dsRNA, the modulator is useful as a therapeutic to treat autoimmune disease associated with self-dsRNA.

20. A kit comprising a composition comprising a fusion protein comprising RNase L or a fragment thereof fused to a reporter protein, wherein fragments of the reporter protein are fused to both the N-terminal side and the C-terminal side of the RNase L protein or fragment thereof, and instructions for use.

* * * * *

UNITED STATES PATENT AND TRADEMARK OFFICE
CERTIFICATE OF CORRECTION

| | |
|---|---|
| PATENT NO. | : 11,667,949 B2 |
| APPLICATION NO. | : 16/277632 |
| DATED | : June 6, 2023 |
| INVENTOR(S) | : Alexei Korennykh et al. |

It is certified that error appears in the above-identified patent and that said Letters Patent is hereby corrected as shown below:

In the Claims

Column 79, Line 60, Claim 10, "2′-5′linked" should be -- 2′-5′ linked --.

Signed and Sealed this
Twentieth Day of February, 2024

Katherine Kelly Vidal
*Director of the United States Patent and Trademark Office*